United States Patent
Conner et al.

(10) Patent No.: US 7,259,175 B2
(45) Date of Patent: Aug. 21, 2007

(54) PEROXISOME PROLIFERATOR ACTIVATED RECEPTOR MODULATORS

(75) Inventors: Scott Eugene Conner, Elizabethtown, IN (US); Nathan Bryan Mantlo, Brownsburg, IN (US); Guoxin Zhu, Noblesville, IN (US)

(73) Assignee: Eli Lilly and Company, Idianapolis, IN (US)

( * ) Notice: Subject to any disclaimer, the term of this patent is extended or adjusted under 35 U.S.C. 154(b) by 247 days.

(21) Appl. No.: 10/505,103

(22) PCT Filed: Feb. 13, 2003

(86) PCT No.: PCT/US03/02680

§ 371 (c)(1),
(2), (4) Date: Aug. 17, 2004

(87) PCT Pub. No.: WO03/072102

PCT Pub. Date: Sep. 4, 2003

(65) Prior Publication Data

US 2006/0084663 A1    Apr. 20, 2006

Related U.S. Application Data

(60) Provisional application No. 60/359,807, filed on Feb. 25, 2002.

(51) Int. Cl.
*A61K 31/497* (2006.01)
*A61K 31/501* (2006.01)
*A61K 31/506* (2006.01)
*A61K 31/4439* (2006.01)
*C07D 417/10* (2006.01)
*C07D 413/10* (2006.01)

(52) U.S. Cl. ............ 514/342; 514/252.05; 514/255.05; 514/256; 514/340; 544/238; 544/333; 544/405; 546/269.7; 546/272.1

(58) Field of Classification Search ................ 548/202, 548/235; 514/365, 374, 252.05, 255.05, 514/256, 340, 342; 544/238, 333, 405; 546/269.7, 546/272.1
See application file for complete search history.

(56) References Cited

U.S. PATENT DOCUMENTS 5,591,862 A * 1/1997 Sohda et al. ................ 548/235

FOREIGN PATENT DOCUMENTS

| EP | 0 930 299 A | 7/1999 |
|---|---|---|
| WO | WO9946232 A1 * | 9/1999 |
| WO | WO99 66915 A2 | 12/1999 |
| WO | WO99 66915 A3 | 12/1999 |
| WO | WO 01 00603 A | 1/2001 |
| WO | WO 0100603 A1 * | 1/2001 |
| WO | WO 01 16120 A | 3/2001 |
| WO | WO 02 18355 A | 3/2002 |
| WO | WO 02 058098 A | 8/2002 |
| WO | WO 02 062774 A | 8/2002 |
| WO | WO 02 092084 A | 11/2002 |
| WO | WO 03 072102 A | 9/2003 |

OTHER PUBLICATIONS

Duriez et al. Exp. Opin. Invest. Drugs 1998, 7(11), 1997-2009.*

* cited by examiner

*Primary Examiner*—Kamal A. Saeed
*Assistant Examiner*—Jason M. Nolan
(74) *Attorney, Agent, or Firm*—MaCharri R. Vorndran-Jones

(57) ABSTRACT

The present invention is directed to compounds represented by the following structural formula, and pharmaceutically acceptable salts thereof, Formula I: wherein: (a) R5 is selected from the group consisting of $(C_1-C_6)$ alkyl, $(C_1-C_6)$ alkenyl, substituted aryl$(C_0-C_4)$alkyl, substituted aryloxy $(C_0-C_4)$alkyl, substituted arylthio$(C_0-C_4)$alkyl, unsubstituted aryl$(C_0-C_4)$alkyl, unsubstituted aryloxy$(C_0-C_4)$alkyl, and unsubstituted arylthio$(C_0-C_4)$alkyl; (b) T1 is C or N; (c) Q is selected from the group consisting of O, a single bond, $O(CH_2)_q$ and C; (d) q is 1 or 2; (e) W is selected from the group consisting of O, S, $(CH_2)_rN(R20)(CH_2)_k$, $NHSO_2$, $C(O)N(R20)(CH_2)_r$, $(CH_2)_rN(R20)C(O)$, and $SO_2$; (f) X is $C_mH_{2m}$; (g) m is 0, 1 or 2; (h) A is an functional group selected from the group consisting of carboxyl, C1-C3 alkylnitrile, carboxamide, and $(CH_2)_n$ COOR19; and (i) R19 is selected from the group consisting of hydrogen, optionally substituted C1-C4alkyl and optionally substituted arylmethyl

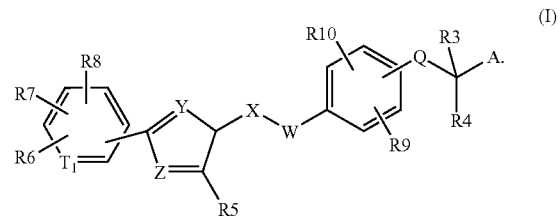
(I)

22 Claims, No Drawings

PEROXISOME PROLIFERATOR ACTIVATED RECEPTOR MODULATORS

This Application claims the benefit of U.S. Provisional Application Ser. No. 60/359,807, filed Feb. 25, 2002 and PCT Application Ser. No. PCT/US03/02680, filed Feb. 13, 2003.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists which have been shown to increase the sensitivity of insulin sensitive cells. Increasing insulin sensitivity rather than the amount of insulin in the blood reduces the likelihood of hypoglycemic coma. However, TZDs and ISEs typically have little effect in preventing the cardiovascular part of Syndrome X in that their administration usually dose not result in the lowering of triglycerides and LDL-cholesterol while raising HDL-cholesterol. Furthermore, side effects commonly associated with treatment with TZDs include significant weight gain, and, for troglitazone, liver toxicity. Therefore, a need exists for new pharmaceutical agents which affect, treat or prevent cardiovascular disease, particularly that associated with Syndrome X, while preventing or minimizing weight gain, and more preferably while improving insulin sensitivity. It may be especially desirable when the active pharmaceutical agent selectively modulates a PPAR receptor subtype to provide an especially desirable pharmacological profile.

SUMMARY OF THE INVENTION

The present invention is directed to compounds represented by the following structural Formula I:

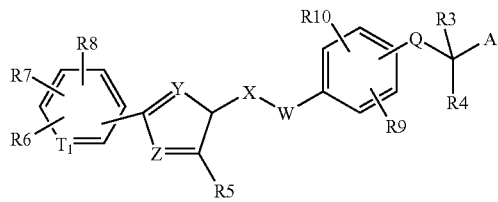

and pharmaceutically acceptable salts thereof, wherein:
(a) R3 is selected from the group consisting of hydrogen and C1-C3 alkoxy;
(b) R4 is selected from the group consisting of hydrogen and $C_1$-$C_4$ alkyl;
(c) R5 is selected from the group consisting of ($C_1$-$C_6$) alkyl, ($C_1$-$C_6$) alkenyl, aryl($C_0$-$C_4$)alkyl, aryloxy($C_0$-$C_4$)alkyl, arylthio($C_0$-$C_4$)alkyl, wherein said aryl($C_0$-$C_4$)alkyl, aryloxy($C_0$-$C_4$)alkyl, and arylthio($C_0$-$C_4$) alkyl are each independently optionally substituted with from one to three substituents each independently selected from R5';
(d) R5' are each independently selected from the group consisting of halo, —(O)—($C_1$-$C_5$)alkylCOOH, $C_1$-$C_5$alkylCOOH, $C_1$-$C_5$ alkyl, and $CF_3$;
(e) R6 is selected from the group consisting of trifluoromethyl, trifluoromethoxy, hydroxy($C_1$-$C_3$)alkyl, ($C_1$-$C_4$)alkyl, —C(O) ($C_1$-$C_4$)alkyl, —O—($C_1$-$C_2$)alkyl-$CO_2$H, aryloxy, arylthio, [1,3,2]dioxaborolanyl, pyridinyl, pyrimidinyl, pyrazinyl and aryl($C_0$-$C_4$)alkyl, wherein said pyridinyl, pyrimidinyl, pyrazinyl, aryl($C_0$-$C_4$)alkyl, aryloxy, and arylthio are each optionally substituted with from one to three substituents independently selected from R6', with the proviso that when $T_1$ is C and R6 is aryl($C_0$-$C_4$)alkyl, then said aryl($C_0$-$C_4$)alkyl is substituted with at least one substituent selected from R6';
(f) R6' is independently selected from the group consisting of $CF_3$, $C_1$-$C_4$ alkyl, halo, hydroxy($C_0$-$C_3$)alkyl, $C_1$-$C_3$ alkoxy, and —$C(O)CH_3$;
(g) R7 and R8 are each independently selected from the group consisting of hydrogen, ($C_1$-$C_6$) alkyl, and trifluoromethyl;
(h) R9 and R10 are each independently selected from the group consisting of hydrogen, ($C_1$-$C_4$) alkyl, ($C_1$-$C_3$) alkenyl, halo, and ($C_1$-$C_4$) alkoxy;
(i) $T_1$ is N or C;
(j) Q is selected from the group consisting of O, a single bond, $O(CH_2)_q$ and C;
(k) q is 1 or 2;
(l) W is selected from the group consisting of O, S, $(CH_2)_rN(R20)$ $(CH_2)_k$, $NHSO_2$, $C(O)N(R20)$ $(CH_2)_r$, $(CH_2)_rN(R20)C(O)$, and $SO_2$;
(m) r is selected from the group consisting of 0, 1, and 2;
(n) k is selected from the group consisting of 0, 1, and 2;
(o) R20 is selected from the group consisting of H, $C_1$-$C_3$ alkyl, C(O)OR23, and

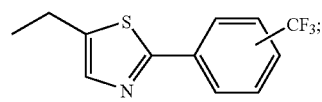

(p) R23 is selected from the group consisting of H and $C_1$-$C_3$ alkyl;
(q) X is $C_mH_{2m}$;
(r) m is selected from the group consisting of 0, 1 and 2;
(s) Y and Z are each independently selected from the group consisting of N, S, and O, with the proviso that at least one of Y and Z is selected from the group consisting of S and O;
(t) A is selected from the group consisting of carboxyl, $C_1$-$C_3$ alkylnitrile, carboxamide, and $(CH_2)_n$COOR19;
(u) n is 0, 1, 2 or 3; and
(v) R19 is selected from the group consisting of hydrogen, C1-C4alkyl and arylmethyl, wherein said alky and arylmethyl are each optionally substituted with from one to three substituents each independently selected from R19';
(w) R19' are each independently selected from the group consisting of halo, —(O)—($C_1$-$C_5$)alkylCOOH, $C_1$-$C_5$ alkyl, and $CF_3$;
with the proviso that when R3 and R4 are each hydrogen, and at least one selected from the group consisting of R6, R7 and R8 is $CF_3$, then R5 is selected from the group consisting of ($C_3$-$C_6$) alkyl, ($C_1$-$C_6$) alkenyl, substituted aryl($C_0$-$C_4$)alkyl, substituted aryloxy($C_0$-$C_4$)alkyl, substituted arylthio($C_0$-$C_4$)alkyl, unsubstituted aryl($C_0$-$C_4$)alkyl, unsubstituted aryloxy($C_0$-$C_4$) alkyl, and unsubstituted arylthio($C_0$-$C_4$)alkyl.

Another embodiment of the present invention is a compound of Formula I':

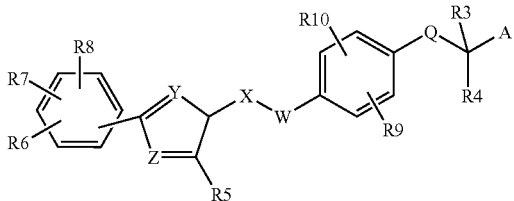

and pharmaceutically acceptable salts thereof, wherein:
(a) R3 is selected from the group consisting of hydrogen and C1-C3 alkoxy;
(b) R4 is selected from the group consisting of hydrogen and $C_1$-$C_4$ alkyl;
(c) R5 is selected from the group consisting of ($C_1$-$C_6$) alkyl, ($C_1$-$C_6$) alkenyl, substituted aryl($C_0$-$C_4$)alkyl, substituted aryloxy($C_0$-$C_4$)alkyl, substituted arylthio ($C_0$-$C_4$)alkyl, unsubstituted aryl($C_0$-$C_4$)alkyl, unsubstituted aryloxy($C_0$-$C_4$)alkyl, and unsubstituted arylthio ($C_0$-$C_4$)alkyl;
(d) R6 is selected from the group consisting of trifluoromethyl, hydroxy($C_1$-$C_3$)alkyl, ($C_1$-$C_4$)alkyl, —C(O) ($C_1$-$C_4$)alkyl, —O—($C_1$-$C_2$)alkyl-$CO_2$H, and substituted aryl($C_0$-$C_4$)alkyl;
(e) R7 and R8 are each independently selected from the group consisting of hydrogen, ($C_1$-$C_6$) alkyl, and trifluoromethyl;
(f) R9 and R10 are each independently selected from the group consisting of hydrogen, ($C_1$-$C_4$) alkyl, ($C_1$-$C_3$) alkenyl, halo, and ($C_1$-$C_4$) alkoxy;
(g) Q is selected from the group consisting of O and C;
(h) W is selected from the group consisting of O, S, and $SO_2$;
(i) X is $C_mH_{2m}$;
(j) m is 1 or 2;
(k) Y and Z are each independently selected from the group consisting of N, S, and O;
(l) A is an functional group selected from the group consisting of carboxyl, $C_1$-$C_3$alkylnitrile, carboxamide, and $(CH_2)_n$COOR19;
(m) n is 0, 1, 2 or 3; and
(n) R19 is selected from the group consisting of hydrogen, optionally substituted C1-C4alkyl and optionally substituted arylmethyl;
with the proviso that when R3 and R4 are each hydrogen, and at least one selected from the group consisting of R6, R7 and R8 is $CF_3$, then R5 is selected from the group consisting of ($C_3$-$C_6$) alkyl, ($C_1$-$C_6$) alkenyl, substituted aryl($C_0$-$C_4$)alkyl, substituted aryloxy($C_0$-$C_4$)alkyl, substituted arylthio($C_0$-$C_4$)alkyl, unsubstituted aryl($C_0$-$C_4$)alkyl, unsubstituted aryloxy($C_0$-$C_4$) alkyl, and unsubstituted arylthio($C_0$-$C_4$)alkyl.

In another feature of this invention, a compound claimed herein is radiolabeled.

In one embodiment, the present invention also relates to pharmaceutical compositions which comprising at least one compound of the present invention, or a pharmaceutically acceptable salt thereof, and a pharmaceutically acceptable carrier.

In another embodiment, the present invention relates to a method of selectively modulating a PPAR alpha receptor by contacting the receptor with at least one compound represented by Structural Formula I, and pharmaceutically acceptable salts thereof.

In another embodiment, the present invention relates to a method of modulating one or more of the PPAR alpha, gamma, and/or delta receptors.

In another embodiment, the present invention contemplates the use of one or more compounds of Formula I for selectively modulating a delta receptor.

In a further embodiment, the present invention relates to a method of making a compound represented by Structural Formula I.

The compounds of the present invention can be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. In addition, the compounds can be associated with fewer clinical side effects than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, when m is 0, then X is absent.

As used herein, when Q is a bond or a single bond, then Q is absent.

As used herein, alkyl groups include straight chained or branched hydrocarbons, which are completely saturated.

Cycloalkyl groups, as used herein, include cyclic hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl). One especially preferred aryl is phenyl.

When R19 is substituted, it is preferred that there are from 1-3 substitutions on said R19 group. When R5 or R6 are substituted, it is especially preferred that there are 1 or 2 independent substituents on said R5 or R6 group.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

As used herein, the phrase "selectively modulate" means a compound whose EC50 for the stated PPAR receptor is at least ten fold lower than its EC50 for the other PPAR receptor subtypes.

"Pharmaceutically-acceptable salt" refers to salts of the compounds of the Structural Formula I which are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases.

Compounds of Structural Formula I, which are substituted with a basic group, may exist as salts with pharmaceutically acceptable acids. The present invention includes such salts. These salts may be prepared by methods known to those skilled in the art.

The term, active ingredient means the compounds generically described by Structural Formula I as well as the salts of such compounds.

The term pharmaceutically acceptable means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

Preventing refers to reducing the likelihood that the recipient will incur or develop any of the pathological conditions described herein. The term preventing is particularly applicable to a patient that is susceptible to the particular patholical condition.

Treating refers to mediating a disease or condition and preventing, or mitigating, its further progression or ameliorating the symptoms associated with the disease or condition.

"Pharmaceutically-effective amount" means that amount of a compound, or of its salt thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount sufficient to modulate a selected PPAR receptor or to prevent or mediate a disease or condition. Conditions prevented or treated by modulation of one or more PPAR receptors include diabetes mellitus, cardiovascular disease, Syndrome X, obesity and gastrointestinal disease. Generally, the effective amount of a Compound of Formula I will be between 0.02 through 5000 mg per day. Preferably 1 through 1,500 mg per day. The desired dose may be presented in a single dose or as divisded doses administered at appropriate intervals.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof to a hyperglycemic human or non-human mammal in need thereof.

The invention also relates to the use of a compound of Formula I as described above, for the manufacture of a medicament for use in treating a PPAR receptor mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In adition, a therapeutically effective amount of a compound, used to prevent or treat NIDDM, typically reduces serum glucose levels, or more specifically HbA1c, of a patient by about 0.7% or more.

Advantageously, compositions containing the compound of Structural Formula I or the salts thereof may be provided in dosage unit form, preferably each dosage unit containing from about 1 to about 500 mg. It will, of course, be readily understood that the amount of the compound(s) of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, autoimmune conditions, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition containing a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, have valuable pharmacological properties and can be used in pharmaceutical compositions containing a therapeutically effective amount of a compound of the present invention, or pharmaceutically acceptable salts thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules. A solid carrier can be one or more substances that may also act as flavoring agents, lubricants, solubilisers, suspending agents, binders, tablet disintegrating agents and encapsulating material.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

The following pharmaceutical formulations 1 and 2 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful as pharmaceutical agents and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:
  a) R3 and R4 are each hydrogen;
  b) R3 and R4 are each methyl;
  c) R3 is hydrogen;
  d) R4 is methyl;
  e) R3 is alkoxy;
  f) A is carboxyl;
  g) R9 is methyl;
  h) R10 is hydrogen;
  i) Q is O;
  j) Q is C;
  k) W is O;
  l) X is $CH_2$;
  m) Z is N;
  n) Z is O;
  o) Y is O;
  p) Y is S;
  q) R5 is $C_2$-$C_6$ alkyl;
  r) R5 is substituted aryloxyalkyl;
  s) R5 is $C_1$-$C_4$alkyl;
  t) R5 is arylalkyl;
  u) R6 is $CF_3$;
  v) R6 is pyrazinyl;
  w) R6 is pyradinyl;
  x) R6 is pyrimidinyl;
  y) R7 is $CF_3$;
  z) R7 is $CH_3$;
  aa) R8 is hydrogen;
  bb) $T_1$ is C;
  cc) $T_1$ is N;
  dd) W is attached to the phenyl ring in a meta position relative to Q;
  ee) aryl is a phenyl group;
  ff) A compound of Formula I that selectively modulates a delta receptor;
  gg) A compound of Formula I that is a PPAR coagaonist that modulates a gamma receptor and a delta receptor;
  hh) A compound of Formula I for use in the treatment of cardiovascular disease;
  ii) A compound of Formula I for use in the treatment of Syndrome X;
  jj) A compound of Formula I for use in the control of obesity;
  kk) A compound of Formula I for use in treating diabetes.

Synthesis

Compounds of the present invention have been formed as specifically described in the examples. Further, many compounds are prepared as more generally as shown in the following schematics. Alternative synthesis methods may also be effective and known to the skilled artisan.

For example, an intermediate like A is alkylated with an alkyl halide like agent B in the presence of a base (e.g. K2CO3, Cs2CO3 etc.). Hydrolysis in the presence of aqueous NaOH or LiOH gave the acid product.

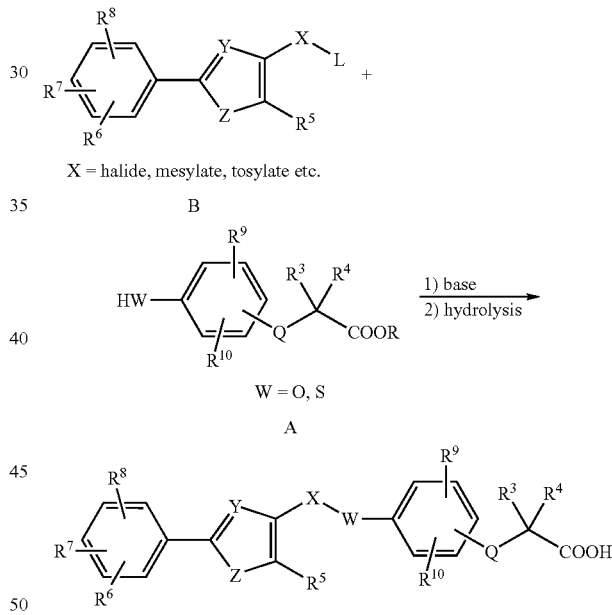

Alternatively, an intermediate like A is coupled with an alcohol C under Mitsunobu reaction condition (DEAD/ PPh3, ADDP/Pbu3 etc.). Hydrolysis in the presence of aqueous NaOH or LiOH gave the acid product:

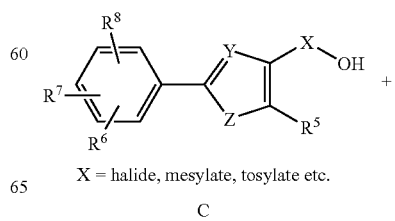

X = halide, mesylate, tosylate etc.

C

-continued

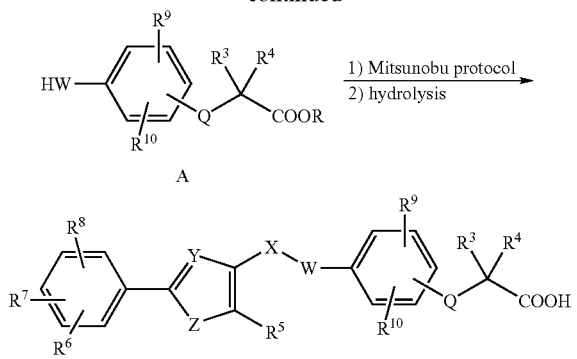

For the compounds with nitrogen in the linker, reductive amination protocol is used, for example:

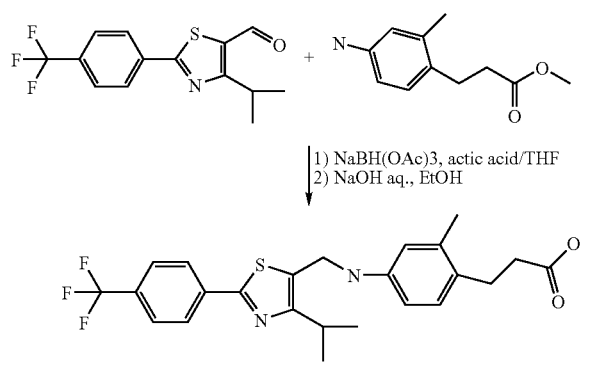

Suzuki coupling or Stille coupling reactions are used for the biaryl compound synthesis:

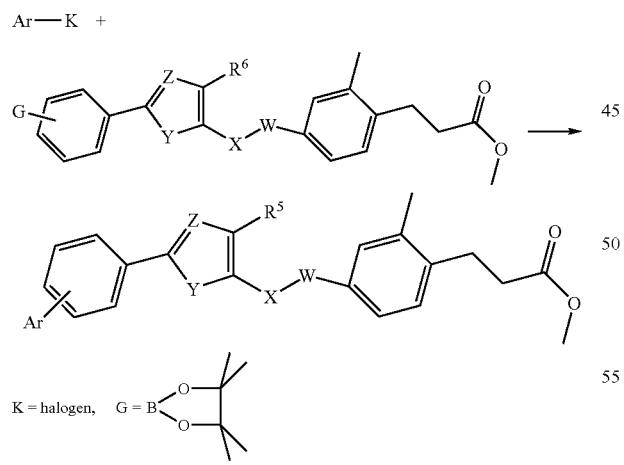

EXEMPLIFICATION

The Examples provided herein are illustrative of the invention claimed herein and are not intended to limit the scope of the claimed invention in any way.

Instrumental Analysis

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

Preparation 1

3-Oxo-5-phenyl-pentanoic acid ethyl ester

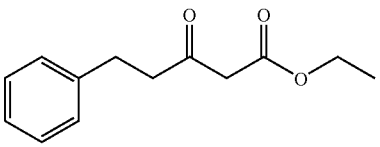

Ethyl acetoacetate (2.32 g, 20 mmol) is added to a pre-cold solution of LDA (2.0 M, 20 mL, 40 mmol) in THF (100 mL) at 0° C. After addition, the mixture is stirred for 30 min, then benzyl bromide (3.42 g, 20 mmol) is added dropwise. After stirred at 0° C. for 30 min, the reaction is quenched by 5 N HCl, extracted with ethyl ether. The combined organic layers are washed with water and brine until it is neutral. Concentration and column chromatography gave 1.6 g of the title compounds.

The following compounds are made in a similar manner:

Preparation 2

5-(2-Chloro-6-fluoro-phenyl)-3-oxo-pentanoic acid ethyl ester

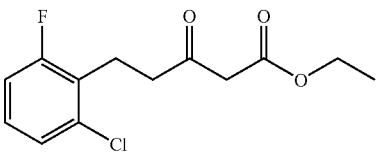

Preparation 3

3-Oxo-hept-6-enoic acid ethyl ester

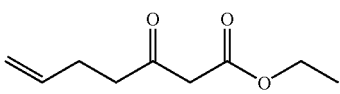

Preparation 4

2-Chloro-3-Oxo-5-phenyl-pentanoic acid ethyl ester

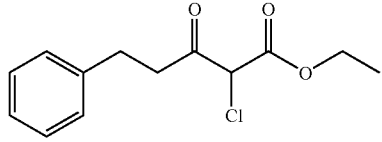

To a solution of 3-oxo-5-phenyl-pentanoic acid ethyl ester (1.6 g, 7.76 mmol) in methylene chloride (18 mL) is added sulfuryl chloride (1.15 g, 8.53 mmol) dropwise. After stirred at room temperature for 6 hours, the reaction mixture is poured into water, extracted with methylene chloride, washed wwashed water and brine, dried over sodium sulfate. Concentration gave the crude title compounds, which is used for the next step without further purification.

The following compounds are made in a similar manner:

Preparation 5

5-(2-Chloro-6-fluoro-phenyl)-2-chloro-3-oxo-pentanoic acid ethyl ester

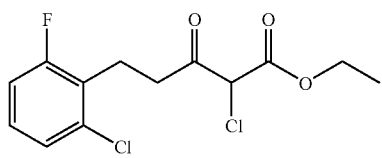

Preparation 6

2-Chloro-3-oxo-hept-6-enoic acid ethyl ester

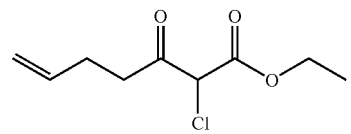

Preparation 7

2-Chloro-3-oxo-heptanoic acid ethyl ester

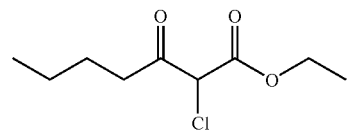

Preparation 8

2-Chloro-3-oxo-hexanoic acid ethyl ester

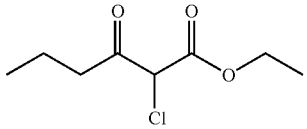

Preparation 9

2-Chloro-4-methyl-3-oxo-pentanoic acid ethyl ester

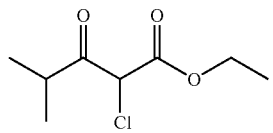

Preparation 10

2-Chloro-4,4-dimethyl-3-oxo-pentanoic acid ethyl ester

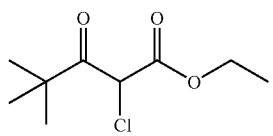

Preparation 11

2-Chloro-3-oxo-3-phenyl-propionic acid ethyl ester

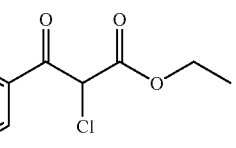

Preparation 12

2-(4-Bromo-phenyl)-4-methyl-thiazole-5-carboxylic acid ethyl ester

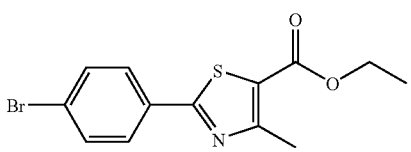

4-Bromo-thiobenzamide (5 g) in toluene is heated at reflux for 1 h in a flask equipped with a Dean-Stark trap. The dry 4-bromo-thioamide (3.4 g, 15 mmol) and ethyl 2-chloroacetoacetate (2.71 g, 16.4 mmol) are heated in ethanol (1000 mL) for overnight. The cooled reaction is concentrated and purified by short path chromatrography. The fractions that contained pure product are concentrated to yield 1.5 g (30.6%) ester as a solid.

Th following thiazoles are made in a similar manner:

Preparation 13

4-Ethyl-2-(4-trifluoromethyl-phenyl)-thiazole-5-carboxylic acid ethyl ester

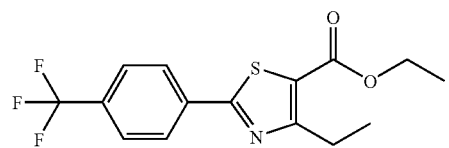

Preparation 14

4-Isoproyl-2-(4-trifluoromethyl-phenyl)-thiazole-5-carboxylic acid ethyl ester

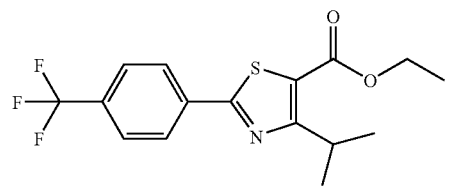

Preparation 15

4-Propyl-2-(4-trifluoromethyl-phenyl)-thiazole-5-carboxylic acid ethyl ester

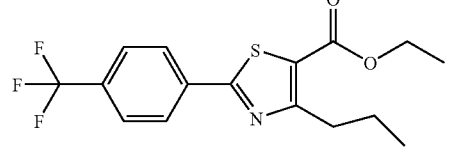

Preparation 16

4-Butyl-2-(4-trifluoromethyl-phenyl)-thiazole-5-carboxylic acid ethyl ester

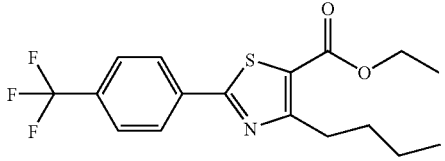

Preparation 17

4-But-3-enyl-2-(4-trifluoromethyl-phenyl)-thiazole-5-carboxylic acid ethyl ester

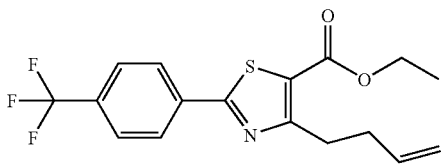

Preparation 18

4-tert-Butyl-2-(4-trifluoromethyl-phenyl)-thiazole-5-carboxylic acid ethyl ester

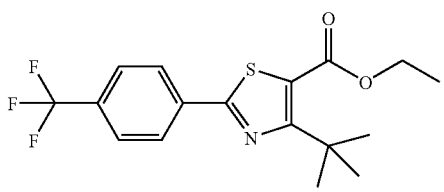

Preparation 19

4-Phenethyl-2-(4-trifluoromethyl-phenyl)-thiazole-5-carboxylic acid ethyl ester

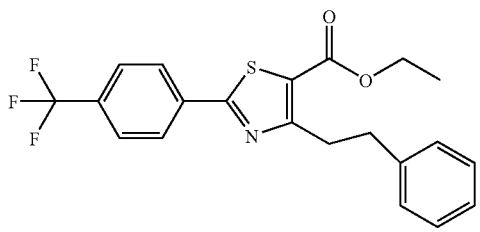

Preparation 20

4-[2-(2-Chloro-6-fluoro-phenyl)-ethyl]-2-(4-trifluoromethyl-phenyl)-thiazole-5-carboxylic acid ethyl ester

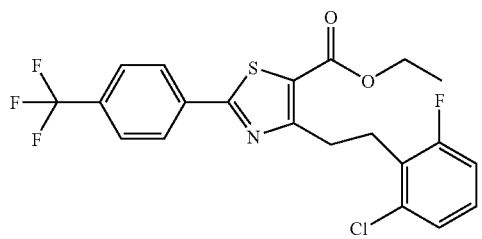

Preparation 21

4-Phenyl-2-(4-trifluoromethyl-phenyl)-thiazole-5-carboxylic acid ethyl ester

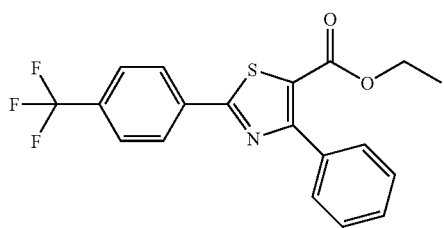

Preparation 22

4-Phenoxymethyl-2-(4-trifluoromethyl-phenyl)-thiazole-5-carboxylic acid ethyl ester

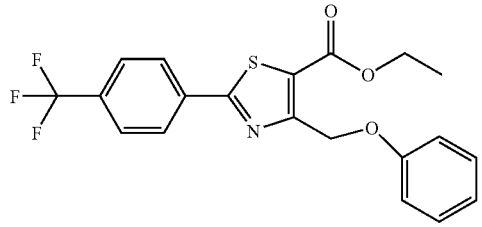

Step A

4-Bromomethyl-2-(4-trifluoromethyl-phenyl)-thiazole-5-carboxylic acid ethyl ester

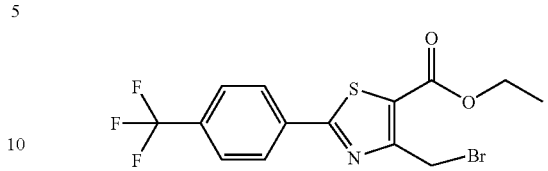

4-Methyl-2-(4-trifluoromethyl-phenyl)-thiazole-5-carboxylic acid ethyl ester (1.6 g, 5.00 mmol) is dissolved into chloroform (50 mL) then N-bromosuccinimide (1.0 g, 5.5 mmol) and 2,2'-azobisisobutyronitrile (0.412 g, 2.5 mmol) are added and the reaction is heated to reflux. The reaction is monitored by TLC until no starting material remained. The reaction is allowed to cool to room temperature, then diluted with more chloroform (100 mL). Water (50 mL) is added and the two phases are separated. The organic layer is washed with brine, then dried over anhydrous sodium sulfate. The material is then concentrated and further purified using flash column chromatography to yield 1.97 g or 99% yield.

Step B

4-Phenoxymethyl-2-(4-trifluoromethyl-phenyl)-thiazole-5-carboxylic acid ethyl ester Phenol (0.518 g, 5.5 mmol) is combined with anhydrous acetonitrile (20 mL) and cesium carbonate (2.3 g, 10 mmol) and allowed to stir at room temperature under nitrogen. To the reaction is added 4-bromomethyl-2-(4-trifluoromethyl-phenyl)-thiazole-5-carboxylic acid ethyl ester (1.97 g, 5.00 mmol). The reaction is monitored by TLC until all of the bromide is consumed. The reaction is diluted with ethyl ether (100 mL), then o.1N NaOH (50 mL) is added. The two phases are separated, then the organic layer is washed with water (50 mL) and brine (50 mL). The organic layer is dried over anhydrous sodium sulfate, then concentrated. The material is further purified using flash chromatography to yield 1.75 g or 86% yield of the product.

The following compounds are made in a similar manner:

Preparation 23

4-(3,5-Bis-trifluoromethyl-phenoxymethyl)-2-(4-trifluoromethyl-phenyl)-thiazole-5-carboxylic acid ethyl ester

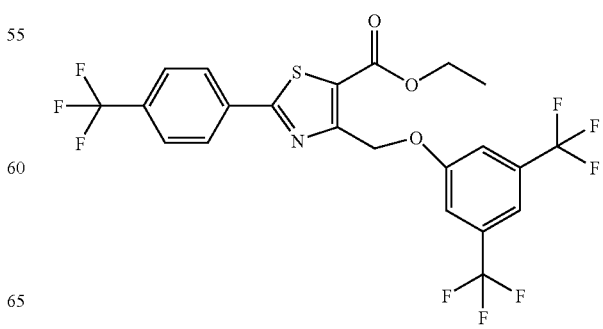

Preparation 24

4-(2-Chloro-6-fluoro-phenoxymethyl)-2-(4-trifluoromethyl-phenyl)-thiazole-5-carboxylic acid ethyl ester

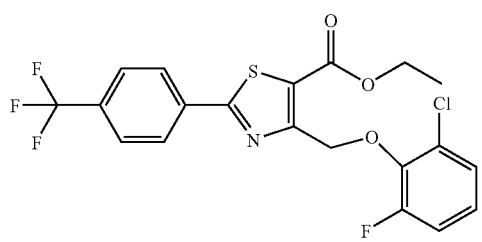

Preparation 25

4-(4-Bromo-phenylsulfanylmethyl)-2-(4-trifluoromethyl-Phenyl)-thiazole-5-carboxylic acid ethyl ester

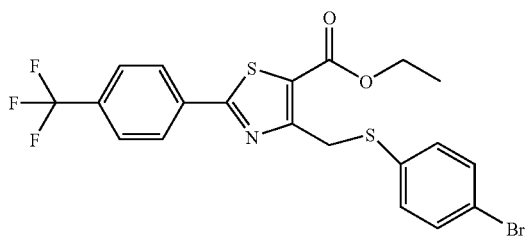

Preparation 26

4-Phenylsulfanylmethyl-2-(4-trifluoromethyl-phenyl)-thiazole-5-carboxylic acid ethyl ester

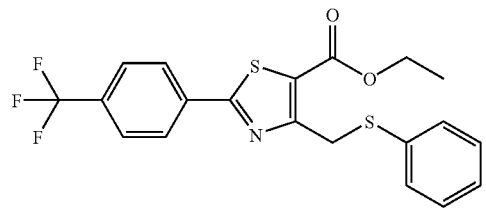

Preparation 27

[4-Methyl-2-(4-trifluoromethyl-phenyl)-thiazol-5-yl]-methanol

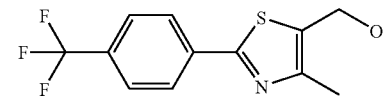

A THF (60 mL) solution of 4-methyl-2-(4-trifluoromethyl-phenyl)-thiazole-5-carboxylic acid ethyl ester (14.9 g, 47.3 mmol) is cooled to 0° C. and a 1M LiAlH$_4$ (47.3 mL, 47.3 mmol) is added slowly. The reaction is warmed to room temperature slowly, after stirring at room temperature for 2 h, tlc (15% EtOAc/hexane) showed that all the starting ester had been consumed. The reaction is cooled and carefully quenched with 2.4 mL water, 2.4 mL 5N NaOH and 7 mL water. The light tan solid is filter through celite and dried to give 7.70 g crude product. Recrystallization from methanol gave pure alcohol.

The following compounds are made in a similar manner:

Preparation 28

[4-Methyl-2-(4-bromo-phenyl)-thiazol-5-yl]-methanol

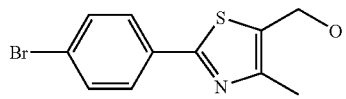

Preparation 29

[4-Ethyl-2-(4-trifluoromethyl-phenyl)-thiazol-5-yl]-methanol

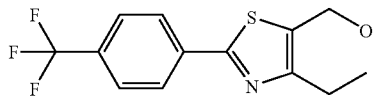

Preparation 30

[4-Isopropyl-2-(4-trifluoromethyl-phenyl)-thiazol-5-yl]-methanol

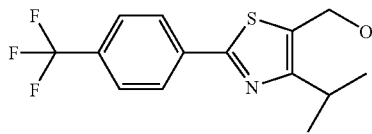

Preparation 31

[4-Propyl-2-(4-trifluoromethyl-phenyl)-thiazol-5-yl]-methanol

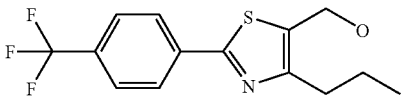

Preparation 32

[4-Butyl-2-(4-trifluoromethyl-phenyl)-thiazol-5-yl]-methanol

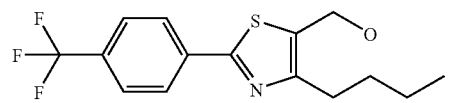

Preparation 33

[4-But-3-enyl-2-(4-trifluoromethyl-phenyl)-thiazol-5-yl]-methanol

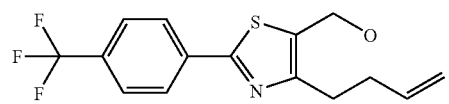

Preparation 34

[4-tert-Butyl-2-(4-trifluoromethyl-phenyl)-thiazol-5-yl]-methanol

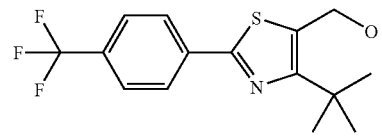

Preparation 35

4-Phenethyl-2-(4-trifluoromethyl-phenyl)-thiazol-5-yl]-methanol

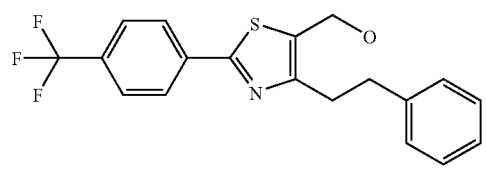

Preparation 36

4-[2-(2-Chloro-6-fluoro-phenyl)-ethyl]-2-(4-trifluoromethyl-phenyl)-thiazol-5-yl]-methanol

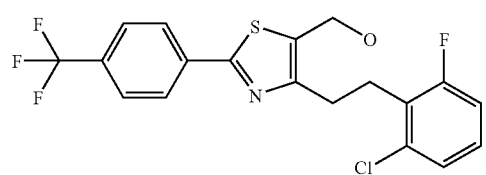

Preparation 37

[4-Phenyl-2-(4-trifluoromethyl-phenyl)-thiazol-5-yl]-methanol

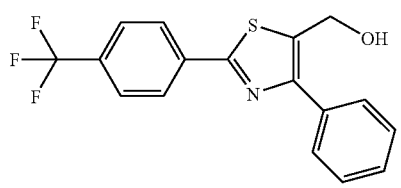

Preparation 38

[4-Phenoxymethyl-2-(4-trifluoromethyl-phenyl)-thiazol-5-yl]-methanol

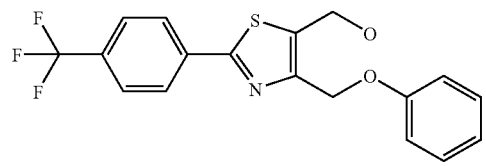

Preparation 39

[4-(2-Chloro-6-fluoro-phenoxymethyl)-2-(4-trifluoromethyl-phenyl)-thiazol-5-yl]-methanol

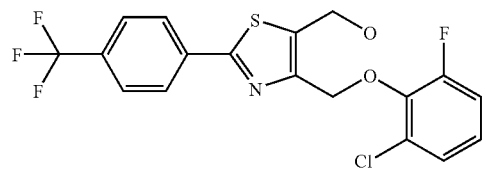

Preparation 40

[4-(3,5-Bis-trifluoromethyl-phenoxymethyl)-2-(4-trifluoromethyl-phenyl)-thiazol-5-yl]-methanol

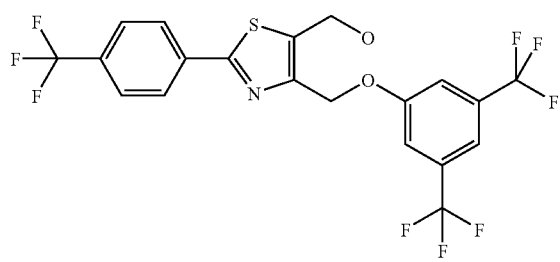

Preparation 41

[4-Phenylsulfanylmethyl-2-(4-trifluoromethyl-phenyl)-thiazol-5-yl]-methanol

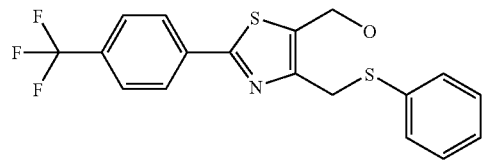

Preparation 42

[4-(4-Bromo-phenylsulfanylmethyl)-2-(4-trifluoromethyl-phenyl)-thiazol-5-yl]-methanol

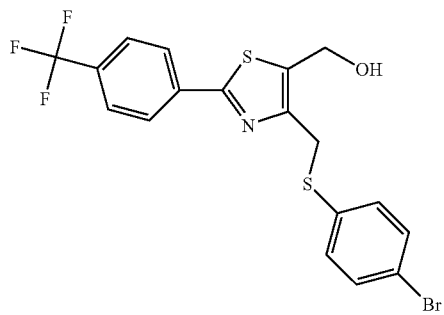

Preparation 43

5-Chloromethyl-4-methyl-2-(4-trifluoromethyl-phenyl)-thiazole

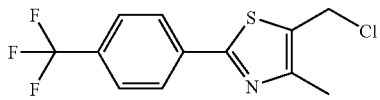

A solution of [4-methyl-2-(4-trifluoromethyl-phenyl)-thiazol-5-yl]-methanol (1.03 g, 3.75 mmol) and triethyl amine (1.05 mL, 7.5 mmol) in methylene chloride (15 mL) is cooled to 0° C., then MeSO2Cl is added dropwise. After 2 hrs, TLC indicated that the reaction is not complete, 10 mol % more of triethyl amine and MeSO$_2$Cl are added. After additional 2 hrs, the reaction mixture is diluted with methylene chloride and washed with sodium bicarbonate, water and brine, dried over sodium sulfate. Concentration gave the crude title compound, which is used for the next step without further purification.

The following compounds are made in a similar manner:

Preparation 44

5-Chloromethyl-4-methyl-2-(4-bromophenyl)-thiazole

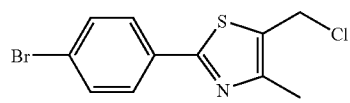

Preparation 45

5-Chloromethyl-4-isopropyl-2-(4-trifluoromethyl-phenyl)-thiazole

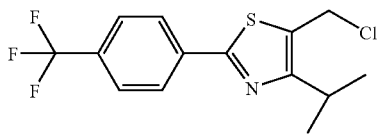

Preparation 46

5-Chloromethyl-4-propyl-2-(4-trifluoromethyl-phenyl)-thiazole

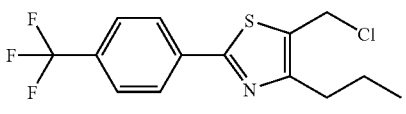

Preparation 47

5-Chloromethyl-4-butyl-2-(4-trifluoromethyl-phenyl)-thiazole

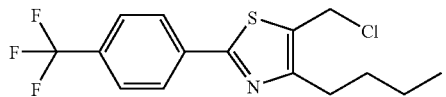

Preparation 48

4-But-3-enyl-5-chloromethyl-2-(4-trifluoromethyl-phenyl)-thiazole

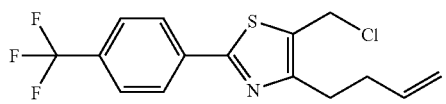

Preparation 49

5-Chloromethyl-4-tert-butyl-2-(4-trifluoromethyl-phenyl)-thiazole

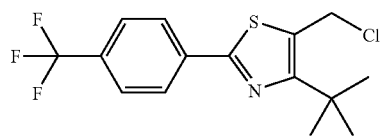

Preparation 50

5-Chloromethyl-4-phenethyl-2-(4-trifluoromethyl-phenyl)-thiazole

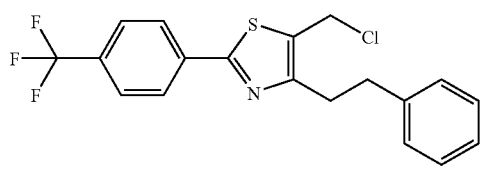

Preparation 51

5-Chloromethyl-4-[2-(2-Chloro-6-fluoro-phenyl)-ethyl]-2-(4-trifluoromethyl-phenyl)-thiazole

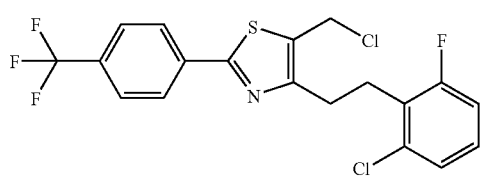

Preparation 52

5-Chloromethyl-4-phenoxymethyl-2-(4-trifluoromethyl phenyl)-thiazole

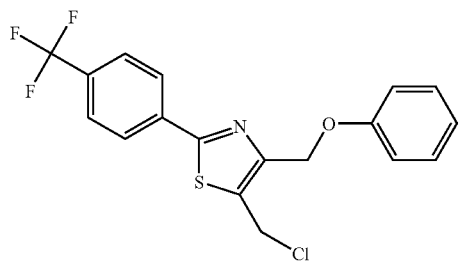

Preparation 53

4-(2-Chloro-6-fluoro-phenoxymethyl)-5-chloromethyl-2-(4-trifluoromethyl-phenyl)-thiazole

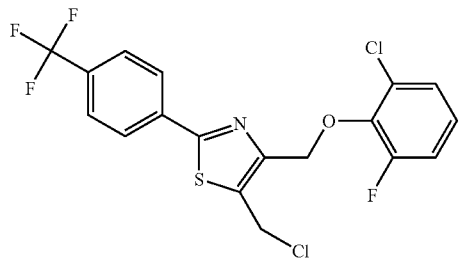

Preparation 54

4-(3,5-Bis-trifluoromethyl-phenoxymethyl)-5-chloromethyl-2-(4-trifluoromethyl-phenyl)-thiazole

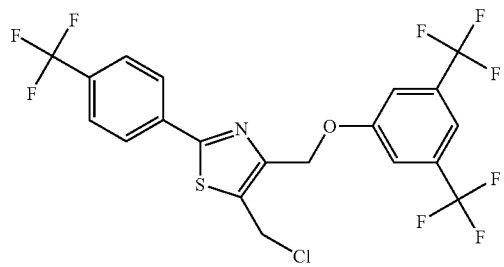

Preparation 55

5-Chloromethyl-4-phenylsulfanylmethyl-2-(4-trifluoromethyl-phenyl)-thiazole

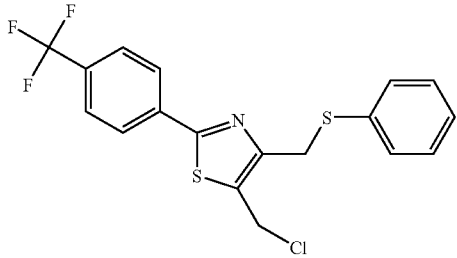

Preparation 56

4-(4-Bromo-phenylsulfanylmethyl)-5-chloromethyl-2-(4-trifluoromethyl-phenyl)-thiazole

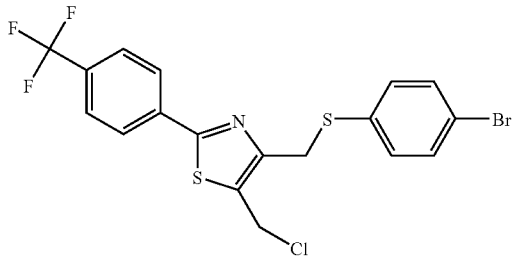

Preparation 57

5-Chloromethyl-4-ethyl-2-(4-trifluoromethyl-phenyl)-thiazole

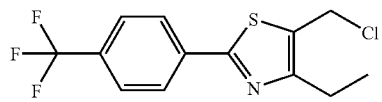

Preparation 58

2-(3,5-Bis-trifluoromethyl-phenyl)-5-chloromethyl-4-methyl-thiazole

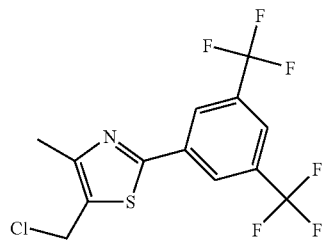

Step A

To a solution of 2-Bromo-4-methyl-thiazole-5-carboxylic acid methyl ester (0.850 g, 3.39 mmol) in toluene:ethanol (1:1) (30 mL) at room temperature under nitrogen is added 3,5-bistrifluormethylbenzene boronic acid (1.0 g, 3.74 mmol). The reaction is purged of air and flushed with nitrogen a few times, followed by addition of tetrakis triphenylphosphine palladium (0.200 g, 0.17 mmol) and sodium carbonate (2.7 mL, 2.5M soln., 6.8 mmol). The reaction is purged again, then heated to reflux under nitrogen and monitored by TLC. After complete consumption of the starting material, the reaction is allowed to cool to room temperature, then diluted with ethyl acetate, celite added, filtered, and the two phases are separated. The organic layer is washed, dried, filtered and concentrated. The crude 2-(3,5-Bis-trifluoromethyl-phenyl)-4-methyl-thiazole-5-carboxylic acid methyl ester (0.545 g, 1.42 mmol), 42% yield, is further purified using flash column chromatography.

Step B 2-(3,5-Bis-trifluoromethyl-phenyl)-4-methyl-thiazole-5-carboxylic acid methyl ester (0.545 g, 1.42 mmol), is dissolved in anhydrous tetrahydrofuran (6 mL) and cooled to 0° C. with stirring under nitrogen. Lithium aluminumhydride, 1.0M in THF, (1.40 mL, 1.40 mmol) is added and the reaction is monitored by TLC. After the starting material is completely consumed, the reaction is quenched with water, base, more water, and celite added, followed by dilution with ether. The mixture is filtered through a plug of celite and the two phases are separated. The organic layer is washed with water and brine, dried over sodium sulfate, then concentrated. The residue is further purified using flash column chromatography. The [2-(3,5-Bis-trifluoromethyl-phenyl)-4-methyl-thiazol-5-yl]-methanol (0.460 g, 1.35 mmol) is formed in 95% yield.

Step C

[2-(3,5-Bis-trifluoromethyl-phenyl)-4-methyl-thiazol-5-yl]-methanol (0.460 g, 1.35 mmol), is dissolved in anhydrous dichloromethane (6 mL) and cooled to 0° C. with stirring under nitrogen. Triethyl amine (0.350 mL, 2.60 mmol) and methane sulfonyl chloride (0.200 mL, 2.0 mmol) are added and the reaction is monitored by TLC. After the starting material is completely consumed, the reaction is diluted with dichloromethane and extracted against saturated sodium bicarbonate solution. The two phases are separated and the organic layer is washed with water and brine, dried over sodium sulfate, then concentrated. The residue is further purified using flash column chromatography. The 2-(3,5-Bis-trifluoromethyl-phenyl)-5-chloromethyl-4-methyl-thiazole is formed quantitatively and used without further purification.

Preparation 59

4-Ethyl-2-(4-trifluoromethyl-phenyl)-oxazole-5-carboxylic acid methyl ester

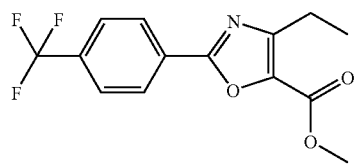

To a solution of 4-trifluoromethyl benzoic acid (0.100 g, 0.239 mmole) in methanol (2.0 mL), is added sodium hydroxide (0.093 g, 0.287 mmole) and stirred at room temperature for 2 hours. The mixture is concentrated to dryness in vacuo to give sodium 4-trifluoromethyl-benzoate as a white solid. It is then mixed with NH$_4$OAc (8.32 g, 107.9 mmole) in glacial acetic acid (500 mL) and heated at 100° C. for 16 hours. After removed the solvents on rotavapor, the residue is partitioned between ethyl acetate (300 mL) and saturated sodium bicarbonate (300 mL). Extracted the aqueous layer with ethyl acetate (300 mL) one more time. The combined organic is ish with brine (3×500 mL), dried over Na$_2$SO$_4$, filtered and concentrated. The crude product is purified by chromatography on silica gel column, gradient elute with 0 to 10% ethyl acetate in hexane and concentrated to provide the titled compound as a white solid. Mass [EI+] 300 (M$^+$+H).

Preparation 60

[4-Ethyl-2-(4-trifluoromethyl-phenyl)-oxazol-5-yl]-methanol

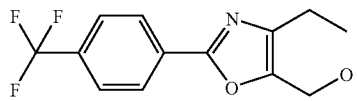

To a solution of 4-Ethyl-2-(4-trifluoromethyl-phenyl)-oxazole-5-carboxylic acid methyl ester (4.63 g, 15.47 mmole) in THF (100 mL), is added LiBH$_4$ in one portion at 0° C. The reaction is warmed up to room temperature and stirred for an hour. Additional LiBH$_4$ is added and the reaction is heated at 60° C. for 30 minutes. The excess amount of LiBH$_4$ is destroyed using 6N HCl (50 mL) dropwise at 0° C. The mixture is partitioned between ethyl acetate (300 mL) and brine (300 mL). The organic layer is washed with brine (3×300 mL), dried over Na$_2$SO$_4$, filtered and concentrated. The crude product is purified by flash chromatography, eluting with 60% ethyl acetate in hexane and concentrated to provide the titled compound as a white solid. Mass [EI+] 272 (M+H)$^+$.

Preparation 61

[4-Methyl-2-(4-trifluoromethyl-phenyl)-oxazol-5-yl]-methanol

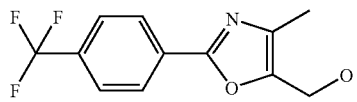

Step 1

2-(4-tert-Butyl-benzoylamino)-propionic acid methyl ester

D, L Alanine methyl ester (18.5 g, 132 mmol), triethylamine (42 mL, 300 mmol) and dichloromethane (300 mL) are stirred in an ice/water bath. 4-(Trifluromethyl)benzoyl chloride (25 g, 120 mmol) is added dropwise and the resulting mixture is allowed to stir for 20 hr at room temperature. 500 mL water and 100 mL 1M hydrochloric acid are successively added. The organic layer is separated, washed with 250 mL each of saturated sodium hydrogen carbonate, water, and brine, dried over anhydrous magnesium sulfate, filtered, and concentrated to 100 mL volume. The mixture is diluted with 200 mL hexanes, cooled to 0° C. for 1 hr, and the white solid filtered and dried under vacuum to afford 2-(4-tert-Butyl-benzoylamino)-propionic acid methyl ester, 26.5 g, 80%. MS (ES): 276 (M$^+$+1).

Step 2

2-(4-tert-Butyl-benzoylamino)-propionic acid

A mixture of 2-(4-tert-Butyl-benzoylamino)-propionic acid methyl ester (26.3 g, 95.6 mmol), 200 mL 1M sodium hydroxide, and 100 mL tetrahydrofuran is stirred at room temperature 20 hr. The resulting clear solution is cooled on an ice/water bath and the pH is adjusted to 2 with concentrated hydrochloric acid. The product is extracted with three 250 mL portions of ethyl acetate. The combined extracts are washed with 100 mL each of water and brine, dried over anhydrous magnesium sulfate, filtered, and concentrated to afford 2-(4-tert-Butyl-benzoylamino)-propionic acid as a white solid, 24.6 g, 95%. MS M$^+$+1 260.

Step 3

[4-Methyl-2-(4-trifluoromethyl-phenyl)-oxazol-5-yl]-methanol

To a solution of 2-(4-Trifluoromethyl-benzoylamino)-propionic acid (33.4 g, 128 mmol) is added oxalyl chloride (111 mL, 1.27 Mol) and 1 drop of DMF and the solution stirred overnight. The volatiles are removed in vacuo and toluene (20 mL) is added. The toluene is then removed in vacuo. To the resultant crude oil is dissolve in 50 mL methylene chloride, cooled to 0° C. and triethylamine (27 mL, 192 mmol) is added followed by methanol (50 mL). After 3 hrs the volatiles are removed in vacuo and the crude oil is purified by flash column chromatography (20%-50% ethyl acetate/hexanes) to provide 12.6 g (35%) of 4-Methyl-2-(4-trifluoromethyl-phenyl)-oxazole-5-carboxylic acid methyl ester. This ester (2.0 g, 7.0 mmol) is reduced to the alcohol by dissolution in THF (50 mL) and adding 4 eq. LiBH$_4$ (0.610 g, 28.0 mmol) to provide 1.8 g (100%) [4-Methyl-2-(4-trifluoromethyl-phenyl)-oxazol-5-yl]-methanol. MS M$^+$+1 258.

Preparation 62

2-[5-Ethyl-2-(4-trifluoromethyl-phenyl)-thiazol-4-yl]-ethanol

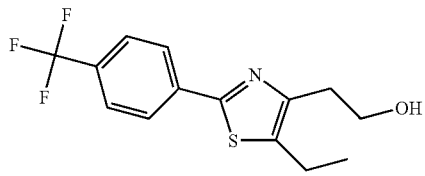

Preparation 63

2-[5-Propyl-2-(4-trifluoromethyl-phenyl)-thiazol-4-yl]-ethanol

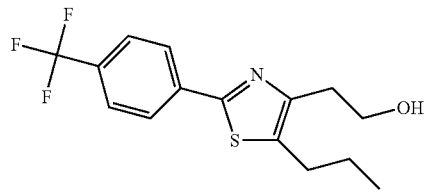

Preparation 64

Toluene-4-sulfonic acid 2-[5-propyl-2-(4-trifluoromethyl-phenyl)-thiazol-4-yl]-ethyl ester

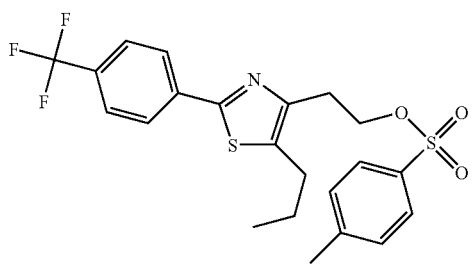

Step A

3-Oxo-heptanoic acid methyl ester (25 g, 0.157 Mol) is dissolved into anhydrous dichloromethane (DCM) (200 mL) and then cooled to 0° C.-5° C. while stirring. A solution of bromine (25.25 g, 0.160 Mol) in DCM (50 mL) is added dropwise over 2 h. to the solution of the beta keto-ester. After the addition, the mixture is allowed to stir 0.5 h. at 0° C., then the ice bath is removed and the mixture is allowed to stir at room temperature for 18 h. TLC will show complete consumtion of starting material, then ice water (200 g) is added with stirring. The organic layer is collected and washed with cold water (2×) and brine. The filtered solution is dried over anhydrous sodium sulfate, then concentrated to a clear liquid. The crude 4-Bromo-3-oxo-heptanoic acid methyl ester (31.5 g, 0.135 Mol), 86% yield, is used without further purification.

Step B

4-Bromo-3-oxo-heptanoic acid methyl ester (6.0 g, 25.0 mmol) is dissolved into denatured ethanol (100 mL) and para-trifluoromethyl thiobenzamide (5.0 g, 24.4 mmol) is added in one portion. The reaction is purged of air and flushed with nitrogen then heated to reflux. The reaction is monitored by TLC and HPLC and when complete, the reaction is allowed to cool to room temperature. The solvent is removed and the reaction is diluted with ethyl acetate (200 mL), followed by ishes with saturated sodium bicarbonate solution, water, and brine. The ethyl acetate solution is dried over anhydrous sodium sulfate, then concentrated add further purified using flash column chromatography (10% EtOAc/Hexanes) to yield pure [[5-Propyl-2-(4-trifluoromethyl-phenyl)-thiazol-4-yl]-acetic acid methyl ester (8.66 g, 24.2 mmol) or 98% yield.

Step C

[[5-Propyl-2-(4-trifluoromethyl-phenyl)-thiazol-4-yl]-acetic acid methyl ester (8.66 g, 24.2 mmol) is dissolved into anhydrous tetrahydrofuran (THF) (100 mL) and then cooled to 0° C. with stirring. Lithium aluminum hydride (24.2 mL, 1M in THF, 24.2 mmol) is slowly added by syringe and the reaction is monitored by TLC. Upon complete conversion, the reaction is carefully quenched using water, base, and water. Celite is added to the reaction, followed by diethyl ether and the mixture is then filtered through a celite plug. The two phases are then separated and the organic layer is washed using water and brine. The organic layer is the dried over anhydrous sodium sulfate and concentrated. The pure 2-[5-Propyl-2-(4-trifluoromethyl-phenyl)-thiazol-4-yl]-ethanol (5.739 g, 18.2 mmol) is obtained in 75% yield after flash column chromatography.

Step D

The 2-[5-Propyl-2-(4-trifluoromethyl-phenyl)-thiazol-4-yl]-ethanol (5.739 g, 18.2 mmol) is dissolved into anhydrous dichloromethane (DCM) (100 mL) and dimethylamino pyridine (0.670 g, 5.46 mmol), tosic anhydride (11.9 g, 36.4 mmol), and pyridine (5 mL, 64 mmol) are added at room temperature. The reaction is monitored by TLC, and upon complete consumption of the starting alcohol, the reaction is diluted with DCM and extracted against saturated sodium bicarbonate solution. The organic layer is washed with water and brine, then dried over anhydrous sodium sulfate and concentrated. The pure Toluene-4-sulfonic acid 2-[5-propyl-2-(4-trifluoromethyl-phenyl)-thiazol-4-yl]-ethyl ester (4.46 g, 9.5 mmol) is obtained after flash column chromatography.

The following compounds are prepared in a similar manner:

Preparation 65

Toluene-4-sulfonic acid 2-[5-ethyl-2-(4-trifluoromethyl-phenyl)-thiazol-4-yl]-ethyl ester

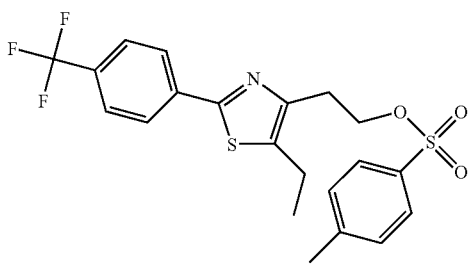

Preparation 66

Toluene-4-sulfonic acid 2-[2-(2-chloro-phenyl)-5-ethyl-thiazol-4-yl]-ethyl ester

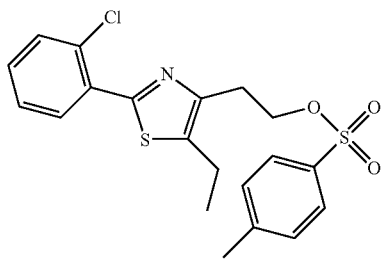

Preparation 67

2-(4-Hydroxy-2-methyl-phenoxy)-2-methyl-propionic acid

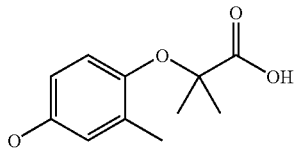

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339-346) (2.28 g, 10.0 mmol), ethyl bromoisobutyrate (2.2 mL, 15 mmol), and cesium carbonate (3.26 g, 10.0 mmol) in dry DMF (25 mL) are heated at 80° C. for 18 h. The reaction mixture is cooled and partitioned between water (30 mL) and ether (75 mL). The organic layer is washed with brine (15 mL). The aqueous layers are back-extracted with ethyl acetate (30 mL), and the organic layer is washed with brine (20 mL). The combined organic layers are dried ($Na_2SO_4$) and concentrated to a brown oil. The crude product is purified by flash chromatography using hexanes:ethyl acetate (2.5:1) to give a pale yellow solid (3.04 g, 89%): mp 65° C.; $^1$H NMR (400 MHz, CDCl$_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B 2-(4-Hydroxy-2-methyl-phenoxy)-2-methyl-propionic acid ethyl ester 2-(4-Benzyloxy-2-formyl-phenoxy)-2-methyl-propionic acid ethyl ester (9.00 g, 26.3 mmol) in ethanol (250 mL) is treated with 5% Pd/C (1.25 g) and hydrogen (60 psi, rt, overnight). Additional 5% Pd/C (1.25 g) is added, and the reaction is continued for 6 h at 40° C. The mixture is filtered and concentrated to a tan oil (6.25 g). This oil contained 9 mol % of 2-(4-Hydroxy-2-hydroxymethyl-phenoxy)-2-methyl-propionic acid ethyl ester. $^1$H NMR (400 MHz, CDCl$_3$) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

The following compound is prepared in a similar manner:

Preparation 68

2-(4-Hydroxy-2-methyl-phenoxy)-acetic acid

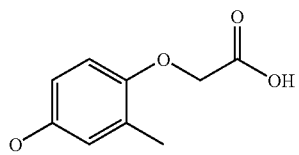

$^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Preparation 69

(4-Hydroxy-2-propyl-phenoxy)-acetic acid ethyl ester

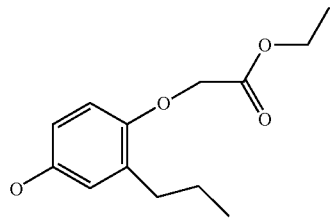

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) is treated with 5% Pd/C (0.25 g) and hydrogen (1 atm) at ambient temperature for 18 h. The mixture is filtered and concentrated. The crude product is purified on a Biotage medium pressure chromatography system using a 40 L normal phase cartridge and eluted with 10% ethyl acetate in hexanes to give a tan solid (2.8 g, 56%). Rf=0.33 (25% EtOAc/Hexanes); $^1$H NMR (400 MHz, CDCl$_3$) δ 7.44-7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B (4-Benzyloxy-2-propylphenoxy)acetic acid ethyl ester

A solution of 4-benzyloxy-2-propylphenol (0.50 g, 1.94 mmol) in dry DMF (7 mL) is cooled in an ice bath and treated with NaH (0.15 g, 3.8 mmol, 60% oil dispersion). The ice bath is removed, ethyl bromoacetate (0.43 mL, 3.9 mmol) is added, and the mixture is placed in an oil bath (T=85° C.). After 18 h, the reaction mixture is cooled and concentrated in vacuo. The residue is diluted with EtOAc, washed with brine (2×), dried (Na$_2$SO$_4$), and concentrated. The crude product is purified by radial chromatography using 10% ethyl acetate in hexanes to give a tan solid (0.62 g, 97%). $^1$H NMR (400 MHz, CDCl$_3$) δ 7.44-7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C (4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) is treated with 5% Pd/C (75 mg) and hydrogen (60 psi) at ambient temperature for 24 h. The mixture is filtered and concentrated. The crude product is purified by radial chromatography using 15% ethyl acetate in hexanes to give a tan solid (0.25 g, 57%). $^1$H NMR (400 MHz, CDCl$_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Preparation 70

(3-Bromo-4-hydroxy-phenoxy)-acetic acid ethyl ester

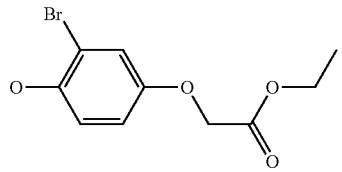

To a solution of (4-hydroxy-phenoxy)-acetic acid ethyl ester (0.59 g, 3 mmol) in acetic acid (1.5 mL) is added bromine (0.48 g, 9 mmol) in acetic acid (0.5 mL) at room temperature. After 5 min, solvent is evaporated and purified by column chromatography on silica gel giving the title compound (0.6 g).

Preparation 71

(4-Mercapto-phenoxy)-acetic acid ethyl ester

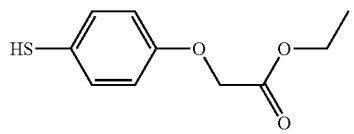

Step A (4-Chlorosulfonyl-phenoxy)-acetic acid ethyl ester

Phenoxy-acetic acid ethyl ester (9.1 mL) is added to chlorosulfonic acid (15 mL) at 0° C. dropwise. The reaction is stirred at 0° C. for 30 min, it is allowed to warm to room temperature. After 2 hrs, the reaction mixture is poured into ice, solid product is collected by filtration and dried under vacuum.

Step B (4-Mercapto-phenoxy)-acetic acid ethyl ester

To a mixture of (4-chlorosulfonyl-phenoxy)-acetic acid ethyl ester (0.98 g, 3.5 mmol) and tin powder (2.1 g) in ethanol (4.4 mL) is added HCl in dioxane (1.0 M, 4.4 mL) under nitrogen. The mixture is heated to reflux for 2 hrs, it is poured into ice and methylene chloride and filtered. The layers are separated and extracted with methylene chloride, dried and concentrated. The crude product is used for next step without purification.

The following compounds are made in a similar manner:

Preparation 72

(4-Mercapto-2-methyl-phenoxy)-acetic acid ethyl ester

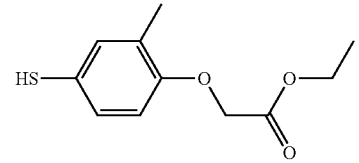

This compound can also be made by the following procedure: To a stirred suspension of Zn powder (10 μm, 78.16 g, 1.2 mol) and dichlorodimethyl silane (154.30 g, 145.02 mL, 1.2 mol) in 500 mL of dichloroethane is added a solution of (4-chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition is at a rate so as to maintain the internal temperature at ~52° C., cooling with chilled water as necessary. After addition is complete, the mixture is heated at 75° C. for 1 hour. It is then cooled to room temperature, filtered and concentrated iv. Add MTBE, washed twice with saturated LiCl solution concentrate iv again. Take up the residue in CH$_3$CN, ish with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yielded 61 g (79%) of a clear, colorless oil.

NMR (DMSO-d$_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Preparation 73

(4-Mercapto-2-propyl-phenoxy)-acetic acid ethyl ester

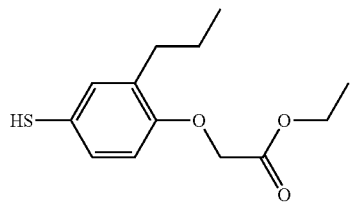

Preparation 74

3-(4-Mercapto-2-methyl-phenyl)-propionic acid methyl ester

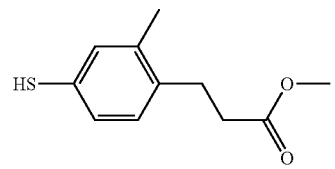

Step A

3-(4-Dimethylthiocarbamoyloxy-2-methyl-phenyl)-propionic acid methyl ester 3-(4-Hydroxy-2-methyl-phenyl)-propionic acid methyl ester (5.0 g, 25.75 mmol) is dissolved into dry dioxane (100 mL) and combined with 4-dimethylamino pyridine (0.500 g, 2.6 mmol), triethylamine (7.0 mL, 51.5 mmol), and dimethylaminothiocarbomoyl chloride (4.5 g, 32.17 mmol). The reaction is heated to reflux under nitrogen. The reaction is monitored by TLC until all of the phenol is consumed, 20 h. After cooling to room temperature, the reaction is diluted with ethyl acetate (200 mL). Water (75 mL) is added and the two layers are separated. The organic layer is washed with brine (75 mL) then dried over anhydrous sodium sulfate. The solvent is removed and the residue is dried under vacuum.

Step B

3-(4-Dimethylcarbamoylsulfanyl-2-methyl-phenyl)-propionic acid methyl ester 3-(4-Dimethylthiocarbamoyloxy-2-methyl-phenyl)-propionic acid methyl ester, taken crude from the previous step, is diluted with 75 mL of tetradecane and heated to reflux under nitrogen. The reaction is monitored by TLC until all the conversion is complete, 20 h. The reaction is allowed to cool to room temperature, then the tetradecane is decanted away from the resulting oil. The residue is rinsed several times with hexanes. This oil is then purified using flash column chromatography, yielding 5.01 g, or 69% (2 steps) of the product.

Step C

3-(4-Mercapto-2-methyl-phenyl)-propionic acid methyl ester 3-(4-Dimethylcarbamoylsulfanyl-2-methyl-phenyl)-propionic acid methyl ester (5.01 g, 17.8 mmol) is diluted with methanol (30 mL) and to this is added sodium methoxide (1.7 mL of 4M in methanol, 7.23 mmol). The reaction is heated to reflux under nitrogen and monitored by TLC. After complete conversion, 20 h., the reaction is allowed to cool to room temperature. The reaction is neutralized with 1N HCl (7.23 mL) and diluted with ethyl acetate (150 mL). The two phases are separated and the organic layer is washed with water (75 mL), then brine (75 mL). The organic layer is then dried over anhydrous sodium sulfate, then concentrated to yield 4.43 g crude product that is used without further purification.

Preparation 75

4-(2-Methoxycarbonyl-ethyl)-3-methyl-benzoic acid

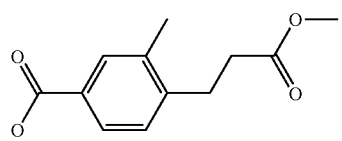

Step A

4-Bromo-3-methyl-benzoic acid benzyl ester

To a solution of 4-Bromo-3-methyl-benzoic acid benzyl (25.3 g, 0.118 mol) in DMF (200 mL) is added Cs2CO3 (76.6 g, 0.235 mol), followed by benzyl bromide (15.4 mL). After stirred at room temperature for 2 h, the reaction mixture is diluted with ethyl acetate, filtered through celite. The filtrate is washed with water and brine, dried over sodium sulfate, concentration gave the title product.

Step B

4-(2-Methoxycarbonyl-vinyl)-3-methyl-benzoic acid benzyl ester

To a solution of 4-bromo-3-methyl-benzoic acid benzyl ester (36 g, 118 mmol) in propronitrile (1000 mL) is added methyl acrylate (43.3 mL) and diisopropylethyl amine (42 mL), the solution is degassed and filled with nitrogen for three times. To this mixture are added tri-o-tolyl-phosphane (14.5 g) and palladium acetate (5.34 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate gave the title compound (31 g, 84.7%).

Step C

4-(2-Methoxycarbonyl-ethyl)-3-methyl-benzoic acid

A mixture of 4-(2-methoxycarbonyl-vinyl)-3-methyl-benzoic acid benzyl ester (11.6 g, 37.4 mmol) and Pd/C (5%, 1.5 g) in THF (300 mL) and methanol (100 mL) is stirred under 60 psi of hydrogen overnight. Catalyst is filtered off, filtrate is concentrated giving the title compound (8.3 g, 100%).

Preparation 76

(4-Hydroxy-2-methyl-phenyl)-acetic acid methyl ester

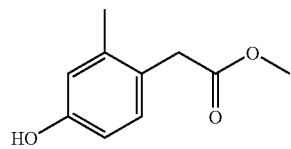

Step A

4-Methoxy-2-methylbenzoic acid (2.5 g, 15.04 mmol) is stirred in thionyl chloride (50 mL) at reflux 2 hr. The mixture is concentrated and diluted with toluene (10 mL) and concentrated. The resulting solid is dried under vacuum 18 hr. The resulting acid chloride is stirred in 20 mL ether at 0 deg C. A solution of diazomethane (39.6 mmol) in ether (150 mL) is added to the acid chloride solution and stirred 18 hr. The resulting diazoketone solution is concentrated. The residue is stirred in methanol (100 mL) and a solution of silver benzoate in triethylamine (1.0 g in 10 mL) is added and the reaction is heated to 60 deg C. and stirred 1 hr. The mixture is concentrated, diluted with 1.0 N aqueous hydrochloric acid (20 mL), extracted to three portions of ethyl acetate (50 mL each). The extracts are combined, washed with aqueous saturated sodium hydrogen carbonate, water, and brine (50 mL each), dried over anhydrous magnesium sulfate, filtered and concentrated. The residue is purified via silica gel chromatography eluting with 9:1 hexanes:ethyl acetate to afford 1.5 g (51%) of the homologated ester as a white solid.

Step B (4-Methoxy-2-methyl-phenyl)-acetic acid methyl ester (1.5 g, 7.72 mmol) is stirred in dichloromethane (50 mL) at 0 deg. C. Aluminum chloride (4.13 g, 31 mmol) is added followed by ethane thiol (2.9 mL, 38.6 mmol). The resulting mixture is stirred at room temperature for 2 hr. Water (50 mL) is added and the product is extracted into ethyl acetate (3×50 ml), the extracts are combined, dried over anhydrous magnesium sulfate, filtered, and concentrated to afford the title compound as a colorless oil, 1.4 g, 100%. MS $M^+ + 1$ 181. The structure is confirmed by $^1H$ NMR spectroscopy.

Preparation 77

(3-Hydroxy-phenyl)-acetic acid methyl ester

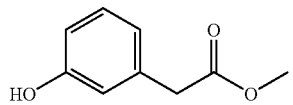

Step A (3-Hydroxy-phenyl)-acetic acid methyl ester (3-Hydroxy-phenyl)-acetic acid (5.0 g, 32.86 mmol) is stirred in methanol (100 mL) and concentrated (98%) sulfuric acid (3.0 mL) is added. The mixture is heated to reflux 18 hr. The reaction is cooled and concentrated. The residue is diluted with water (100 mL) and extracted with ethyl acetate (3×50 mL). The combined extracts are dried over anhydrous magnesium sulfate, filtered, and concentrated to yield the title compound as an orange oil, 5.46 g, 100%. MS $M^+ + 1$ 167. The structure is confirmed by $^1H$ NMR spectroscopy.

The following compounds are made in a similar manner:

Preparation 78

(3-Hydroxy-4-methoxy-phenyl)-acetic acid methyl ester

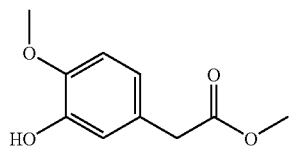

An orange oil. MS $M^+ + 1$ 197. The structure is confirmed by $^1H$ NMR spectroscopy.

Preparation 79

3-(3-Hydroxy-phenyl)-propionic acid methyl ester

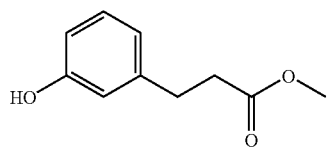

Step A 3-(3-Hydroxy-phenyl)-propionic acid methyl ester

An orange oil. MS $M^+ + 1$ 181. The structure is confirmed by $^1H$ NMR spectroscopy.

Preparation 80

(3-Mercapto-phenyl)-acetic acid methyl ester

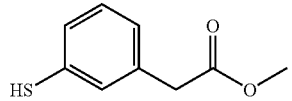

Step A

(3-Dimethylthiocarbamoyloxy-phenyl)-acetic acid methyl ester

A mixture of (3-Hydroxy-phenyl)-acetic acid methyl ester (5.5 g, 33.1 mmol), N,N-dimethyl thiocarbamoyl chloride (5.11 g, 41.38 mmol), triethylamine (9.2 mL, 66.2 mmol), N,N-dimethylamino pyridine (0.4 g, 3.31 mmol) and dioxane (50 mL) is stirred at reflux 18 hr. The mixture is concentrated, partioned between 1M aqueous hydrochloric acid (200 mL) and ethyl acetate (3×75 mL). The combined organic extracts are dried over anhydrous magnesium sulfate, filtered, concentrated, and purified via silica chromatography eluting the product with dichloromethane to afford the title compound as a brown oil, 6.8 g, 81%. MS M$^+$+1 254. The structure is confirmed by $^1$H NMR spectroscopy.

Step B

(3-Dimethylcarbamoylsulfanyl-phenyl)-acetic acid methyl ester (3-Dimethylthiocarbamoyloxy-phenyl)-acetic acid methyl ester (6.8 g, 26.84 mmol) is stirred in tetradecane (30 mL) at 255 deg C. for 8 hr. The mixture is cooled, the residue is purified by silica chromatography eluting the product with hexanes to 1:1 hexanes:ethyl acetate to afford the title compound as an orange oil, 4.9 g, 58%. MS M$^+$+1 254. The structure is confirmed by $^1$H NMR spectroscopy.

Step C

(3-Mercapto-phenyl)-acetic acid methyl ester

A mixture of (3-dimethylcarbamoylsulfanyl-phenyl)-acetic acid methyl ester (2.0 g, 7.9 mmol), potassium hydroxide (1.4 g, 24 mmol) methanol (50 mL), and water (5 mL) is stirred at reflux 3 hr. The mixture is concentrated, and product partitioned between 1M aqueous hydrochloric acid (50 mL) and ethyl acetate (3×75 mL). The combined extracts are dried over anhydrous magnesium sulfate, filtered and concentrated. The residue is taken up in methanol (50 mL), 2 mL concentrated sulfuric acid is added, and the mixture refluxed 3 hr. The mixture is concentrated, and the residue purified by silica chromatography eluting with 7:3 hexanes:ethyl acetate to afford the title compound as a pale yellow oil, 1.0 g, 69%. MS M$^+$+1 183. The structure is confirmed by $^1$H NMR spectroscopy.

Preparation 81

3-(4-Iodomethyl-2-methyl-phenyl)-propionic acid methyl ester

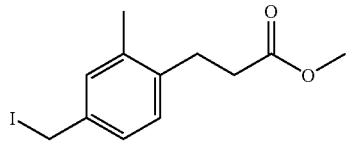

Step A

3-(4-Hydroxymethyl-2-methyl-phenyl)-acrylic acid methyl ester

A mixture of methyl-4-bromo-3-methylbenzoate (5.7 g, 24.88 mmol), lithium aluminum hydride (29 mL, 29 mmol, 1 M solution in tetrahydrofuran) and tetrahydrofuran (100 mL) is stirred in ice/water for 1 hr. The reaction is quenched with aqueous hydrochloric acid (50 mL, 1 M). The product is extracted into ethyl acetate (3×100 mL). The combined extracts are dried over anhydrous magnesium sulfate, filtered and concentrated. The crude product is taken up in propionitrile (100 mL). Methylacrylate (10 mL, 121.5 mmol), palladium acetate (1.12 g, 5 mmol), tri-o-tolylphosphine (3.0 g, 10 mmol), and N,N-diisopropyl ethylamine (8.7 mL, 50 mmol) are sequentially added and the resulting reaction mixture is heated to 110 deg C. 3 hr. The mixture is concentrated, and the residue diluted with aqueous hydrochloric acid (100 mL, 1M). The product is extracted with dichloromethane (2×100 mL) and ethyl acetate (100 mL). The combined extracts are dried over anhydrous magnesium sulfate, filtered, concentrated, and purified via silica chromatography eluting with 7:3 hexanes:ethyl acetate to 1:1 hexanes:ethyl acetate to afford the pure product as a yellow oil, 4.7 g, 91%. MS M$^+$+1 207. The structure is confirmed by $^1$H NMR spectroscopy.

Step B

3-(4-Hydroxymethyl-2-methyl-phenyl)-propionic acid methyl ester

A mixture of 3-(4-Hydroxymethyl-2-methyl-phenyl)-acrylic acid methyl ester (4.7 g, 22.8 mmol), Raney nickel (0.668 g) and tetrahydrofuran (618 mL) is shaken under 60 psig. Hydrogen 24 hr. The catalyst is filtered off, and the mixture is concentrated to afford the product as a pale yellow oil, 4.3 g, 91%. The structure is confirmed by $^1$H NMR spectroscopy.

Step C

3-(4-Iodomethyl-2-methyl-phenyl)-propionic acid methyl ester

A mixture of 3-(4-Hydroxymethyl-2-methyl-phenyl)-propionic acid methyl ester (0.62 g, 2.98 mmol), triphenyl phosphine (0.86 g, 3.27 mmol) and dichloromethane (10 mL) is stirred at room temperature. A solution of iodine (0.83 g, 3.27 mmol) in benzene (5 mL) is added and the black mixture is stirred at room temperature 2 hr. The brown mixture is diluted with 10% aqueous sodium hydrogen sulfite (5 mL) and the resulting clear mixture is washed with ethyl acetate (3×50 mL). The combined extracts are dried over anhydrous magnesium sulfate, filtered and concentrated. The residue is purified via silica chromatography eluting with 9:1 hexanes:ethyl acetate to afford the title compound as a crystalline ivory solid, 0.68 g, 72%. MS $M^++1$ 319. The structure is confirmed by $^1H$ NMR spectroscopy.

Preparation 82

(4-Bromo-2-methyl-phenoxy)-acetic acid methyl ester

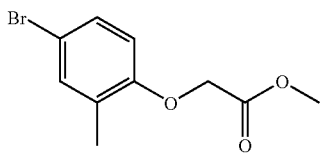

Step A (4-Bromo-2-methyl-phenoxy)-acetic acid methyl ester

A mixture of 4-bromo-2-methylphenol (1.0 g, 5.35 mmol), sodium hydride (0.26 g, 6.42 mmol, 60% mineral oil), N,N-dimethylformamide (10 mL), and methyl-2-bromoacetate (0.56 mL, 5.88 mmol) is stirred at room temperature 18 hr. The mixture is diluted with water (50 mL) and the product extracted to ethyl acetate (3×50 mL). The combined extracts are dried over anhydrous magnesium sulfate, filtered, concentrated and purified via silica chromatography eluting with 8:2 hexanes:ethyl acetate to afford title compound as a colorless oil, 1.03 g, 74%. MS $M^+$ 259. The structure is confirmed by $^1H$ NMR spectroscopy.

Preparation 83

3-(4-Amino-2-methyl-phenyl)-propionic acid methyl ester

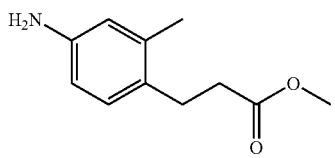

Step A 3-(2-Methyl-4-nitro-phenyl)-acrylic acid methyl ester

To a solution of 2-bromo-5-nitrotoluene (3.11 g, 14.39 mmol) in propionitrile (105 mL) is added DIPEA (5.1 mL, 29.28 mmol). The mixture is degassed three times. Methyl acrylate (5.2 mL, 57.74 mmol) is added and the mixture is degassed. Tri-o-tolylphosphine (1.77 g, 5.82 mmol) and $Pd(OAc)_2$ (0.64 g, 2.85 mmol) are added and the mixture is degassed a final two times followed by heating at 110° C. for 4 h. Upon cooling, the mixture is passed through Celite and the filtrate is concentrated. The residue is partitioned between $Et_2O$ and 1N HCl. The organics are washed with saturated $NaHCO_3$ and brine, and dried with $Na_2SO_4$. The crude material is purified by flash chromatography to yield the title compound (2.90 g, 91%).

Step B 3-(4-Amino-2-methyl-phenyl)-propionic acid methyl ester

A mixture of 3-(2-Methyl-4-nitro-phenyl)-acrylic acid methyl ester (1.47 g, 6.64 mmol) and 5% Pd/C (0.29 g) in MeOH (100 mL) is exposed to a hydrogen atmosphere (60 psi) for 12 h. The mixture is filtered through Celite and purified by flash chromatography to yield the title compound (0.99 g, 77%).

Preparation 84

3-(2-Methyl-4-methylaminomethyl-phenyl)-propionic acid methyl ester TFA salt

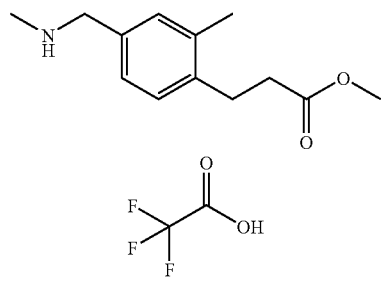

Step A 3-(4-Formyl-2-methyl-phenyl)-propionic acid methyl ester

A mixture of 3-(4-Hydroxymethyl-2-methyl-phenyl)-propionic acid methyl ester (0.49 g, 2.35 mmol) and $MnO_2$ (0.80 g, 9.20 mmol) in chloroform (5 mL) is stirred at RT for 4 days. The mixture is filtered through Celite; the Celite is washed with copious amounts of EtOAc. The filtrate is concentrated and purified by flash chromatography to yield the title compound (0.29 g, 60%).

Step B 3-(2-Methyl-4-methylaminomethyl-phenyl)-propionic acid methyl ester trifluoroacetic acid To a mixture of 3-(4-Formyl-2-methyl-phenyl)-propionic acid methyl ester (0.27 g, 1.31 mmol) and methylamine (2M in THF, 0.60 mL, 1.20 mmol) in anhydrous $CH_2Cl_2$ (10 mL) is added 4 Å molecular sieves followed by acetic acid (0.090 mL, 1.57 mmol). The mixture is stirred at RT for 1.5 h. Sodium triacetoxyborohydride (0.39 g, 1.85 mmol) is added, and the mixture is stirred overnight. The reaction is quenched with saturated NaHCO$_3$. The organics are washed with saturated NaHCO$_3$ and brine, and dried with MgSO$_4$. Upon concentration, the mixture is purified by reverse phase chromatography to yield the title compound (0.12 g, 45%).

Preparation 85

3-(4-Aminomethyl-2-methyl-phenyl)-propionic acid methyl ester

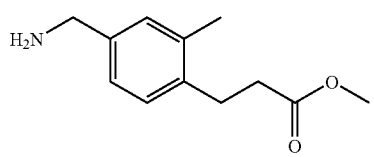

Step A 3-(4-Chloromethyl-2-methyl-phenyl)-propionic acid methyl ester

To a 0° C. solution of 3-(4-Hydroxymethyl-2-methyl-phenyl)-propionic acid methyl ester (1.02 g, 4.90 mmol) in anhydrous CH$_2$Cl$_2$ (15 mL) is added triethylamine (0.75 mL, 5.38 mmol) followed by thionyl chloride (0.40 mL, 5.48 mmol). The mixture is allowed to warm to RT overnight. Water is added, and the mixture is extracted with CH$_2$Cl$_2$. The organics are dried with MgSO$_4$ and concentrated. The crude material is purified by flash chromatography to yield the title compound (1.01 g, 91%).

Step B 3-(4-Azidomethyl-2-methyl-phenyl)-propionic acid methyl ester

To a solution of 3-(4-Chloromethyl-2-methyl-phenyl)-propionic acid methyl ester (0.52 g, 2.31 mmol) in DMF (7 mL) is added sodium azide (0.25 g, 3.84 mmol). The mixture is stirred overnight. Water is added, and the mixture is extracted with EtOAc. The organics are dried with Na$_2$SO$_4$ and concentrated to yield the title compound (0.49 g, 91%). The material is used without further purification.

Step C 3-(4-Aminomethyl-2-methyl-phenyl)-propionic acid methyl ester

A mixture of 3-(4-Azidomethyl-2-methyl-phenyl)-propionic acid methyl ester (0.20 g, 0.86 mmol) and 5% Pd/C (32 mg) in EtOH (50 mL) is exposed to a hydrogen atmosphere (60 psi) at RT overnight. Upon filtering the mixture through Celite, the filtrate is concentrated to yield the title compound (0.14 g, 78%). The material is used without further purification.

Preparation 86

4-Isopropyl-2-(4-trifluoromethyl-phenyl)-thiazole-5-carboxylic acid

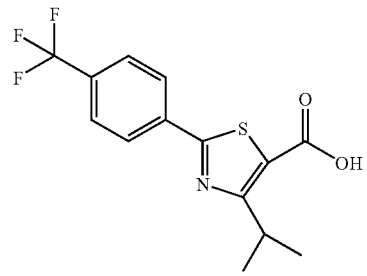

To a solution of 4-isopropyl-2-(4-trifluoromethyl-phenyl)-thiazole-5-carboxylic acid ethyl ester (0.62 g, 1.80 mmol) in THF (10 mL) is added 5M NaOH (3.5 mL, 17.50 mmol). The mixture is heated at 70° C. for 12 h. Upon cooling to RT, the mixture is acidified with 5M HCl and extracted with EtOAc. The organics are washed with water and brine, and dried with MgSO$_4$. After concentration, the title compound is obtained (0.46 g, 81%). The material is used without further purification.

The following compounds are made in a similar manner:

Preparation 87

[5-Ethyl-2-(4-trifluoromethyl-phenyl)-thiazol-4-yl] acetic acid

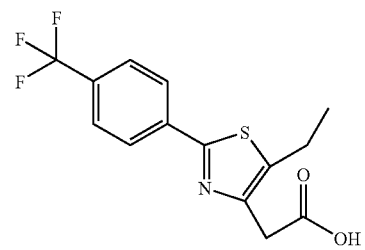

Preparation 88

[2-(6-Chloro-pyridin-3-yl)-5-methyl-oxazol-4-yl]-acetic acid methyl ester

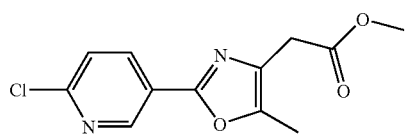

Step A

Aspartic acid methyl ester hydrochloride salt (57 g, 310 mmol) is dissolved in dichloromethane (500 mL) and cooled to 0° C. in an ice water bath. Triethylamine (75 mL, 444 mmol) is slowly added in several portions and the mixture is allowed to stir at 0° C. Meanwhile, 6-chloronicotinic acid (35 g, 222 mmol) is dissolved into dichloromethane (500 mL) with a drop of dimethylformamide and cooled to 0° C. in an ice water bath. After one hour at 0° C. the ice bath is removed and the solution allowed to warm to room temperature. The solvent is evaporated, the solution concentrated to about 100 mL, and then transferred to an addition funnel. This solution is then slowly added to the amino acid solution over two hours at 0° C. After two hours, the ice bath is removed. Upon reaching room temperature, the reaction is complete. The reaction is acidified with concentrated hydrochloric acid. The two phases are separated and the organic layer is washed with water and brine. The organic layer is then dried over anhydrous sodium sulfate, filtered, and concentrated. The white solid is used without further purification.

Step B

2-[(6-Chloro-pyridine-3-carbonyl)-amino]-succinic acid 4-methyl ester (222 mmol) is dissolved in ethyl acetate (300 mL) at room temperature and pyridine (90 mL, 1.11 mol), acetic anhydride (94 mL, 1.0 mol), and dimethyl amino pyridine (3.5 g, 22.2 mmol) are added. The reaction is heated to 90° C. under nitrogen. The reaction is monitored by HPLC and upon complete consumption of the starting material, is allowed to cool to room temperature. The reaction is diluted with additional ethyl acetate and the two phases are separated. The organic layer is washed a few times with 1N HCl, then saturated sodium bicarbonate solution, and finally brine. The organic layer is then dried over anhydrous sodium sulfate, filtered, and concentrated. The 3-[(6-Chloro-pyridine-3-carbonyl)-amino]-4-oxo-pentanoic acid methyl ester is used in the next step without further purification.

Step C

3-[(6-Chloro-pyridine-3-carbonyl)-amino]-4-oxo-pentanoic acid methyl ester is dissolved in acetic anhydride (75 mL) and concentrated sulfuric acid is added in 500 uL portions five times over a four hour period. The reaction is monitored by HPLC. The reaction is then heated to 40° C. until the starting material is consumed. The reaction is allowed to proceed at room temperature overnight. The reaction is then concentrated to dryness and purified by column chromatography. This procedure yielded (12.8 g, 48 mmol) 22% of the desired oxazole over four steps.

Preparation 89

[5-Methyl-2-(6-Phenylsulfanyl-pyridin-3-yl)-oxazol-4-yl]-acetic acid methyl ester

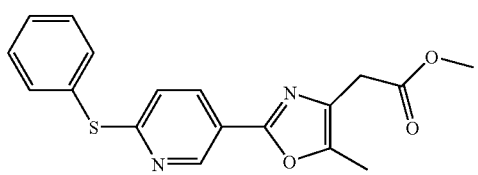

[2-(6-Chloro-pyridin-3-yl)-5-methyl-oxazol-4-yl]-acetic acid methyl ester (4.8 g, 17.98 mmol) is dissolved in anhydrous dimethylformamide (100 mL) and allowed to stir under nitrogen. Benzenethiol (2.78 mL, 27 mmol) is added by syringe, followed by anhydrous cesium carbonate (12.6 g, 36 mmol). The mixture is allowed to stir under nitrogen 50° C. and monitored by HPLC. After complete consumption of strating material, the solution is quenched with 1N sodium hydroxide solution, diluted with ethyl acetate, and then enough water added to dissolve the solids. The two phases are separated and the organic layer is washed with water and brine, dried over anhydrous sodium sulfate, filtered, and concentrated. The pure [5-Methyl-2-(6-phenyl-sulfanyl-pyridin-3-yl)-oxazol-4-yl]-acetic acid methyl ester (4.51 g, 13.2 mmol) is isolated in 74% yield after column chromatography.

The following compound is made in a similar manner:

Preparation 90

[5-Methyl-2-(6-phenylsulfanyl-pyridin-3-yl)-oxazol-4-yl]-acetic acid methyl ester

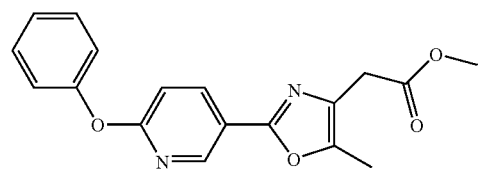

Example 1

{2-Methyl-4-[4-phenethyl-2-(4-trifluoromethyl-phenyl)-thiazol-5-ylmethylsulfanyl]-phenoxy}-acetic acid

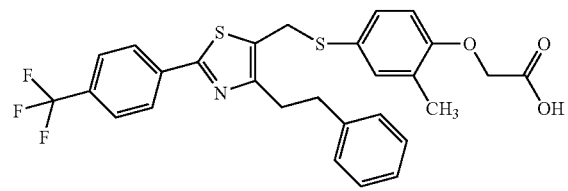

Step A

{2-Methyl-4-[4-phenethyl-2-(4-trifluoromethyl-phenyl)-thiazol-5-ylmethylsulfanyl]-phenoxy}-acetic acid ethyl ester To a solution of 5-chloromethyl-4-phenethyl-2-(4-trifluoromethyl-phenyl)-thiazole (190 mg, 0.5 mmol) and (4-Mercapto-2-methyl-phenoxy)-acetic acid ethyl ester (100 mg, 0.44 mmol) in acetonitrile (3 mL) is added Cs2CO3 (325 mg, 1 mmol). The mixture is stirred at room temperature over night, quenched by water, extracted with ethyl acetate, dried over sodium sulfate. Column chromatography on silica gel of the crude product gave 210 mg (83.5% yield) of the title compound.

Step B

{2-Methyl-4-[4-phenethyl-2-(4-trifluoromethyl-phenyl)-thiazol-5-ylmethylsulfanyl]-phenoxy}-acetic acid To a solution of {2-methyl-4-[4-phenethyl-2-(4-trifluoromethyl-phenyl)-thiazol-5-ylmethylsulfanyl]-phenoxy}-acetic acid ethyl ester (210 mg, 0.37 mmol) in THF (3 mL) is added LiOH (1.0 M, 2 mL). After stirred at room temperature for 2 hrs, it is acidified with 5 N HCl, extracted with ether, dried over sodium sulfate. Concentration gave the title compound (200 mg). MS (ES): 544.2 (M$^+$+1); the structure is also confirmed by $^1$H NMR.

The following compounds are made in a similar manner, all structures are confirmed by MS and proton NMR:

Example 2

{4-[4-Methyl-2-(4-trifluoromethyl-phenyl)-thiazol-5-ylmethylsulfanyl]-2-propyl-phenoxy}-acetic acid

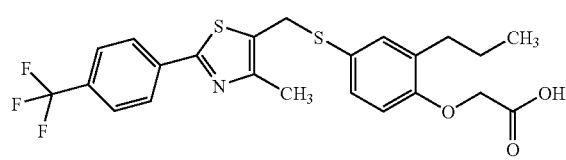

Example 3

{4-[4-Ethyl-2-(4-trifluoromethyl-phenyl)-thiazol-5-ylmethylsulfanyl]-2-methyl-phenoxy}-acetic acid

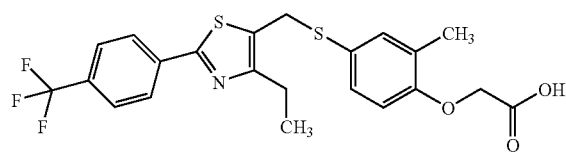

Example 4

{4-[4-Ethyl-2-(4-trifluoromethyl-phenyl)-thiazol-5-ylmethoxy]-2-methyl-phenoxy}-acetic acid

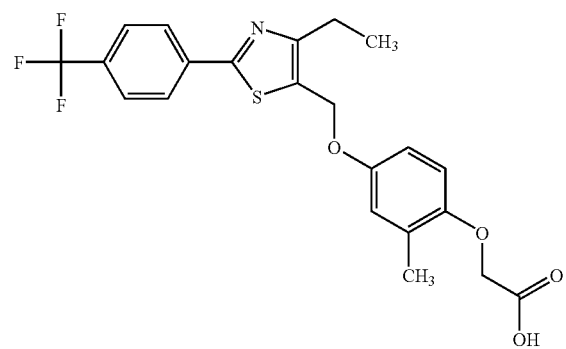

Example 5

3-{4-[4-Ethyl-2-(4-trifluoromethyl-phenyl)-thiazol-5-ylmethoxy]-2-methyl-phenyl}-propionic acid

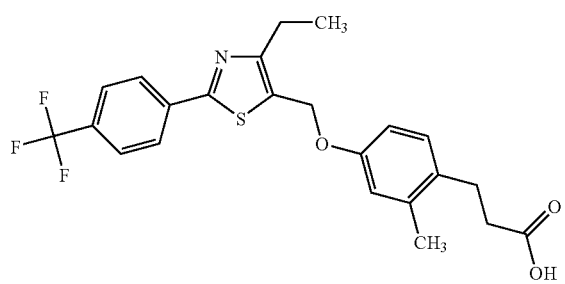

Example 6

{4-[4-Ethyl-2-(4-trifluoromethyl-phenyl)-thiazol-5-ylmethoxy]-2-propyl-phenoxy}-acetic acid

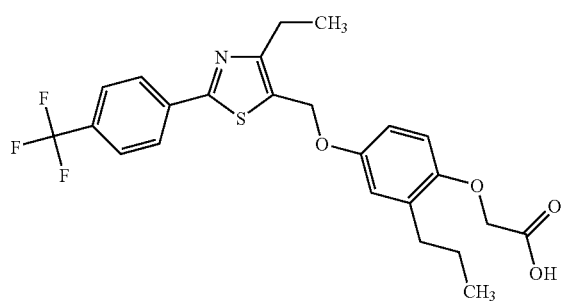

Example 7

{4-[4-Butyl-2-(4-trifluoromethyl-phenyl)-thiazol-5-ylmethylsulfanyl]-2-methyl-phenoxy}-acetic acid

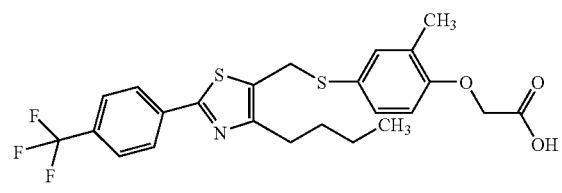

Example 8

2-{4-[4-Butyl-2-(4-trifluoromethyl-phenyl)-thiazol-5-ylmethoxy]-2-methyl-phenoxy}-2-methyl-propionic acid

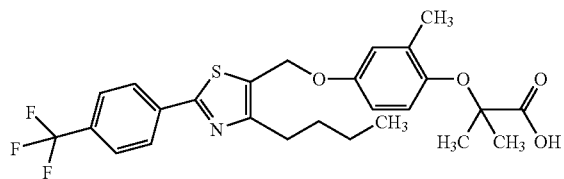

Example 9

{4-[4-Butyl-2-(4-trifluoromethyl-phenyl)-thiazol-5-ylmethoxy]-2-methyl-phenoxy}-acetic acid

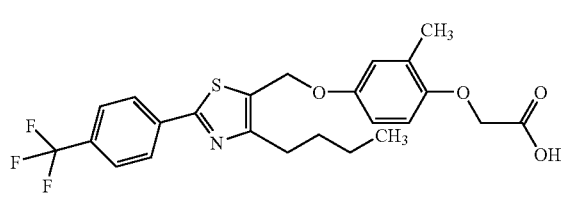

Example 10

3-{4-[4-Butyl-2-(4-trifluoromethyl-phenyl)-thiazol-5-ylmethoxy]-2-methyl-phenyl}-propionic acid

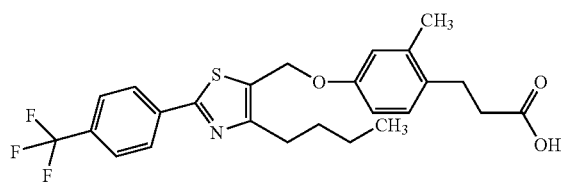

Example 11

3-{4-[4-Ethyl-2-(4-trifluoromethyl-phenyl)-thiazol-5-ylmethylsulfanyl]-2-methyl-phenyl}-propionic acid

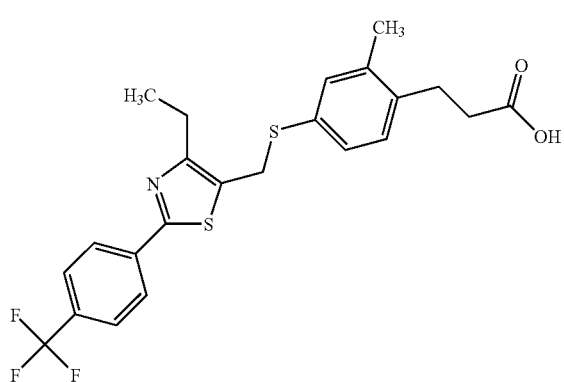

Example 12

{4-[4-(3,5-Bis-trifluoromethyl-phenoxymethyl)-2-(4-trifluoromethyl-phenyl)-thiazol-5-ylmethylsulfanyl]-2-methyl-phenoxy}-acetic acid

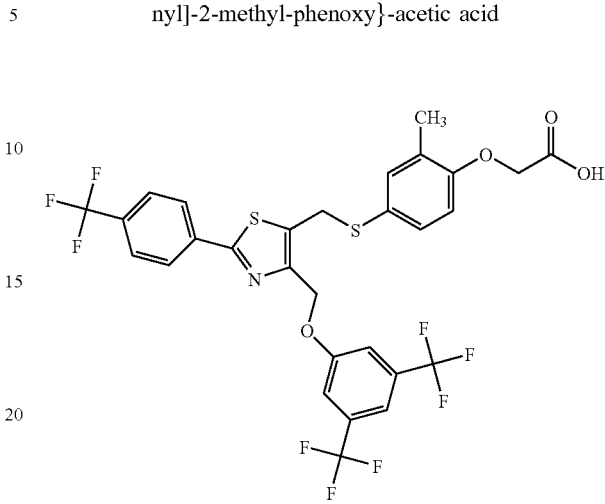

Example 13

{2-Methyl-4-[4-propyl-2-(4-trifluoromethyl-phenyl)-thiazol-5-ylmethylsulfanyl]-phenoxy}-acetic acid

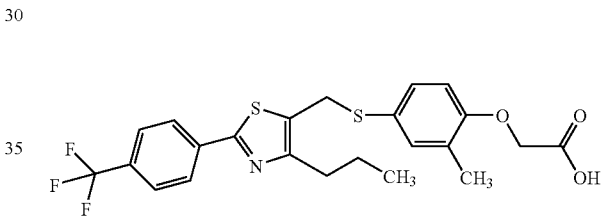

Example 14

{4-[4-Isopropyl-2-(4-trifluoromethyl-phenyl)-thiazol-5-ylmethylsulfanyl]-2-methyl-phenoxy}-acetic acid

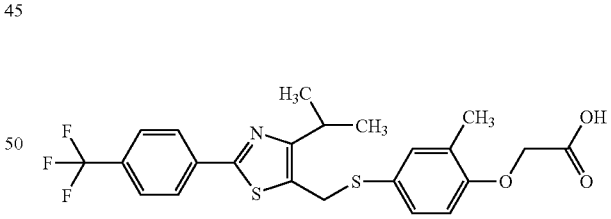

Example 15

{4-[4-But-3-enyl-2-(4-trifluoromethyl-phenyl)-thiazol-5-ylmethylsulfanyl]-2-methyl-phenoxy}-acetic acid

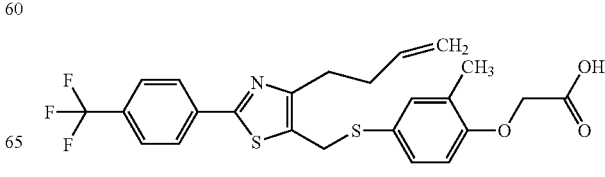

Example 16

3-{2-Methyl-4-[4-propyl-2-(4-trifluoromethyl-phenyl)-thiazol-5-ylmethylsulfanyl]-phenyl}-propionic acid

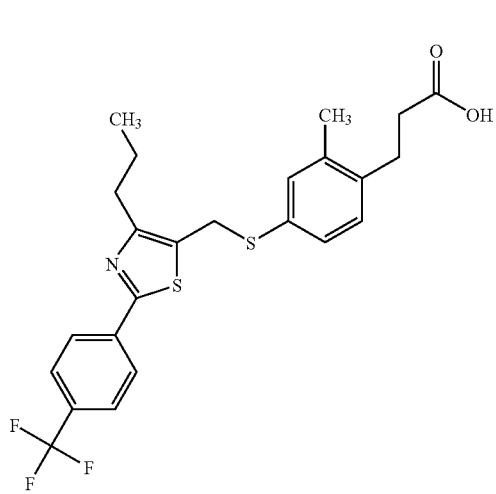

Example 17

3-{2-Methyl-4-[4-phenethyl-2-(4-trifluoromethyl-phenyl)-thiazol-5-ylmethylsulfanyl]-phenyl}-propionic acid

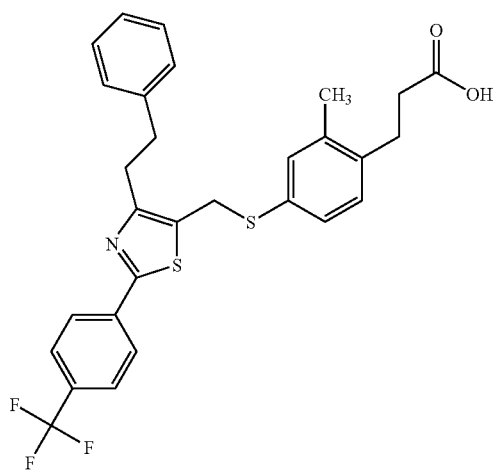

Example 18

3-{2-Methyl-4-[4-phenethyl-2-(4-trifluoromethyl-phenyl)-thiazol-5-ylmethoxy]-phenyl}-propionic acid

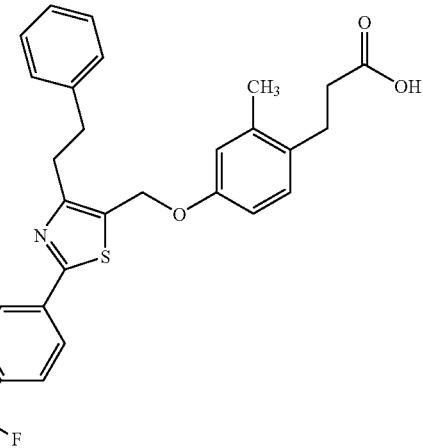

Example 19

3-{2-Methyl-4-[4-propyl-2-(4-trifluoromethyl-phenyl)-thiazol-5-ylmethoxyl]-phenyl}-propionic acid

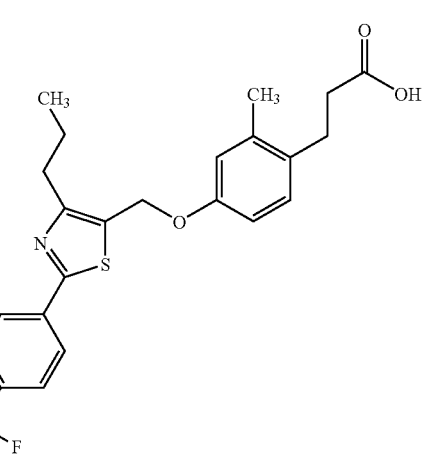

Example 20

3-{4-[4-Isopropyl-2-(4-trifluoromethyl-phenyl)-thiazol-5-ylmethoxy]-2-methyl-phenyl}-propionic acid

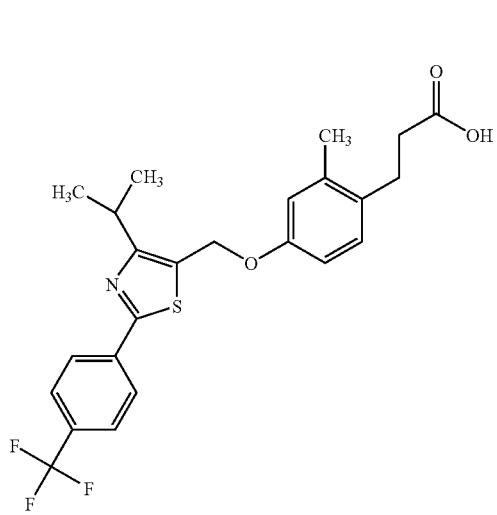

Example 21

{4-[4-(4-Bromo-phenylsulfanylmethyl)-2-(4-trifluoromethyl-phenyl)-thiazol-5-ylmethylsulfanyl]-2-methyl-phenoxy}-acetic acid

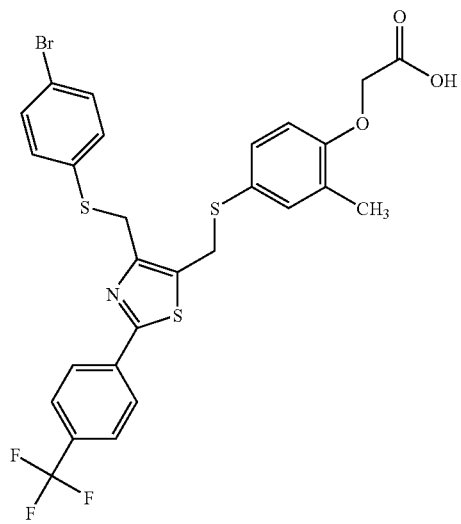

Example 22

{4-[4-tert-Butyl-2-(4-trifluoromethyl-phenyl)-thiazol-5-ylmethoxy]-2-methyl-phenoxy}-acetic acid

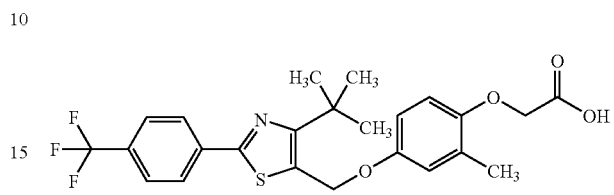

Example 23

{4-[4-tert-Butyl-2-(4-trifluoromethyl-phenyl)-thiazol-5-ylmethylsulfanyl]-2-methyl-phenoxy}-acetic acid

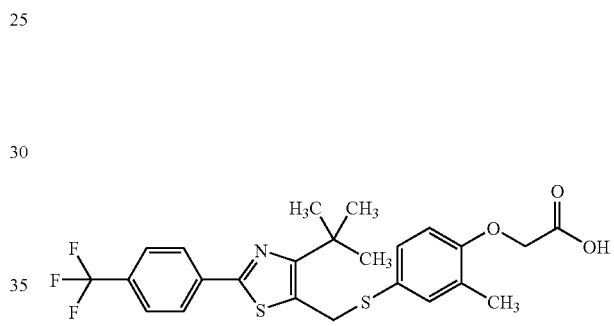

Example 24

-{4-[4-Isopropyl-2-(4-trifluoromethyl-phenyl)-thiazol-5-ylmethylsulfanyl]-2-methyl-phenyl}-propionic acid

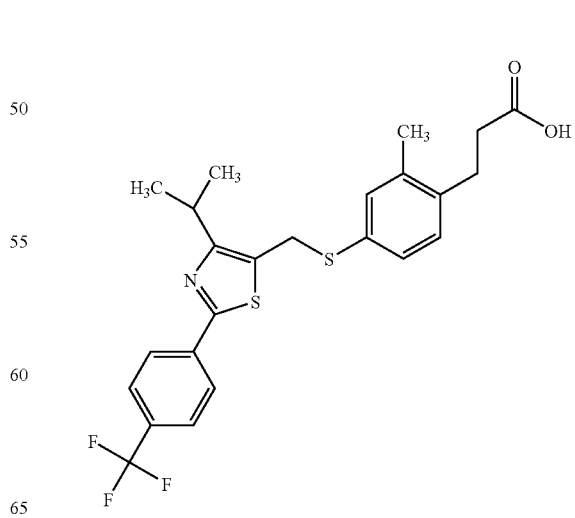

Example 25

{2-Methyl-4-[4-phenoxymethyl-2-(4-trifluoromethyl-phenyl)-thiazol-5-ylmethylsulfanyl]-phenoxy}-acetic acid

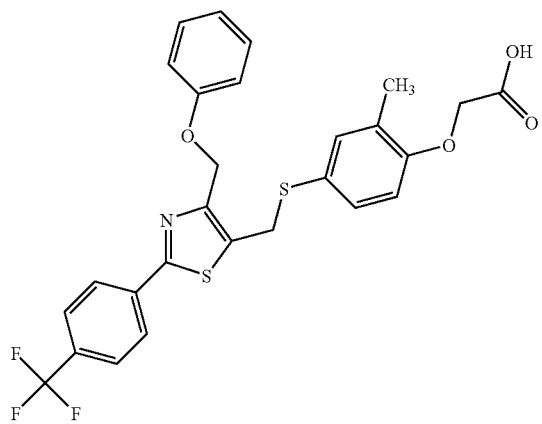

Example 26

{4-[4-[2-(2-Chloro-6-fluoro-phenyl)-ethyl]-2-(4-trifluoromethyl-phenyl)-thiazol-5-ylmethylsulfanyl]-2-methyl-phenoxy}-acetic acid

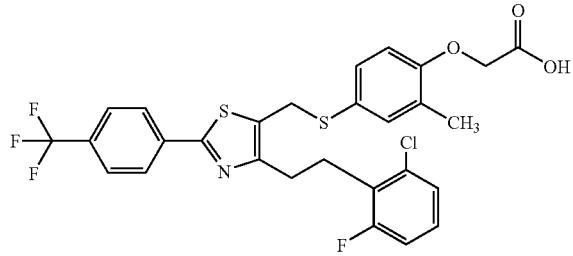

Example 27

{4-[4-[2-(2-Chloro-6-fluoro-Phenyl)-ethyl]-2-(4-trifluoromethyl-phenyl)-thiazol-5-ylmethoxy]-2-methyl-phenoxy}-acetic acid

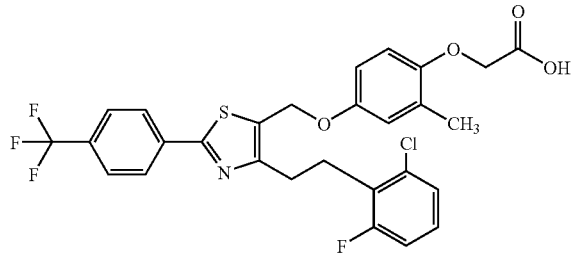

Example 28

3-{4-[4-[2-(2-Chloro-6-fluoro-phenyl)-ethyl]-2-(4-trifluoromethyl-phenyl)-thiazol-5-ylmethoxy]-2-methyl-phenyl}-propionic acid

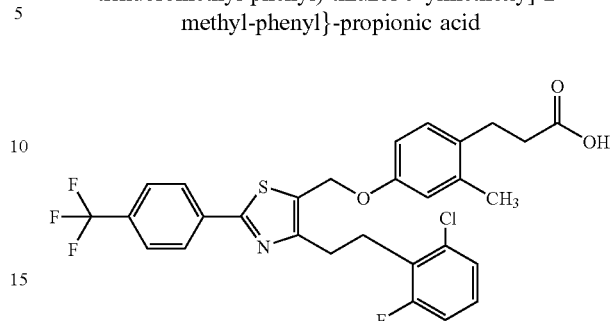

Example 29

{2-Methyl-4-[4-phenoxymethyl-2-(4-trifluoromethyl-phenyl)-thiazol-5-ylmethoxy]-phenoxy}-acetic acid

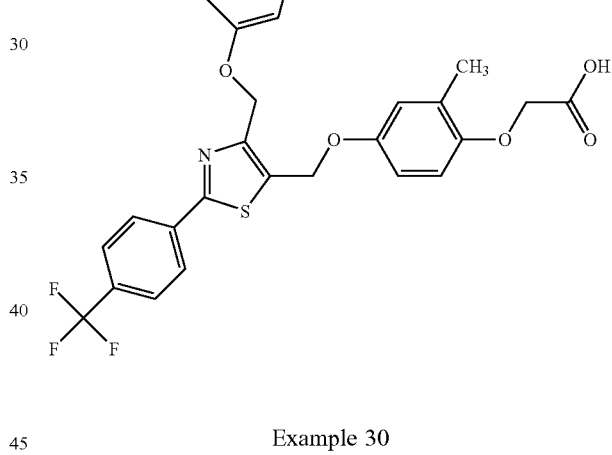

Example 30

3-{2-Methyl-4-[4-phenoxymethyl-2-(4-trifluoromethyl-phenyl)-thiazol-5-ylmethoxy]-phenyl}-propionic acid

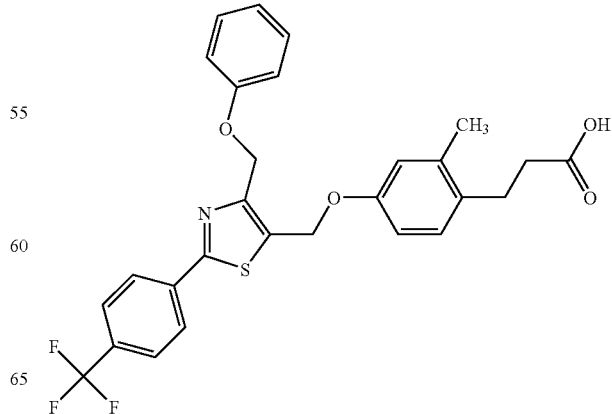

Example 31

{2-Methyl-4-[4-phenylsulfanylmethyl-2-(4-trifluoromethyl-phenyl)-thiazol-5-ylmethylsulfanyl]-phenoxy}-acetic acid

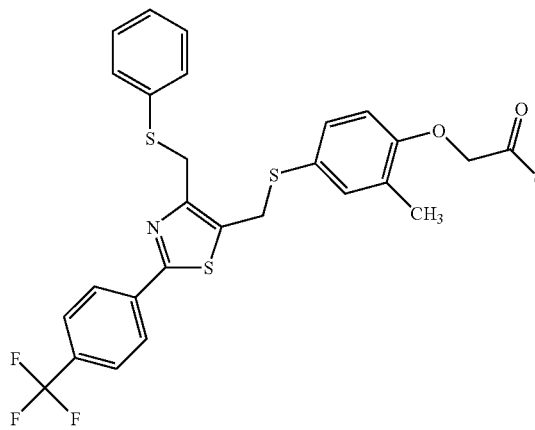

Example 32

3-{2-Methyl-4-[4-phenylsulfanylmethyl-2-(4-trifluoromethyl-phenyl)-thiazol-5-ylmethoxy]-phenyl}-propionic acid

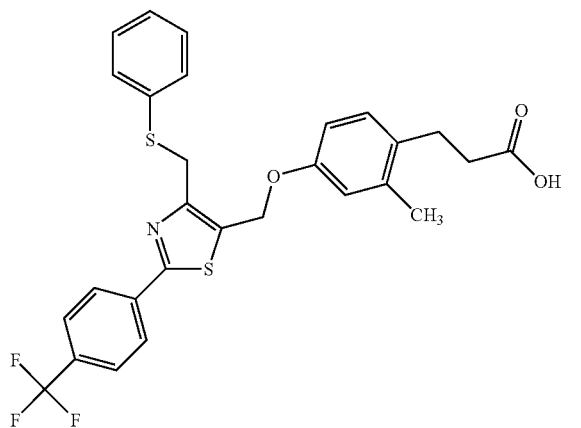

Example 33

{4-[4-(2-Chloro-6-fluoro-phenoxymethyl)-2-(4-trifluoromethyl-phenyl)-thiazol-5-ylmethylsulfanyl]-2-methyl-phenoxy}-acetic acid

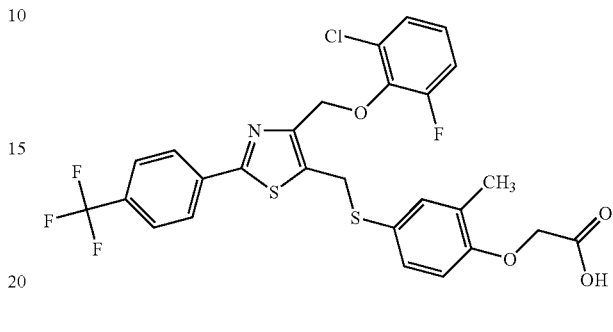

Example 34

3-{4-[4-(2-Chloro-6-fluoro-phenoxymethyl)-2-(4-trifluoromethyl-phenyl)-thiazol-5-ylmethoxy]-2-methyl-phenyl}-propionic acid

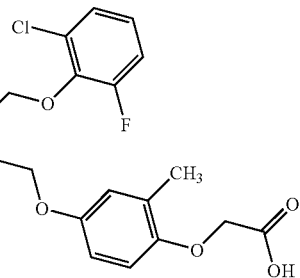

Example 35

{4-[4-(2-Chloro-6-fluoro-phenoxymethyl)-2-(4-trifluoromethyl-phenyl)-thiazol-5-ylmethoxy]-2-methyl-phenoxy}-acetic acid

Example 36

3-{4-[4-(3,5-Bis-trifluoromethyl-phenoxymethyl)-2-(4-trifluoromethyl-phenyl)-thiazol-5-ylmethoxy]-2-methyl-phenyl}-propionic acid

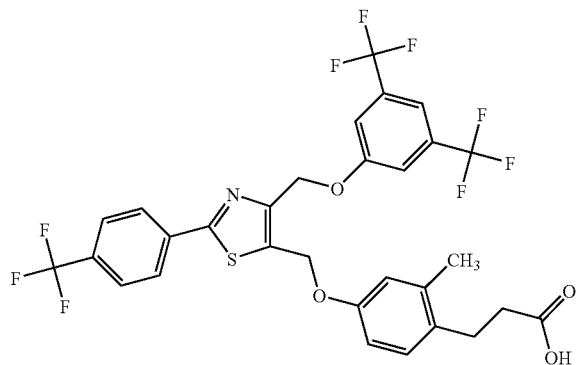

Example 37

{4-[4-(3,5-Bis-trifluoromethyl-phenoxymethyl)-2-(4-trifluoromethyl-phenyl)-thiazol-5-ylmethoxy]-2-methyl-phenoxy}-acetic acid

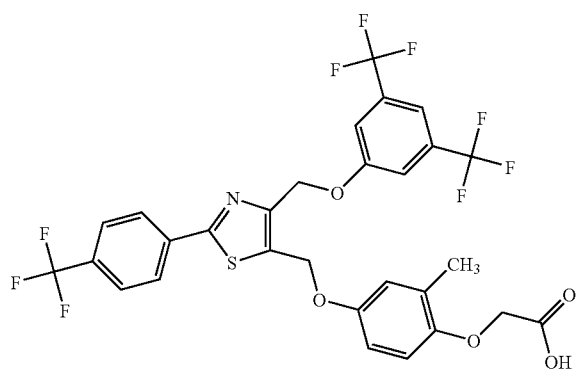

Example 38

3-{4-[4-Ethyl-2-(4-trifluoromethyl-phenyl)-thiazol-5-ylmethoxy]-phenyl}-2-methoxy-propionic acid

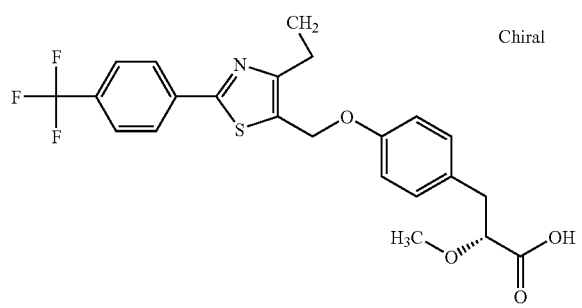

Chiral

Example 39

{3-Bromo-4-[4-ethyl-2-(4-trifluoromethyl-phenyl)-thiazol-5-ylmethoxy]-phenoxy}-acetic acid

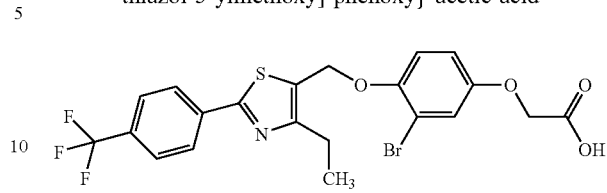

Example 40

2-{3-Bromo-4-[4-ethyl-2-(4-trifluoromethyl-phenyl)-thiazol-5-ylmethoxy]-phenoxy}-2-methyl-propionic acid

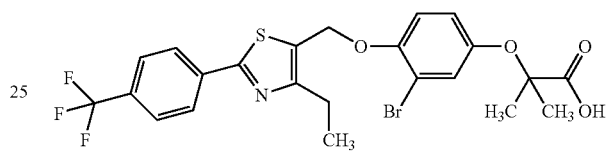

Example 41

3-{4-[4-Ethyl-2-(4-trifluoromethyl-phenyl)-thiazol-5-ylmethoxy]-2-methoxy-phenyl}-propionic acid

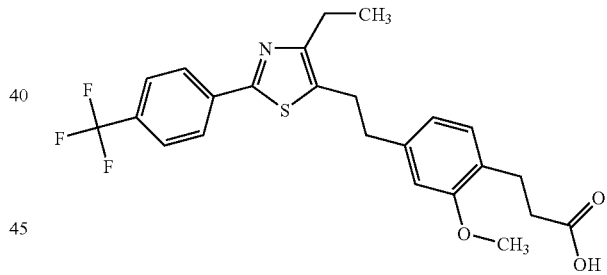

Example 42

{4-[4-Ethyl-2-(4-trifluoromethyl-phenyl)-thiazol-5-ylmethoxy]-phenoxy}-acetic acid

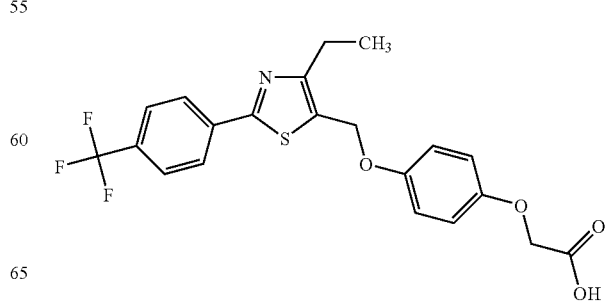

Example 43

3-{4-[4-Ethyl-2-(4-trifluoromethyl-phenyl)-thiazol-5-ylmethoxy]-phenyl}-propionic acid

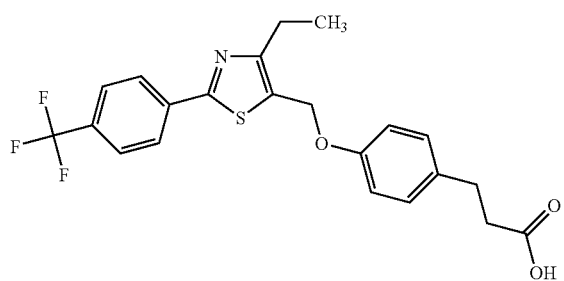

Example 44

(4-{2-[5-Ethyl-2-(4-trifluoromethyl-phenyl)-thiazol-4-yl]-ethylsulfanyl}-2-methyl-phenoxy)-acetic acid

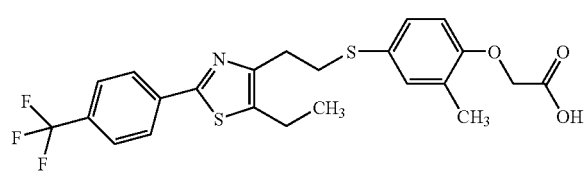

Example 45

3-{2-Methyl-4-[4-phenoxymethyl-2-(4-trifluoromethyl-phenyl)-thiazol-5-ylmethylsulfanyl]-phenyl}-propionic acid

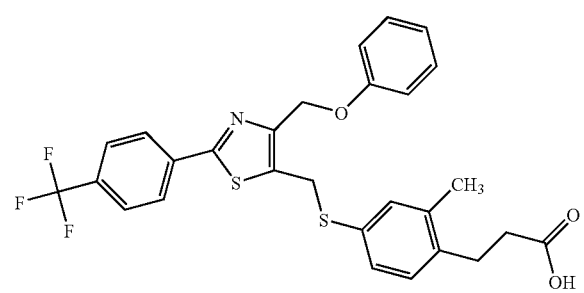

Step 1

3-(4-Mercapto-2-methyl-phenyl)-propionic acid-methyl ester (126 mg, 0.600 mmol) is dissolved into anhydrous acetonitrile (ACN) (2 mL). Cesium carbonate (326 mg, 1.00 mmol) is added to the reaction, followed by the addition of 5-Chloromethyl-4-phenoxymethyl-2-(4-trifluoromethyl-phenyl)-thiazole (200 mg, 0.5211 mmol). The reaction is allowed to stir under nitrogen at room temperature and monitored by TLC and HPLC. Upon complete consumption of the chloride, the reaction is diluted with diethyl ether and quenched with 0.1N NaOH. The two phases are separated, then the organic layer washed with water and brine. The organic phase is dried over anhydrous sodium sulfate and concentrated under vacuum. The residue is further purified using either EtOAc/Hexanes (1:9) or Acetone/Hexanes (1:9) gradients on silica gel chromatography to yield 3-{2-Methyl-4-[4-phenoxymethyl-2-(4-trifluoromethyl-phenyl)-thiazol-5-ylmethylsulfanyl]-phenyl}-propionic acid methyl ester (100 mg, 0.1796 mmol) or 30%.

Step 2

3-{2-Methyl-4-[4-phenoxymethyl-2-(4-trifluoromethyl-phenyl)-thiazol-5-ylmethylsulfanyl]-phenyl}-propionic acid methyl ester (100 mg, 0.1796 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the pure 3-{2-Methyl-4-[4-phenoxymethyl-2-(4-trifluoromethyl-phenyl)-thiazol-5-ylmethylsulfanyl]-phenyl}-propionic acid in near quantitative yield (93 mg, 0.170 mmol).

The following compounds are made in a substantially similar manner:

Example 46

3-{4-[4-[2-(2-Chloro-6-fluoro-phenyl)-ethyl]-2-(4-trifluoromethyl-phenyl)-thiazol-5-ylmethylsulfanyl]-2-methyl-phenyl}-propionic acid

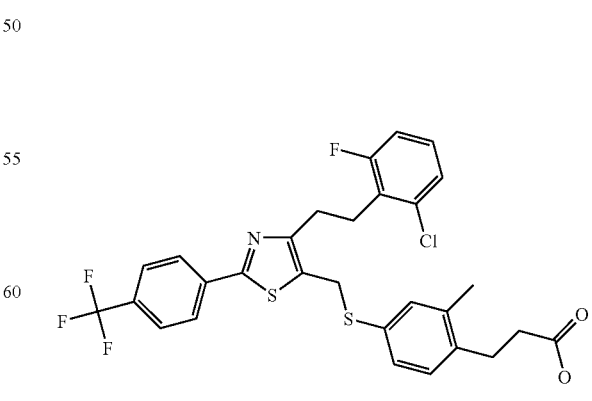

MS (ES): 594.2(M$^+$+1).

Example 47

3-{2-Methyl-4-[4-phenoxymethyl-2-(4-trifluoromethyl-phenyl)-thiazol-5-ylmethylsulfanyl]-phenyl}-propionic acid

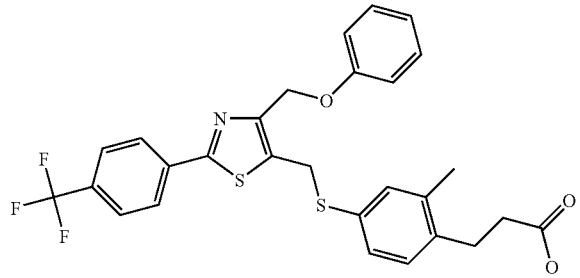

MS (ES): 544.2 (M$^+$+1).

Example 48

3-{2-Methyl-4-[4-phenylsulfanylmethyl-2-(4-trifluoromethyl-phenyl)-thiazol-5-ylmethylsulfanyl]-phenyl}-propionic acid

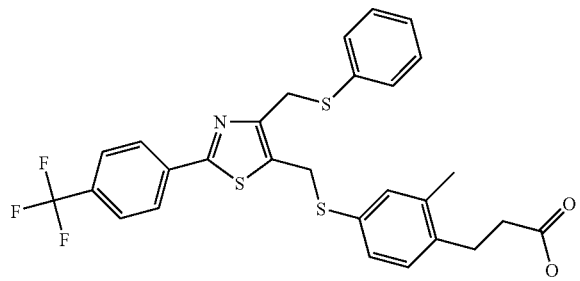

MS (ES): 560.19(M$^+$+1).

Example 49

{2-Methyl-4-[4-phenyl-2-(4-trifluoromethyl-phenyl)-thiazol-5-ylmethylsulfanyl]-phenoxy}-acetic acid

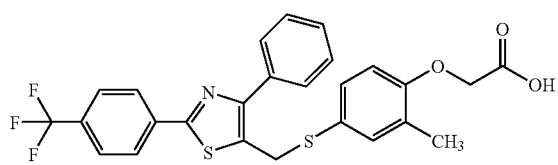

Example 50

{2-Methyl-4-[4-phenyl-2-(4-trifluoromethyl-phenyl)-thiazol-5-ylmethoxy]-phenoxy}-acetic acid

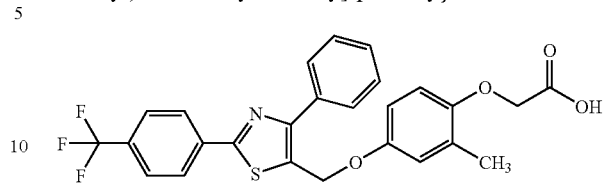

Example 51

(3-{2-[5-Ethyl-2-(4-trifluoromethyl-phenyl)-thiazol-4-yl]-ethoxy}-phenyl)-acetic acid

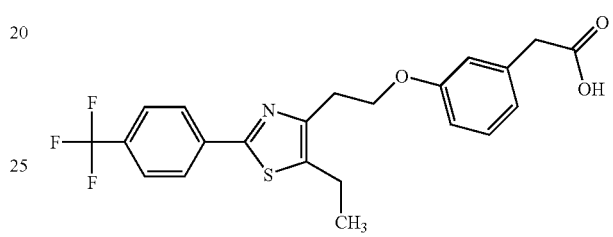

Step 1

(3-Hydroxy-phenyl)-acetic acid methyl ester (166 mg, 1.0 mmol) is dissolved into anhydrous acetonitrile (ACN) (5 mL). Toluene-4-sulfonic acid 2-[5-ethyl-2-(4-trifluoromethyl-phenyl)-thiazol-4-yl]-ethyl ester (432 mg, 0.950 mmol) is added to the reaction, followed by the addition of cesium carbonate (652 mg, 2.00 mmol). The reaction is allowed to stir under nitrogen at room temperature and monitored by TLC and HPLC. Upon complete consumption of the tosylate, the reaction is diluted with diethyl ether and quenched with 0.1N NaOH. The two phases are separated, then the organic layer washed with water and brine. The organic phase is dried over anhydrous sodium sulfate and concentrated under vacuum. The residue is further purified using either EtOAc/Hexanes (1:9) or Acetone/Hexanes (1:9) gradients on silica gel chromatography to yield (3-{2-[5-Ethyl-2-(4-trifluoromethyl-phenyl)-thiazol-4-yl]-ethoxy}-phenyl)-acetic acid methyl ester (140 mg, 0.311 mmol) or 33%.

Step 2

3-{2-[5-Ethyl-2-(4-trifluoromethyl-phenyl)-thiazol-4-yl]-ethoxy}-phenyl)-acetic acid methyl ester (140 mg, 0.311 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the pure 3-{2-[5-Ethyl-2-(4-trifluoromethyl-phenyl)-thiazol-4-yl]-ethoxy}-phenyl)-acetic acid in near quantitative yield (133 mg, 0.306 mmol).

The following compounds are made in a substantially similar manner:

Example 52

3-(2-Methyl-4-{2-[5-propyl-2-(4-trifluoromethyl-phenyl)-thiazol-4-yl]-ethoxy}-phenyl)-propionic acid

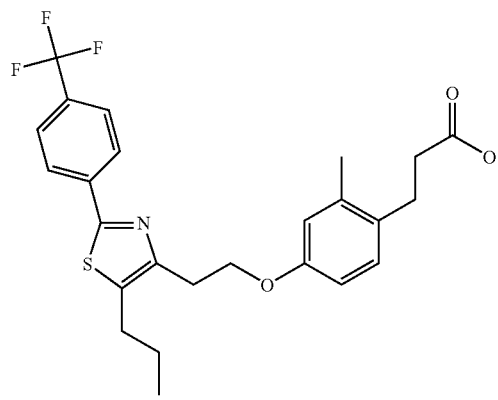

MS (ES): 478.05(M⁺+1).

Example 53

3-(2-Methyl-4-{2-[5-propyl-2-(4-trifluoromethyl-phenyl)-thiazol-4-yl]-ethylsulfanyl}-phenyl)-propionic acid

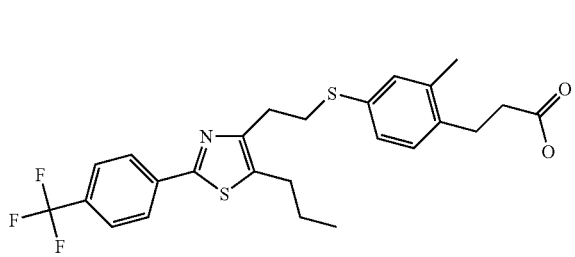

MS (ES): 494.5(M⁺+1).

Example 54

(3-{2-[5-Ethyl-2-(4-trifluoromethyl-phenyl)-thiazol-4-yl]-ethoxy}-phenyl)-acetic acid

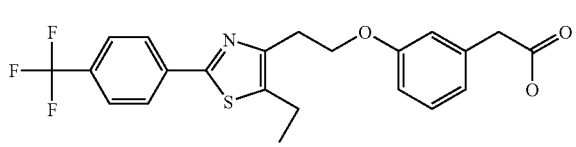

MS (ES): 434.09(M⁺+1).

Example 55

(3-{2-[5-Propyl-2-(4-trifluoromethyl-phenyl)-thiazol-4-yl]-ethoxy}-phenyl)-acetic acid

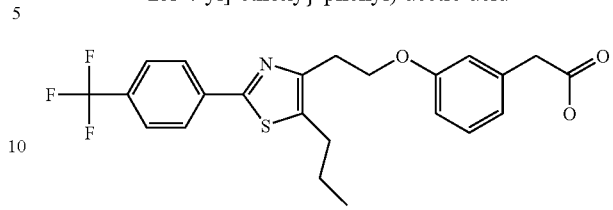

MS (ES): 450.11 (M⁺+1).

Example 56

(2-Methyl-4-{2-[5-propyl-2-(4-trifluoromethyl-phenyl)-thiazol-4-yl]-ethylsulfanyl}-phenoxy)-acetic acid

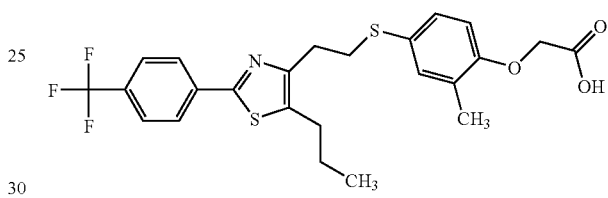

Example 57

3-{4-[4-Ethyl-2-(4-trifluoromethyl-phenyl)-oxazol-5-ylmethoxy]-2-methyl-phenyl}-propionic acid

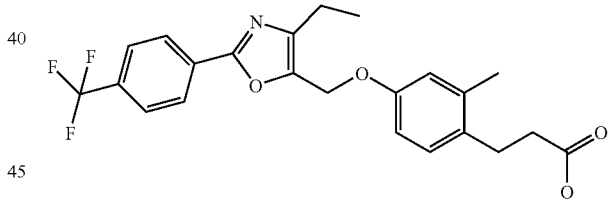

Step A

3-{4-[4-Ethyl-2-(4-trifluoromethyl-phenyl)-oxazol-5-ylmethoxy]-2-methyl-phenyl}-propionic acid methyl ester

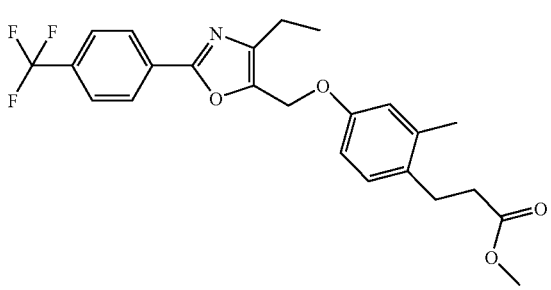

To a solution of [4-Ethyl-2-(4-trifluoromethyl-phenyl)-oxazol-5-yl]-methanol (0.108 g, 0.400 mmole) and 3-(4-Hydroxy-2-methyl-phenyl)-propionic acid methyl ester (0.078 g, 0.400 mmole) in toluene (2 mL) at room temperature, is added tributylphosphine followed by a solution of 1,1'-(azodicarbonyl)-dipiperidine (0.201 g, 0.8 mmole) in toluene (2 mL). The reaction is stirred overnight, then diluted with hexane (10 mL). The precipitate is removed through filtration and the filtrate is concentrated, loaded to a silica gel column, eluted with ethyl acetate in hexane (0-15%) and concentrated to provide the titled compound as a white solid. Mass [EI+] 448 ($M^++H$).

Step B

3-{4-[4-Ethyl-2-(4-trifluoromethyl-phenyl)-oxazol-5-ylmethoxy]-2-methyl-phenyl}-propionic acid 3-{4-[4-Ethyl-2-(4-trifluoromethyl-phenyl)-oxazol-5-yl-methoxy]-2-methyl-phenyl}-propionic acid methyl ester (0.100 g, 0.223 mmole) is treated with a mixture of $NaOH_{(aq)}$ (1 mL)/THF (3 mL)/MeOH (3 mL) at room temperature overnight. The organic solvents are removed on rota-vapor. The residue is diluted with water (10 mL), acidified to pH=2 with 6N $HCl_{(aq)}$. The precipitate is collected through filtration, washed with cold water (30 mL) and dried to provide the titled compound as a white solid. Mass [EI+] 434 ($M^++H$), 432 ($M^+-H$).

The following compounds are made in a similar manner:

Example 58

{4-[4-Ethyl-2-(4-trifluoromethyl-phenyl)-oxazol-5-ylmethoxy]-2-methyl-phenoxy}-acetic acid White solid, Mass [EI+] 436 ($M^++H$), 434 ($M^+-H$).

Example 59

{4-[4-Ethyl-2-(4-trifluoromethyl-phenyl)-oxazol-5-ylmethylsulfanyl]-2-methyl-phenoxy}-acetic acid White solid, Mass [EI+] 452 ($M^++H$), 450 ($M^+-H$).

Example 60

{2-Methyl-4-[4-methyl-2-(4'-trifluoromethyl-biphenyl-4-yl)-thiazol-5-ylmethylsulfanyl]-phenoxy}-acetic acid To a solution of {4-[2-(4-Bromo-phenyl)-4-methyl-thiazol-5-ylmethylsulfanyl]-2-methyl-phenoxy}-acetic acid ethyl ester (53 mg, 0.1076 mmol) in toluene:ethanol (1:1, 2.0 mL) is added palladium tetrakis triphenylphosphine (5.0 mg, 0.0053 mmol), 4-(trifluoromethyl)-phenyl boronic acid (22.5 mg, 0.1184 mmol), and a solution of sodium carbonate (0.216 mL, 1.0M in water, 0.216 mmol). The reaction is purged with nitrogen and heated to reflux. The reaction is monitored by HPLC, and upon completion is allowed to cool to room temperature. The reaction is diluted with EtOAc and then washed with 0.1N sodium hydroxide, water, and brine. The organic layer is dried over anhydrous sodium sulfate, then concentrated. The product is purified by flash column chromatography. The pure ester compound is then diluted with THF and 1N sodium hydroxide is added. The reaction is allowed to stir at room temperature, and monitored by TLC. Upon completion, 1N hydrochloric acid is added to neutralize the solution. The reaction is diluted with EtOAc and then washed with water. The organic layer is dried over anhydrous sodium sulfate and concentrated to the pure acid, 50 mg or 94% yield. MS (ES): 530.7 ($M^++1$), the structure is also confirmed by proton NMR.

The following compounds are made in a similar manner:

Example 61

{4-[2-(3',5'-Bis-trifluoromethyl-biphenyl-4-yl)-4-methyl-thiazol-5-ylmethylsulfanyl]-2-methyl-phenoxy}-acetic acid

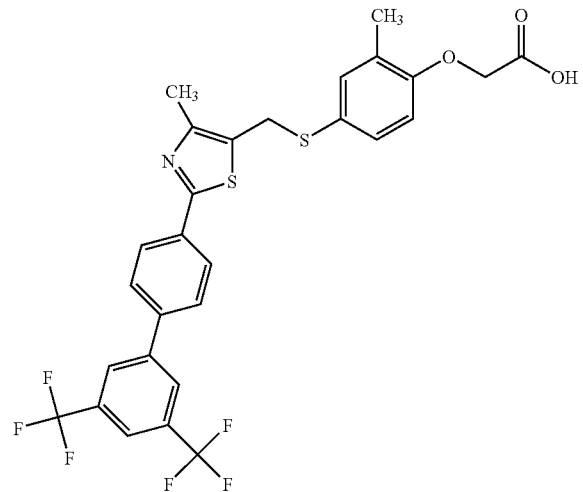

Example 62

{4-[2-(3'-Hydroxymethyl-biphenyl-4-yl)-4-methyl-thiazol-5-ylmethylsulfanyl]-2-methyl-phenoxy}-acetic

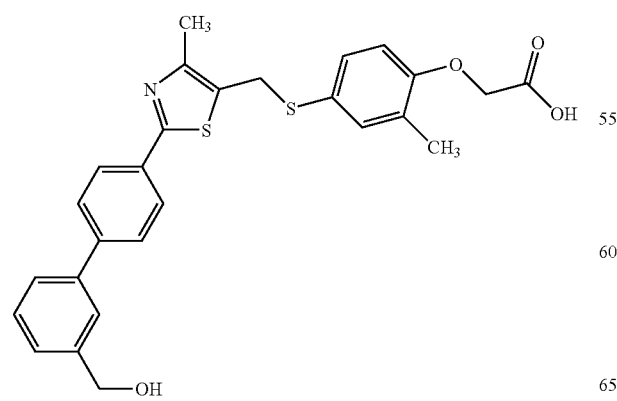

Example 63

{4-[2-(3'-Isopropyl-biphenyl-4-yl)-4-methyl-thiazol-5-ylmethylsulfanyl]-2-methyl-phenoxy}-acetic acid

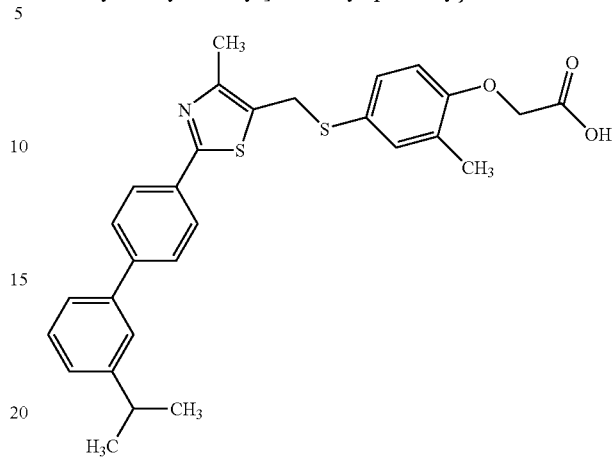

Example 64

{4-[2-(3'-Acetyl-biphenyl-4-yl)-4-methyl-thiazol-5-ylmethylsulfanyl]-2-methyl-phenoxy}-acetic acid

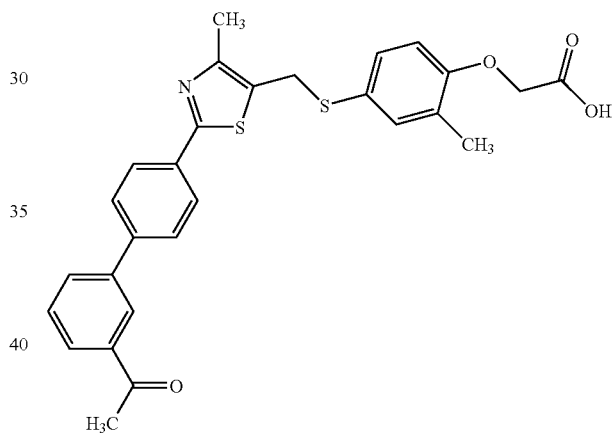

Example 65

{2-Methyl-4-[4-methyl-2-(3'-trifluoromethyl-biphenyl-4-yl)-thiazol-5-ylmethylsulfanyl]-phenoxy}-acetic acid

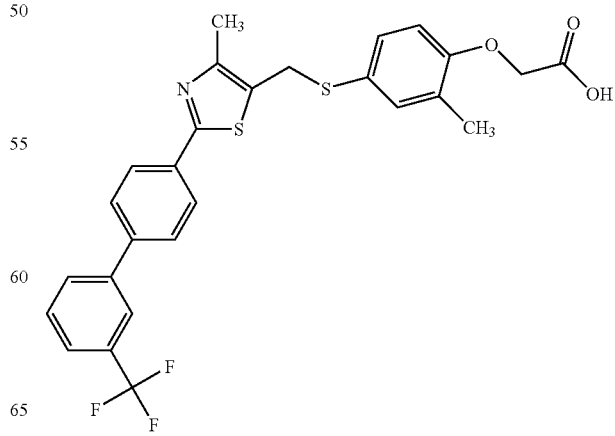

Example 66

{4-[2-(3',5'-Dimethyl-biphenyl-4-yl)-4-methyl-thiazol-5-ylmethylsulfanyl]-2-methyl-phenoxy}-acetic acid

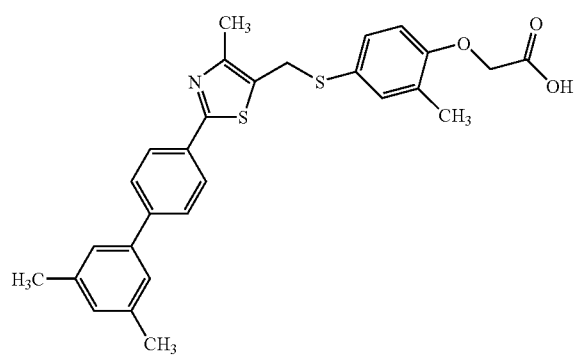

Example 67

{2-Methyl-4-[S-methyl-2-(4'-methyl-biphenyl-4-yl)-oxazol-4-ylmethylsulfanyl]-phenoxy}-acetic acid

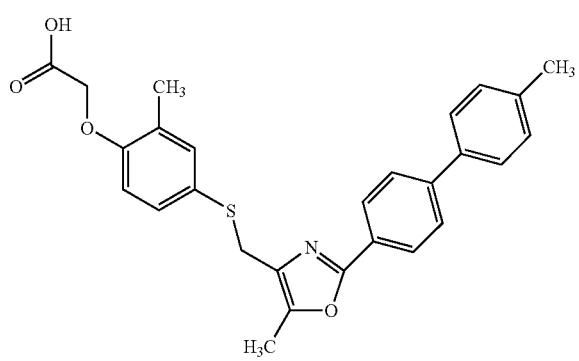

Example 68

{4-[2-(3',5'-Bis-trifluoromethyl-biphenyl-4-yl)-5-methyl-oxazol-4-ylmethylsulfanyl]-2-methyl-phenoxy}-acetic acid

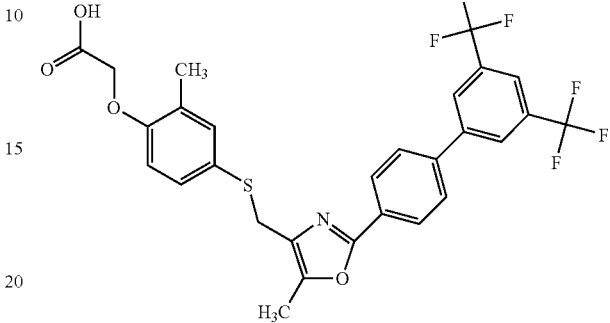

Example 69

{4-[2-(4'-Butyl-biphenyl-4-yl)-5-methyl-oxazol-4-ylmethylsulfanyl]-2-methyl-phenoxy}-acetic acid

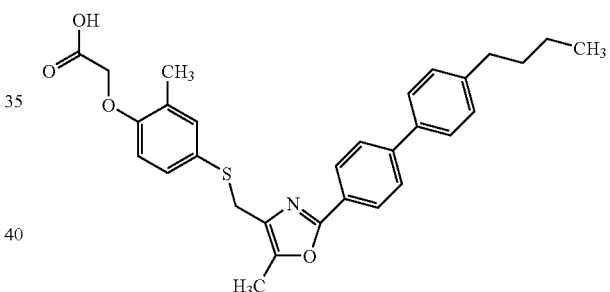

Example 70

{4-[2-(4'-Butyl-biphenyl-4-yl)-5-methyl-oxazol-4-ylmethoxy]-2-methyl-phenoxy}-acetic acid

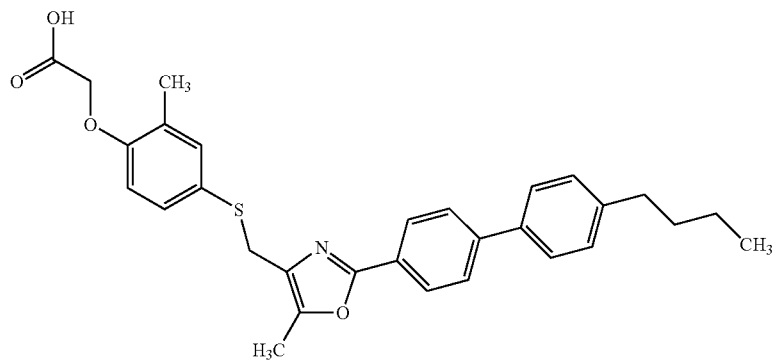

Example 71

{4-[4-Ethyl-2-(4-trifluoromethyl-phenyl)-thiazol-5-ylmethoxy]-3-methyl-phenoxy}-acetic acid

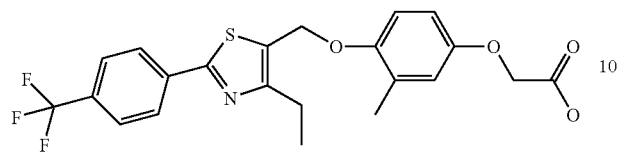

Step A

{4-[4-Ethyl-2-(4-trifluoromethyl-phenyl)-thiazol-5-ylmethoxy]-3-methyl-phenoxy}-acetic acid ethyl ester To a mixture of {3-Bromo-4-[4-ethyl-2-(4-trifluoromethyl-phenyl)-thiazol-5-ylmethoxy]-phenoxy}-acetic acid ethyl ester (100 mg, 0.18 mmol), methyl boronic acid (33 mg, 0.54 mmol) and cesium fluoride (90 mg, 0.54 mmol) in dioxane (2 mL) is added [1,1']-(bisdiphenylphosphino)ferrocene]-dichloridepalladium (II) complex with methylene chloride (1:1, 29 mg) under nitrogen. The mixture is heated to 80° C. for 18 hrs, cooled to room temperature, loaded on silica gel column. Chromatography gave the title compound (80 mg).

Step B

{4-[4-Ethyl-2-(4-trifluoromethyl-phenyl)-thiazol-5-ylmethoxy]-3-methyl-phenoxy}-acetic acid To a solution of {4-[4-Ethyl-2-(4-trifluoromethyl-phenyl)-thiazol-5-ylmethoxy]-3-methyl-phenoxy}-acetic acid ethyl ester (80 mg) in THF (1 mL) is added LiOH (1.0 M, 1.0 mL), after 1 hr, acidified by 5 N HCl and extracted with ethyl, dried over sodium sulfate. Concentration gave the title acid compound (80 mg). MS (ES): 452.03 (M$^+$+1), the structure is also confirmed by proton NMR.

The following compounds are made in similar manner:

Example 72

{4-[4-Ethyl-2-(4-trifluoromethyl-phenyl)-thiazol-5-ylmethoxy]-3-vinyl-phenoxy}-acetic acid

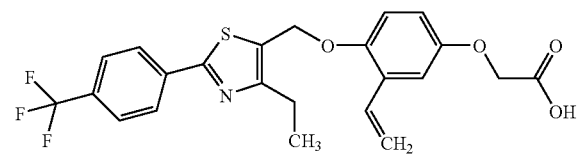

MS (ES): 464.01(M$^+$+1), the structure is also confirmed by proton NMR.

Example 73

2-{4-[4-Ethyl-2-(4-trifluoromethyl-phenyl)-thiazol-5-ylmethoxy]-3-methyl-phenoxy}-2-methyl-propionic acid

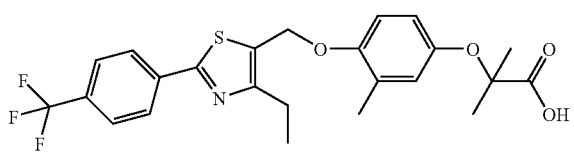

MS (ES): 480.0(M$^+$+1), the structure is also confirmed by proton NMR.

Example 74

{4-[4-Methyl-2-(4-trifluoromethyl-phenyl)-oxazol-5-ylmethoxy]-2-propyl-phenoxy}-acetic acid

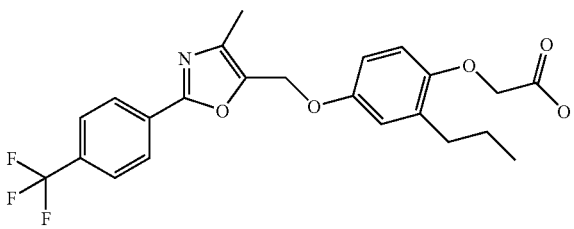

To a suspension of 5-chloromethyl-4-methyl-2-(4-trifluoromethyl-phenyl)-oxazole (0.10 g, 0.36 mmol) and Cs$_2$CO$_3$ (0.24 g, 0.72 mmol) in 2 mL acetonitrile is added (4-hydroxy-2-propyl-phenoxy)-acetic acid ethyl ester (0.09 g, 0.38 mmol). The solution is stirred for 6 hrs and poured into water (10 mL) and extracted with ethyl acetate (3×15 mL). The combined organics are washed with water (10 mL) and brine (10 mL), dried (Na$_2$SO$_4$), filtered and concentrated in vacuo. The crude product is purified using flash column chromatography (20% ethyl acetate/hexanes) to afford 0.13 g (85%) desired {4-[4-Methyl-2-(4-trifluoromethyl-phenyl)-oxazol-5-ylmethoxy]-2-propyl-phenoxy}-acetic acid methyl ester. This ester is hydrolyzed in the usual way using 0.14 g ester and 3 eq. 1M LiOH in 3 mL 3:2:1 THF:MeOH:H$_2$O to afford 0.16 g (95%) of the title compound.

Example 75

{2-Methyl-4-[4-methyl-2-(4-trifluoromethyl-phenyl)-oxazol-5-ylmethanesulfonyl]-phenoxy}-acetic acid

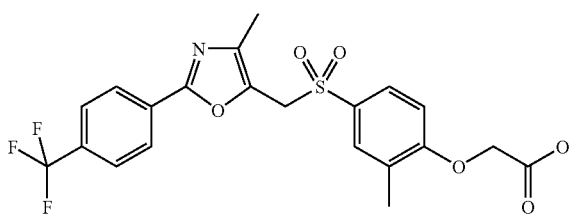

To a suspension of 5-chloromethyl-4-methyl-2-(4-trifluoromethyl-phenyl)-oxazole (0.30 g, 1.8 mmol) and Cs$_2$CO$_3$ in 8 mL acetonitrile is added (4-Mercapto-2-methyl-phenoxy)-acetic acid ethyl ester (0.25 g, 1.1 mmol). The solution is stirred for 6 hrs and poured into water (50 mL) and extracted with ethyl acetate (3×25 mL). The combined organics are washed with water (10 mL) and brine (30 mL), dried (Na$_2$SO$_4$), filtered and concentrated in vacuo. The crude product is purified using flash column chromatography (10%-20% ethyl acetate/hexanes) to afford 0.40 g (79%) of {2-Methyl-4-[4-methyl-2-(4-trifluoromethyl-phenyl)-oxazol-5-ylmethylsulfanyl]-phenoxy}-acetic acid ethyl ester. To a stirred solution of this ester (0.21 g, 0.44 mmol) is added m-CPBA (50%) (0.31 g, 0.89 mmol) at 0° C. After 10 min. the solution is poured into water (50 mL) and extracted with methylene chloride (3×20 mL). The combine methylene chloride layers are washed with 1 N NaOH (25 mL), water (25 mL) and brine (25 mL), dried (Na$_2$SO$_4$), filtered and concentrated in Vacuo. The crude sulphone is purified using flash column chromatography (10%-25% ethyl acetate hexanes) to give 0.15 g (68%) of {2-Methyl-4-[4-methyl-2-(4-trifluoromethyl-phenyl)-oxazol-5-ylmethanesulfonyl]-phenoxy}-acetic acid ethyl ester. Hydrolysis of this sulphone (0.15 g, 0.30 mmol) occurred under the usual conditions (3 eq. of a 1N solution of LiOH in 1 mL of a 3:2:1 solution of THF:MeOH:H$_2$O) to provide the title compound 0.11 g (78%) after workup with aq. NH$_4$Cl and ethyl acetate.

Example 76

(4-{2-[4-Isopropyl-2-(4-trifluoromethyl-phenyl)-oxazol-5-yl]-ethoxy}-2-methyl-phenyl)-acetic acid

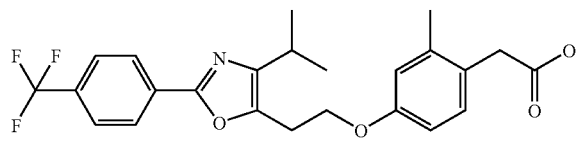

MS M$^+$+1 448. The structure is confirmed by $^1$H NMR spectroscopy.

Example 77

(3-{2-[4-Isopropyl-2-(4-trifluoromethyl-phenyl)-oxazol-5-yl]-ethoxy}-phenyl)-acetic acid

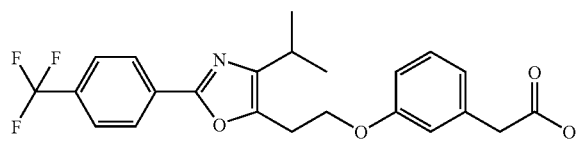

MS M$^+$+1 434. The structure is confirmed by $^1$H NMR spectroscopy.

Example 78

{3-[4-Isopropyl-2-(4-trifluoromethyl-phenyl)-oxazol-5-ylmethoxy]-phenyl}-acetic acid

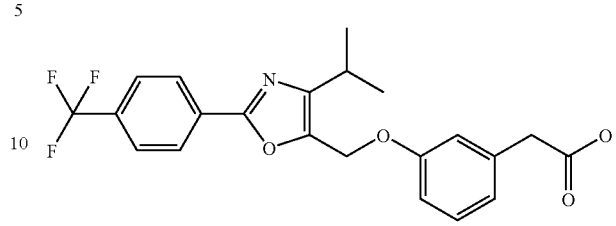

MS M$^+$+1 420. The structure is confirmed by $^1$H NMR spectroscopy.

Example 79

{3-[4-Isopropyl-2-(4-trifluoromethyl-phenyl)-oxazol-5-ylmethylsulfanyl]-phenyl}-acetic acid

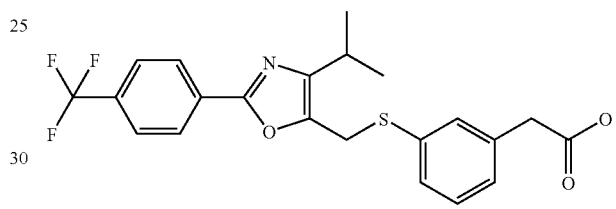

MS M$^+$+1 436. The structure is confirmed by $^1$H NMR spectroscopy.

Example 80

(3-{2-[4-Isopropyl-2-(4-trifluoromethyl-phenyl)-oxazol-5-yl]-ethylsulfanyl}-phenyl)-acetic acid

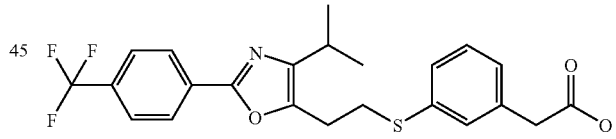

MS M$^+$+1 450. The structure is confirmed by $^1$H NMR spectroscopy.

Example 81

{3-[4-Isopropyl-2-(4-trifluoromethyl-phenyl)-thiazol-5-ylmethoxy]-phenyl}-acetic acid

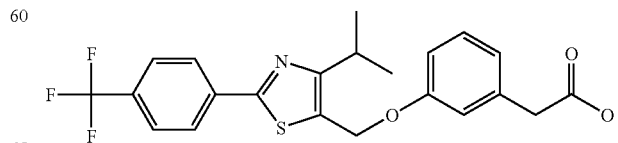

MS (ES): 436.2 (M$^+$+1).

Example 82

{3-[5-Methyl-2-(4-trifluoromethyl-phenyl)-oxazol-4-ylmethoxy]-phenyl}-acetic acid

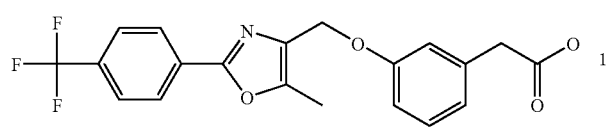

MS (ES): 392.2 (M$^+$+1).

Example 83

3-(2-Methyl-4-{[5-methyl-2-(4-trifluoromethyl-phenyl)-oxazol-4-ylmethyl]-carbamoyl}-phenyl)-propionic acid

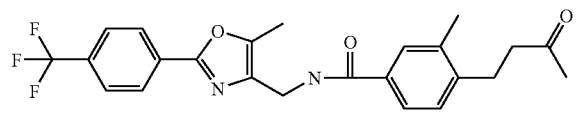

Step A 3-(2-Methyl-4-{[5-methyl-2-(4-trifluoromethyl-phenyl)-oxazol-4-ylmethyl]-carbamoyl}-phenyl)-propionic acid ethyl ester To a mixture of C-[5-methyl-2-(4-trifluoromethyl-phenyl)-oxazol-4-yl]-methylamine (0.2 g, 0.78 mmol) and 4-(2-carboxy-ethyl)-3-methyl-benzoic acid (0.173 g, 0.78 mmol) and DMAP (5 mg) in methylene chloride (5 mL) are added triethyl amin (0.12 mL, 0.86 mml) and EDCI (150 mg, 0.78 mmol) at room temperature. After stirred for 3 hrs, diluted with chloroform, washed with water, 1N HCl and 2 N NaOH aqueous. Concentration and column chromatography on silica gel gave the title compound (240 mg).

Step B 3-(2-Methyl-4-{[5-methyl-2-(4-trifluoromethyl-phenyl)-oxazol-4-ylmethyl]-carbamoyl}-phenyl)-propionic acid To a solution of 3-(2-methyl-4-{[5-methyl-2-(4-trifluoromethyl-phenyl)-oxazol-4-ylmethyl]-carbamoyl}-phenyl)-propionic acid ethyl ester (70 mg) in enthanol (1 mL) is added NaOH (5.0 N, 1.0 mL), the mixture is heated at 50° C. for 2 hrs, acidified with 5 N HCl, extracted with ethyl acetate, dried over sodium sulfate. Concentration gave the title compound (70 mg).

Example 84

3-(4-{[4-Isopropyl-2-(4-trifluoromethyl-phenyl)-thiazole-5-carbonyl]-amino}-2-methyl-phenyl)-propionic acid

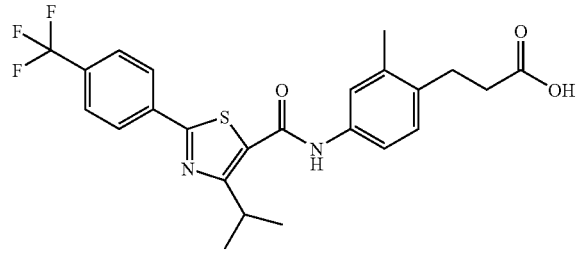

Step A 3-(4-{[4-Isopropyl-2-(4-trifluoromethyl-phenyl)-thiazole-5-carbonyl]-amino}-2-methyl-phenyl)-propionic acid methyl ester To a mixture of 4-Isopropyl-2-(4-trifluoromethyl-phenyl)-thiazole-5-carboxylic acid (0.11 g, 0.35 mmol), 3-(4-Amino-2-methyl-phenyl)-propionic acid methyl ester (0.07 g, 0.35 mmol), and DMAP (0.01 g, 0.082 mmol) in CH$_2$Cl$_2$ (5 mL) is added EDCI (0.08 g, 0.42 mmol). After stirring for 2 h at RT, the mixture is concentrated. The residue is redissolved in EtOAc, and the organics are washed with 1N HCl (1×), 2N NaOH (2×), water, and brine, and dried with MgSO$_4$. The crude material is purified by flash chromatography to yield the title compound (0.12 g, 70%).

Step B 3-(4-{[4-Isopropyl-2-(4-trifluoromethyl-phenyl)-thiazole-5-carbonyl]-amino}-2-methyl-phenyl)-propionic acid Hydrolysis of the product from step one in the presence of sodium hydroxide gave the title compound (32 mg, 55%). MS (ES): 477 (M$^+$+1); the structure is also confirmed by $^1$H NMR.

The following compounds are made in a similar manner:

Example 85

3-(4-{2-[5-Ethyl-2-(4-trifluoromethyl-phenyl)-thiazol-4-yl]-acetylamino}-2-methyl-phenyl)-propionic acid

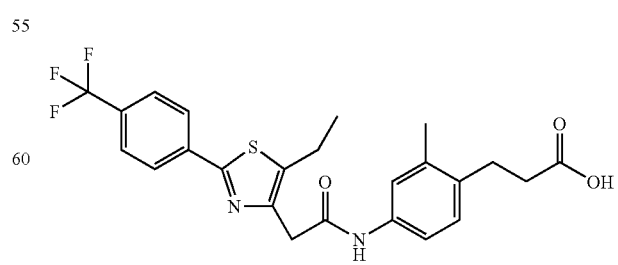

MS (ES): 477 (M$^+$+1); the structure is also confirmed by $^1$H NMR.

Example 86

3-[4-({[4-Isopropyl-2-(4-trifluoromethyl-phenyl)-thiazole-5-carbonyl]-methyl-amino}-methyl)-2-methyl-phenyl]-propionic acid

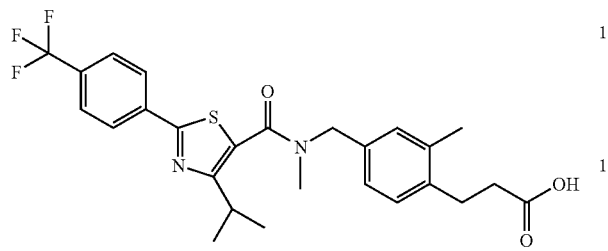

(26 mg, 74%). MS (ES): 505 (M$^+$); the structure is also confirmed by $^1$H NMR.

Example 87

3-[4-({[4-Isopropyl-2-(4-trifluoromethyl-phenyl)-thiazole-5-carbonyl]-amino}-methyl)-2-methyl-phenyl]-propionic acid

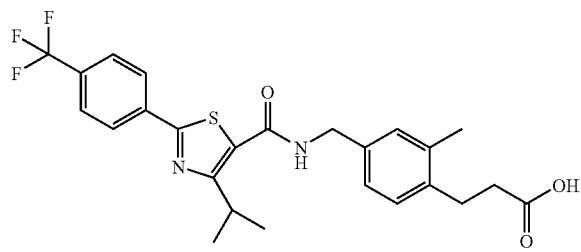

(37 mg, 62%). MS (ES): 491 (M$^+$); the structure is also confirmed by $^1$H NMR.

Example 88

(2-Methyl-4-{[5-methyl-2-(4-trifluoromethyl-phenyl)-oxazol-4-ylmethyl]-sulfamoyl}-phenoxy)-acetic acid

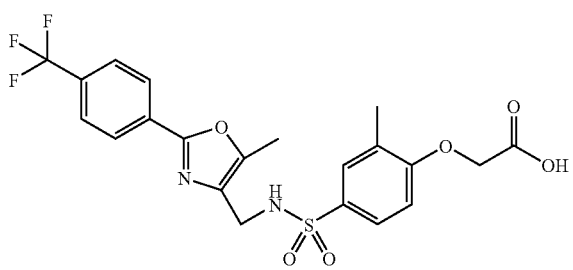

MS (ES): 485 (M$^+$+1); the structure is also confirmed by $^1$H NMR.

Example 89

3-(2-Methyl-4-{[4-methyl-2-(4-trifluoromethyl-phenyl)-thiazol-5-ylmethyl]-amino}-phenyl)-propionic acid sodium salt

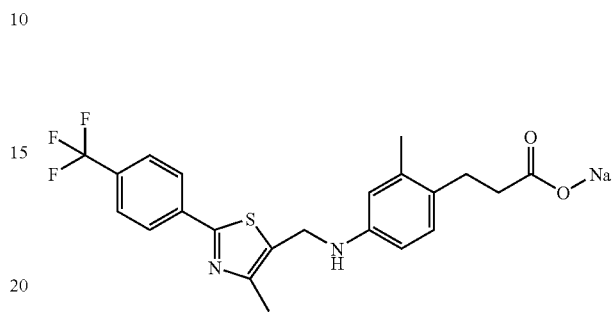

Step A 3-(2-Methyl-4-{[4-methyl-2-(4-trifluoromethyl-phenyl)-thiazol-5-ylmethyl]-amino}-phenyl)-propionic acid methyl ester To a solution of 3-(4-Amino-2-methyl-phenyl)-propionic acid methyl ester (0.14 g, 0.70 mmol) and 4-Methyl-2-(4-trifluoromethyl-phenyl)-thiazole-5-carbaldehyde (0.19 g, 0.71 mmol) in anhydrous CH$_2$Cl$_2$ (5 mL) is added 4 Å molecular sieves followed by acetic acid (50 μL, 0.87 mmol). The mixture is stirred at RT for 2 h. Sodium triacetoxyborohydride (0.22 g, 1.04 mmol) is added, and the mixture is stirred at RT for 12 h. The reaction is quenched with saturated NaHCO$_3$. The organics are separated and washed with saturated NaHCO$_3$ and brine, and dried with MgSO$_4$. The crude material is purified by flash chromatography to yield the title compound (0.21 g, 68%).

Step B 3-(2-Methyl-4-{[4-methyl-2-(4-trifluoromethyl-phenyl)-thiazol-5-ylmethyl]-amino}-phenyl)-Propionic acid sodium salt A solution of 3-(2-Methyl-4-{[4-methyl-2-(4-trifluoromethyl-phenyl)-thiazol-5-ylmethyl]-amino}-phenyl)-propionic acid methyl ester (0.06 g, 0.13 mmol) and 5M NaOH (0.35 mL, 1.75 mmol) is heated to 70° C. for 14 h. Upon cooling, the solid is filtered and dried in vacuo to yield the title compound (10 mg, 17%) as the sodium salt. MS (ES): 435 (M$^+$); the structure is also confirmed by $^1$H NMR.

The following compounds are made in a similar manner:

Example 90

3-[4-({Bis-[4-methyl-2-(4-trifluoromethyl-phenyl)-thiazol-5-ylmethyl]-amino}-methyl)-2-methyl-phenyl]-propionic acid TFA salt

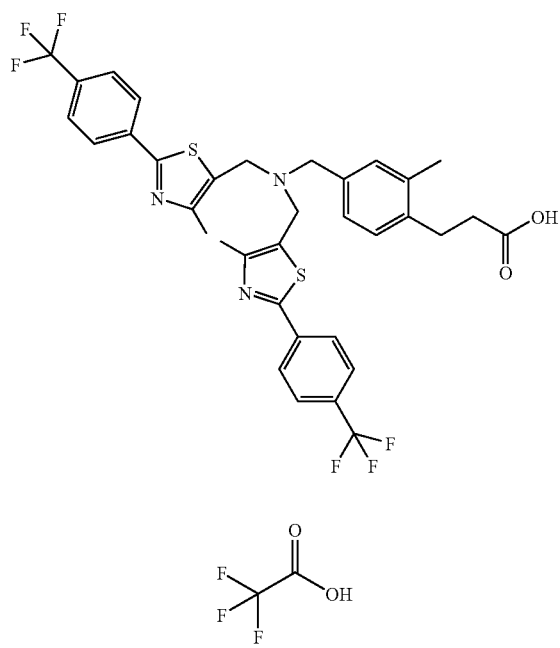

MS (ES): 704 (M⁺+1); the structure is also confirmed by ¹H NMR.

Example 91

3-[2-Methyl-4-({methyl-[4-methyl-2-(4-trifluoromethyl-phenyl)-thiazol-5-ylmethyl]-amino}-methyl)-phenyl]-propionic acid methyl ester TFA salt

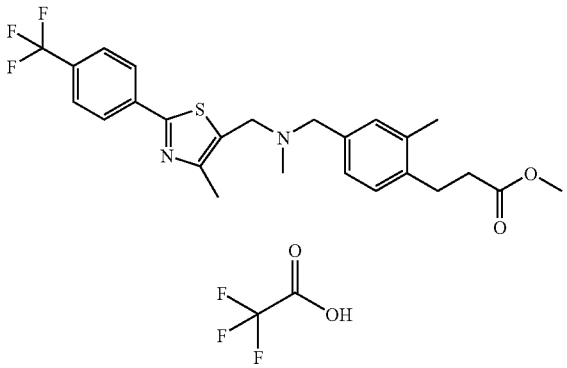

MS (ES): 477 (M⁺+1); the structure is also confirmed by ¹H NMR.

Example 92

3-(4-{Methoxycarbonyl-[4-methyl-2-(4-trifluoromethyl-phenyl)-thiazol-5-ylmethyl]-amino}-2-methyl-phenyl)-propionic acid

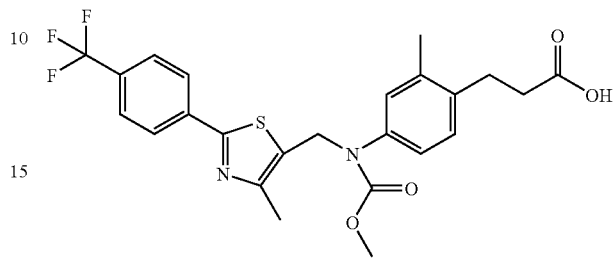

Step A 3-(4-{Methoxycarbonyl-[4-methyl-2-(4-trifluoromethyl-phenyl)-thiazol-5-ylmethyl]-amino}-2-methyl-phenyl)-propionic acid methyl ester To a 0° C. solution of 3-(2-Methyl-4-{[4-methyl-2-(4-trifluoromethyl-phenyl)-thiazol-5-ylmethyl]-amino}-phenyl)-propionic acid methyl ester (0.05 g, 0.11 mmol) and pyridine (0.027 mL, 0.33 mmol) in anhydrous CH₂Cl₂ (3 mL) is added methyl chloroformate (0.026 mL, 0.34 mmol) dropwise. The mixture is allowed to warm to RT overnight. Water is added, and the mixture is extracted with CH₂Cl₂. The combined organics are dried with MgSO₄ and concentrated to yield the title compound (57 mg, quant.)

Step B 3-(4-{Methoxycarbonyl-[4-methyl-2-(4-trifluoromethyl-phenyl)-thiazol-5-ylmethyl]-amino}-2-methyl-phenyl)-propionic acid A similar procedure is followed to yield the title compound (0.048 g, 81%). MS (ES): 493 (M⁺); the structure is also confirmed by ¹H NMR.

Example 93

3-{2-Methyl-4-[4-methyl-2-(4-trifluoromethyl-phenyl)-thiazol-5-ylmethoxymethyl]-phenyl}-propionic acid

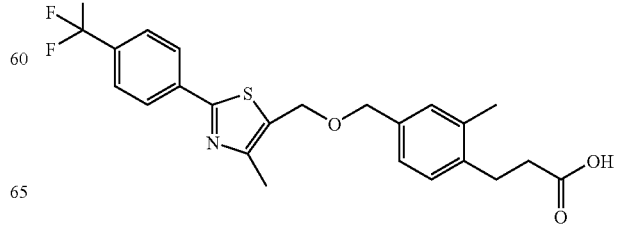

Step A

5-Iodomethyl-4-methyl-2-(4-trifluoromethyl-phenyl)-thiazole

To a solution of 5-Chloromethyl-4-methyl-2-(4-trifluoromethyl-phenyl)-thiazole (0.51 g, 1.73 mmol) in acetone is added NaI (0.42 g, 2.80 mmol). The mixture is stirred at RT for 3 h. The solid is filtered, and the filtrate is concentrated. The resulting solid is washed with Et₂O and refiltered. Concentration of the filtrate yielded the title compound (0.68 g, quant.). The material is used without further purification.

Step B

3-{2-Methyl-4-[4-methyl-2-(4-trifluoromethyl-phenyl)-thiazol-5-ylmethoxymethyl]-phenyl}-propionic acid methyl ester To a solution of 5-Iodomethyl-4-methyl-2-(4-trifluoromethyl-phenyl)-thiazole (0.14 g, 0.37 mmol) and 3-(4-Hydroxymethyl-2-methyl-phenyl)-propionic acid methyl ester (0.064 g, 0.31 mmol) in DMF (1 mL) is added sodium hydride (60% dispersion, 0.036 g, 1.50 mmol). The mixture is stirred at RT for 3 h. The reaction is quenched with water, and the mixture is extracted with EtOAc. The organics are dried with MgSO₄ and concentrated. The crude material is purified by flash chromatography to yield the title compound (0.022 g, 16%).

Step C

3-{2-Methyl-4-[4-methyl-2-(4-trifluoromethyl-phenyl)-thiazol-5-ylmethoxymethyl]-phenyl}-propionic acid A similar procedure is followed to yield the title compound (15 mg, 73%). MS (ES): 450 (M⁺+1 the structure is also confirmed by ¹H NMR.

Example 94

3-{4-[4-Isopropyl-2-(4-trifluoromethyl-phenyl)-thiazol-5-ylmethoxymethyl]-2-methyl-phenyl}-propionic acid

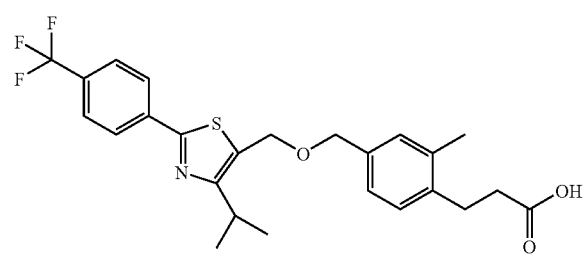

Step A

3-{4-[4-Isopropyl-2-(4-trifluoromethyl-phenyl)-thiazol-5-ylmethoxymethyl]-2-methyl-phenyl}-propionic acid methyl ester To a mixture of [4-Isopropyl-2-(4-trifluoromethyl-phenyl)-thiazol-5-yl]-methanol (0.056 g, 0.18 mmol) and 3-(4-Iodomethyl-2-methyl-phenyl)-propionic acid methyl ester (0.070 g, 0.22 mol) in DMF (1 mL) is added sodium hydride (60% dispersion, 0.016 g, 0.67 mmol). After 3.5 h, water is added, and the mixture is extracted with EtOAc. The organics are dried with MgSO₄ and concentrated. The crude material is purified by flash chromatography to yield the title compound (55 mg, 60%).

Step B

3-{4-[4-Isopropyl-2-(4-trifluoromethyl-phenyl)-thiazol-5-ylmethoxymethyl]-2-methyl-phenyl}-propionic acid A similar procedure is followed to yield the title compound (45 mg, 84%). MS (ES) 478 (M⁺+1). The structure is also confirmed by ¹H NMR.

Example 95

3-[4-(2-{2-[6-(2-Fluoro-phenyl)-pyridin-3-yl]-5-methyl-thiazol-4-yl}-ethoxy)-2-methyl-phenyl]-propionic acid

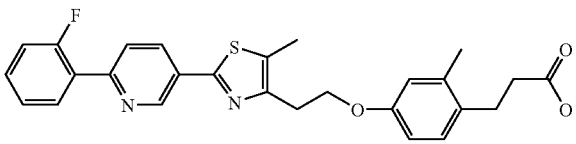

Step A

6-(2-Fluoro-phenyl)-nicotinonitrile

A mixture of 6-Chloro-nicotinonitrile (7.26 g, 52.4 mmol) and 2-fluorophenyl boronic acid (11 g, 78.6 mmol) and Na2CO3 (11 g, 103 mmol) in toluene (200 mL) and water (10 mL) is degassed and filled with nitrogen for three times, then Pd(PPh3)4 (0.73 g) is added under nitrogen. The reaction mixture is heated at 90° C. After 12 hrs, the reaction mixture is cooled to room temperature, diluted with ethyl acetate, washed with water, dried, concentrated. Column chromatography on silica gel (Hexane/ethyl acetate as eluent) gave 9.8 g of 6-(2-Fluoro-phenyl)-nicotinonitrile.

Step B

6-(2-Fluoro-phenyl)-thionicotinamide

A mixture of 6-(2-Fluoro-phenyl)-nicotinonitrile (9.8 g, 49.4 mmol) and thioacetamide (5.94 g, 79.1 mmol) in 4.0 M HCl in dioxane (200 mL) is heated at 100° C. for 3 days, cooled to room temperature. The raction mixture is poured into old saturated sodium bicarbonate and stirred for 30 min. Solid product is collected by filtration and dried under vacuum giving the title compound (11.4 g).

Step C

{2-[6-(2-Fluoro-phenyl)-pyridin-3-yl]-5-methyl-thiazol-4-yl}-acetic acid ethyl ester A mixture of 6-(2-Fluoro-phenyl)-thionicotinamide (1.5 g, 6 mmol) and 4-Bromo-3-oxo-pentanoic acid methyl ester (1.51 g, 7.2 mmol) in ethanol (100 mL) is heated to reflux for 24 h, and concentrated. The residue is purified by column chromatography on silica gel yielding 1.7 g of the product.

Step D

2-{2-[6-(2-Fluoro-phenyl)-pyridin-3-yl]-5-methyl-thiazol-4-yl}-ethanol

To a solution of {2-[6-(2-Fluoro-phenyl)-pyridin-3-yl]-5-methyl-thiazol-4-yl}-acetic acid ethyl ester (1.7 g, 4.77 mmol) in THF (10 mL) is added LiAlH4 (1.0 M in THF, 4.8 mL, 4.8 mmol) at 0-5° C., and then stirred for 2 h. The reaction is then quenched by water and 5 N NaOH, diluted with THF and filtered through a pad of celite. The filtrate is concentrated and purified by column yielding 1.4 g of the product.

Step E

3-[4-(2-{2-[6-(2-Fluoro-phenyl)-pyridin-3-yl]-5-methyl-thiazol-4-yl}-ethoxy)-2-methyl-phenyl]-propionic acid tert-butyl ester A solution of 3-(4-Hydroxy-2-methyl-phenyl)-propionic acid tert-butyl ester (120 mg, 0.5 mmol) and 2-{2-[6-(2-Fluoro-phenyl)-pyridin-3-yl]-5-methyl-thiazol-4-yl}-ethanol (101 mg, 0.323 mmol) in toluene (3.0 mL) is degassed and filled with nitrogen for 3 times. Tributylphosphine (0.124 mL, 0.5 mmol) is added to the reaction mixture under nitrogen at 0° C., followed by addition of of 1,1'-(azodicarbonyl)-dipiperidine (120 mg, 0.5 mmol). The reaction mixture is allowed to warm to room temperature and stirred overnight, the mixture is loaded on silica gel column. Chromatography gave the title compound (130 mg).

Step F

3-[4-(2-{2-[6-(2-Fluoro-phenyl)-pyridin-3-yl]-5-methyl-thiazol-4-yl}-ethoxy)-2-methyl-phenyl]-propionic acid To a solution of 3-[4-(2-{2-[6-(2-Fluoro-phenyl)-pyridin-3-yl]-5-methyl-thiazol-4-yl}-ethoxy)-2-methyl-phenyl]-propionic acid tert-butyl ester (130 mg) in methylene chloride (1 mL) is added TFA (0.8 mL) and two drops of water. The mixture is stirred for 2 h, and concentrated and purified by reversed phase HPLC (water-acetonitrile with 0.1% TFA) yield 120 mg of product. MS (ES): 477.2(M$^+$+1).

The following compounds are made in substantially similar method:

Example 96

3-[4-(2-{2-[6-(3-Fluoro-phenyl)-pyridin-3-yl]-5-methyl-thiazol-4-yl}-ethoxy)-2-methyl-phenyl]-propionic acid

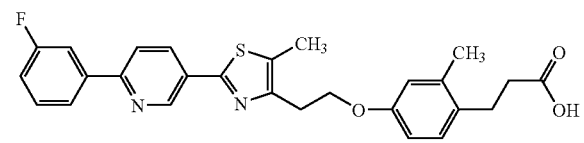

MS (ES): 477.2 (M$^+$+1).

Example 97

3-[4-(2-{2-[6-(4-Fluoro-phenyl)-pyridin-3-yl]-5-methyl-thiazol-4-yl}-ethoxy)-2-methyl-phenyl]-propionic acid

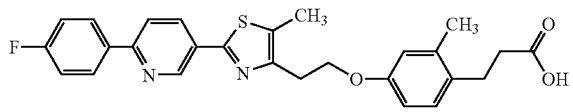

MS (ES): 477.2(M$^+$+1).

Example 98

3-[4-(2-{2-[6-phenyl-pyridin-3-yl]-5-methyl-thiazol-4-yl}-ethoxy)-2-methyl-phenyl]-propionic acid

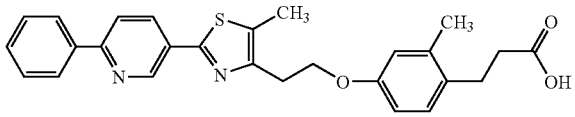

MS (ES): 459.1(M$^+$+1).

Example 99

3-[4-(2-{2-[6-(2-methyl-phenyl)-pyridin-3-yl]-5-methyl-thiazol-4-yl}-ethoxy)-2-methyl-phenyl]-propionic acid

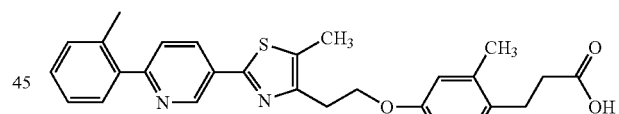

MS (ES): 473.5(M$^+$+1).

Example 100

3-[4-(2-{2-[6-(3-methyl-phenyl)-pyridin-3-yl]-5-methyl-thiazol-4-yl}-ethoxy)-2-methyl-phenyl]-propionic acid

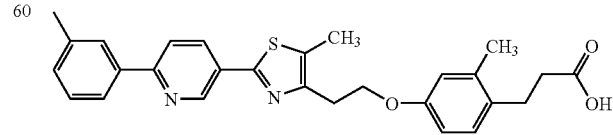

MS (ES): 473.5(M$^+$+1).

Example 101

3-[4-(2-{2-[6-(4-methyl-phenyl)-pyridin-3-yl]-5-methyl-thiazol-4-yl}-ethoxy)-2-methyl-phenyl]-propionic acid

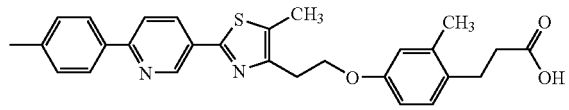

MS (ES): 473.4(M⁺+1).

Example 102

3-{4-[2-(2-[2,2']Bipyridinyl-5-yl-5-methyl-thiazol-4-yl)-ethoxy]-2-methyl-phenyl}-propionic acid

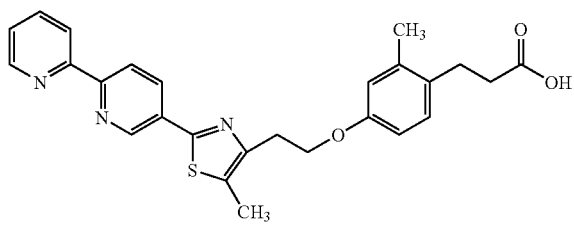

MS (ES): 460.5 (M⁺+1)

Example 103

3-(2-Methyl-4-{2-[5-methyl-2-(6-phenoxy-pyridin-3-yl)-thiazol-4-yl]-ethoxy}-phenyl)-propionic acid

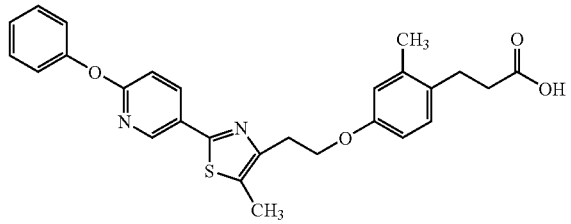

MS (ES): 475.4 (M⁺+1).

Example 104

3-(2-Methyl-4-{2-[5-methyl-2-(6-phenoxy-pyridin-3-yl)-oxazol-4-yl]-ethoxy}-phenyl)-propionic acid, HCl salt

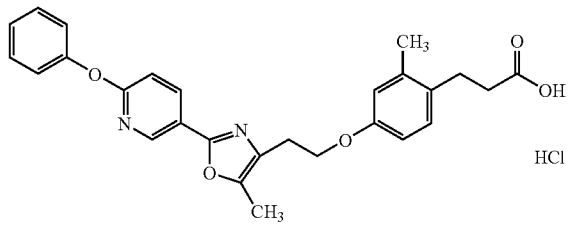

MS (ES): 459.2(M⁺+1-HCl)

Example 105

3-(2-Methyl-4-{2-[5-methyl-2-(6-phenylsulfanyl-pyridin-3-yl)-oxazol-4-yl]-ethoxy}-phenyl)-propionic acid, HCl salt

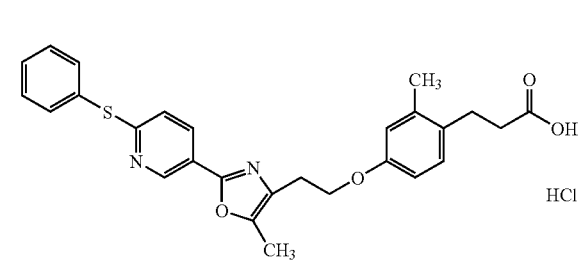

MS (ES): 475.1(M⁺+1-HCl).

Example 106

3-(2-Methyl-4-{2-[5-methyl-2-(6-phenyl-pyridin-3-yl)-oxazol-4-yl]-ethoxy}-phenyl)-propionic acid

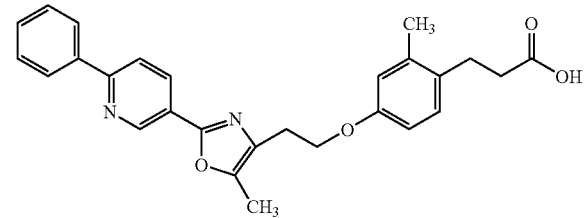

Step A 6-chloro-nicotinic acid 3-methoxycarbonyl-1-methyl-2-oxo-propyl ester

To a solution of 6-Chloro-nicotinic acid (10 g, 63.5 mmol) and 4-Bromo-3-oxo-pentanoic acid methyl ester (1.51 g, 7.2 mmol) (14.6 g, 70 mmol) in acetone (100 mL) is added triethyl amine (9.76 mL, 70 mmol) at 0-5° C. After addition, the reaction mixture is warmed to room temperature and stirred overnight, solid is filtered off, the filtrate is concentrated and taken into methylene chloride, washed with water and brine, dried. The residue is purified by column giving 6-chloro-nicotinic acid 3-methoxycarbonyl-1-methyl-2-oxo-propyl ester (16.3 g.

Step B

[2-(6-Chloro-pyridin-3-yl)-5-methyl-oxazol-4-yl]-acetic acid methyl ester

A mixture of 6-chloro-nicotinic acid 3-methoxycarbonyl-1-methyl-2-oxo-propyl ester (16.3 g, 57.1 mmol) and ammonium acetate (18.5 g, 240 mmol) in ethanol (150 mL) is heated at 80° C. for 2 h, concentrated. The residue is taken into acetic acid (330 mL) and heated to reflux overnight, concentrated. The residue is taken into ethyl acetate and washed with water, dried, concentrated, purified by column giving [2-(6-Chloro-pyridin-3-yl)-5-methyl-oxazol-4-yl]-acetic acid methyl ester (4.3 g).

Step C

2-[2-(6-Chloro-pyridin-3-yl)-5-methyl-oxazol-4-yl]-ethanol

To a solution of [2-(6-Chloro-pyridin-3-yl)-5-methyl-oxazol-4-yl]-acetic acid methyl ester (4.0 g, 15 mmol) from step B in THF (50 mL) is added a solution of lithium aluminum hydride in THF (1.0 M, 12.5 mL, 12.5 mmol) at 0° C. After 1 hr, the reaction is quenched by water and sodium hydroxide, filtered, concentrated. The crude material is used for the next step.

Step D

Toluene-4-sulfonic acid 2-[2-(6-chloro-pyridin-3-yl)-5-methyl-oxazol-4-yl]-ethyl ester The crude 2-[2-(6-Chloro-pyridin-3-yl)-5-methyl-oxazol-4-yl]-ethanol from step C is dissolved in methylene chloride (50 mL), then TsCl, DMAP and triethyl amine are added and stirred overnight. The reaction mixture is washed with water, brine and concentrated. Column chromatography on silica gel gave the title compound (0.5 g).

Step E

3-(4-{2-[2-(6-Chloro-pyridin-3-yl)-5-methyl-oxazol-4-yl]-ethoxy}-2-methyl-phenyl)-propionic acid methyl ester A mixture of toluene-4-sulfonic acid 2-[2-(6-chloro-pyridin-3-yl)-5-methyl-oxazol-4-yl]-ethyl ester (0.4 g, 1.0 mmol, 3-(4-Hydroxy-2-methyl-phenyl)-propionic acid methyl ester (0.2 g, 1 mmol) and Cs2CO3 (0.49 g, 1.5 mmol) in DMF (5 mL) is heated at 60° C. overnight, cooled to room temperature, diluted with ethyl acetate, washed with water and dried. Column chromatography on silica gel gave the product (85 mg).

Step F

3-(2-Methyl-4-{2-[5-methyl-2-(6-phenyl-pyridin-3-yl)-oxazol-4-yl]-ethoxy}-phenyl)-propionic acid methyl ester A mixture of 3-(4-{2-[2-(6-Chloro-pyridin-3-yl)-5-methyl-oxazol-4-yl]-ethoxy}-2-methyl-phenyl)-propionic acid methyl ester (41 mg, 0.1 mmol) and phenyl boronic acid (25 mg, 0.2 mmol) and Na2CO3 (22 mg, 0.2 mmol) in toluene (0.5 mL) and water (0.1 mL) is degassed and filled with nitrogen for three times, then Pd(PPh3)4 (3 mg) is added under nitrogen. The reaction mixture is heated at 90° C. After 12 hrs, the reaction mixture is cooled to room temperature, diluted with ethyl acetate, washed with water, dried, concentrated. Column chromatography on silica gel (Hexane/ethyl acetate as eluent) gave 45 mg of product.

Step G

3-(2-Methyl-4-{2-[5-methyl-2-(6-phenyl-pyridin-3-yl)-oxazol-4-yl]-ethoxy}-phenyl)-propionic acid To a solution of 3-(2-Methyl-4-{2-[5-methyl-2-(6-phenyl-pyridin-3-yl)-oxazol-4-yl]-ethoxy}-phenyl)-propionic acid methyl ester (40 mg) in ethanol (1 mL) is added NaOH (5 N, 1.0 mL), stirred for 2 hr at 50° C., cooled to room temperature, concentrated. The residue is treated with ether and acidified by 5 N HCl, extracted with ether, concentrated. Reversed phase HPLC (water/acetonitrile) gave the title compound (22 mg). MS (ES): 443.3 (M$^+$+1).

The following compound is made in a substantially similar method:

Example 107

3-[4-(2-{2-[6-(2-Fluoro-phenyl)-pyridin-3-yl]-5-methyl-oxazol-4-yl}-ethoxy)-2-methyl-phenyl]-propionic acid

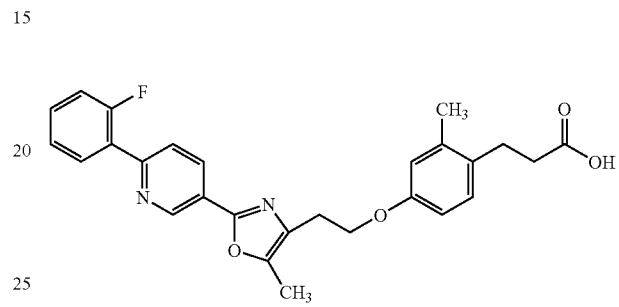

MS (ES): 461.4 (M$^+$+1).

Example 108

3-(2-Methyl-4-{2-[5-methyl-2-(4-pyridin-2-yl-phenyl)-thiazol-4-yl]-ethoxy}-phenyl)-propionic acid

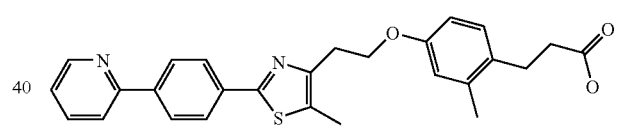

Step A 3-(4-{2-[2-(4-Bromo-phenyl)-5-methyl-thiazol-4-yl]-ethoxy}-2-methyl-phenyl)-propionic acid (100 mg, 0.21 mmol) is dissolved in anhydrous toluene (1 mL), degassed, and filled with nitrogen three times. Palladium tetrakis triphenyl phosphine [Pd(PPh3)4, 21 mg, 0.0021 mmol] is added, and the degassing procedure is repeated. 2-tributylstannylpyridine (63 uL, 0.25 mmol) is then added via syringe and the reaction is heated to reflux. The reaction is monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-(2-Methyl-4-{2-[5-methyl-2-(4-pyridin-2-yl-phenyl)-thiazol-4-yl]-ethoxy}-phenyl)-propionic acid methyl ester is obtained after column chromatography.

Step B

3-(2-Methyl-4-{2-[5-methyl-2-(4-pyridin-2-yl-phenyl)-thiazol-4-yl]-ethoxy}-phenyl)-propionic acid methyl ester from step A is dissolved in tetrahydrofuran (1 mL) and 5N sodium hydroxide (1 mL) solution is added with stirring at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(2-Methyl-4-{2-[5-methyl-2-(4-pyridin-2-yl-phenyl)-thiazol-4-yl]-ethoxy}-phenyl)-propionic acid (46 mg) may also be obtained by recrystalization from ethyl acetate (48% yield 2 steps), MS (ES): 459.2 (M$^+$+1).

The following compounds are made in a similar manner:

Example 109

3-(2-Methyl-4-{2-[5-methyl-2-(4-pyrimidin-2-yl-phenyl)-oxazol-4-yl]-ethoxy}-phenyl)-propionic acid

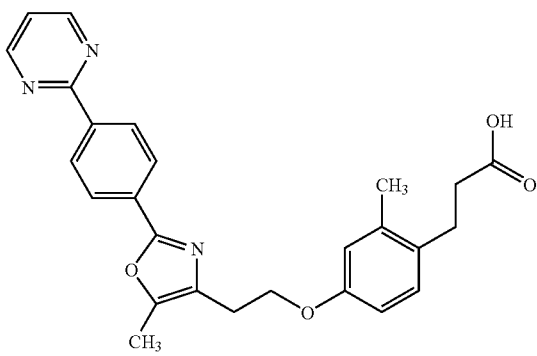

MS (ES): 444.2 (M$^+$+1).

Example 110

3-{4-[2-(2-[2,2']Bipyridinyl-5-yl-5-methyl-oxazol-4-yl)-ethoxy]-2-methyl-phenyl}-propionic acid, bis HCl salt

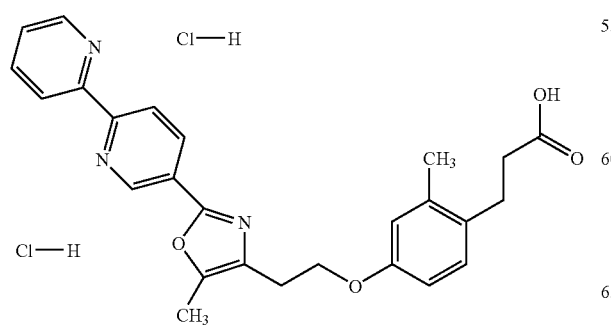

This compound is made in a similar method starting from 6-chloro-nicotinic acid. MS (ES): 444.2 (M$^+$−2 HCl+1).

Example 111

3-(2-Methyl-4-{2-[5-methyl-2-(4-pyridin-2-yl-phenyl)-oxazol-4-yl]-ethoxy}-phenyl)-propionic acid

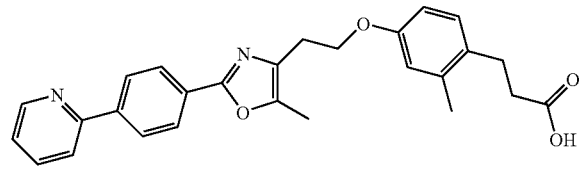

Step A

3-[2-Methyl-4-(2-{5-methyl-2-[4-(4,4,5,5-tetramethyl-[1,3,2]dioxaborolan-2-yl)-phenyl]-oxazol-4-yl}-ethoxy)-phenyl]-propionic acid methyl ester

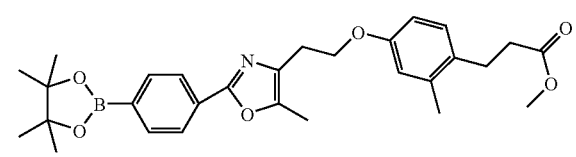

3-(4-{2-[2-(4-Bromo-phenyl)-5-methyl-oxazol-4-yl]-ethoxy}-2-methyl-phenyl)-propionic acid methyl ester (2.0 g, 4.36 mmol) is dissolved in anhydrous methyl sulfoxide (25 mL), degassed, and filled with nitrogen three times. [1,1'-Bis-(diphenylphosphino)ferrocene] dichloropalladium (II) (50 mg) bis(pinacolato)diboron (1.66 g, 6.54 mmol), and potassium acetate (1.71 g, 17.4 mmol) are added, and the degassing procedure is repeated. The reaction is heated to 85° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-[2-Methyl-4-(2-{5-methyl-2-[4-(4,4,5,5-tetramethyl-[1,3,2]dioxaborolan-2-yl)-phenyl]-oxazol-4-yl}-ethoxy)-phenyl]-propionic acid methyl ester (0.9 g) is obtained after column chromatography.

Step B

3-(2-Methyl-4-{2-[5-methyl-2-(4-pyridin-2-yl-phenyl)-oxazol-4-yl]-ethoxy}-phenyl)-propionic acid methyl ester

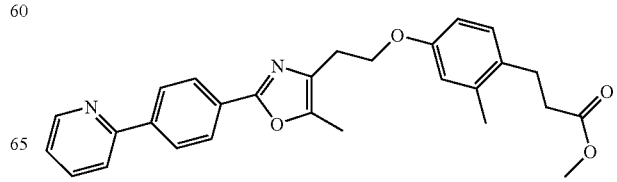

3-[2-Methyl-4-(2-{5-methyl-2-[4-(4,4,5,5-tetramethyl-[1,3,2]dioxaborolan-2-yl)-phenyl]-oxazol-4-yl}-ethoxy)-phenyl]-propionic acid methyl ester (167 mg; 0.328 mmol) is dissolved in anhydrous toluene (1 mL), degassed, and filled with nitrogen three times. [1,1'-Bis-(diphenylphosphino)ferrocene]dichloropalladium(II) (15 mg, 0.02 mmol), 2-bromopyridine (67 ul, 0.7 mmol), and sodium carbonate (150 uL, 10 M aqueous, 1.5 mmol) are added, and the degassing procedure is repeated. The reaction is heated to 100° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated.

Step C 3-(2-Methyl-4-{2-[5-methyl-2-(4-pyridin-2-yl-phenyl)-oxazol-4-yl]-ethoxy}-phenyl)-propionic acid methyl ester from step B is dissolved in tetrahydrofuran (1 mL) and 5N sodium hydroxide (1 mL) solution is added with stirring at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(2-methyl-4-{2-[5-methyl-2-(4-pyridin-2-yl-phenyl)-oxazol-4-yl]-ethoxy}-phenyl)-propionic acid (58 mg, 0.13 mmol, 40% yield for two steps) may also be obtained by recrystalization from ethyl acetate, MS (ES): 443.2 ($M^+$+1).

The following compounds are made in a similar manner:

Example 112

3-(2-Methyl-4-{2-[5-methyl-2-(4-pyridin-4-yl-phenyl)-oxazol-4-yl]-ethoxy}-phenyl)-propionic acid

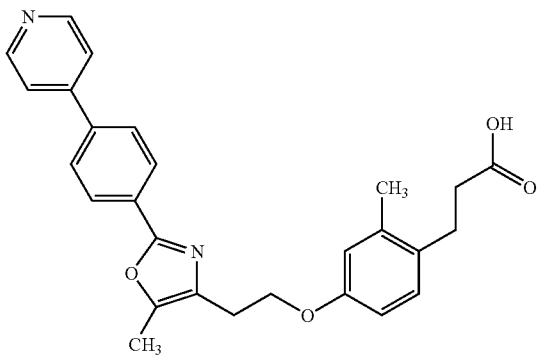

MS (ES): 443.2 ($M^+$+1).

Example 113

3-[2-Methyl-4-(2-{5-methyl-2-[4-(5-methyl-pyridin-2-yl)-phenyl]-oxazol-4-yl}-ethoxy)-phenyl]-propionic acid, trifluoroacetic acid salt

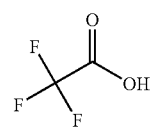

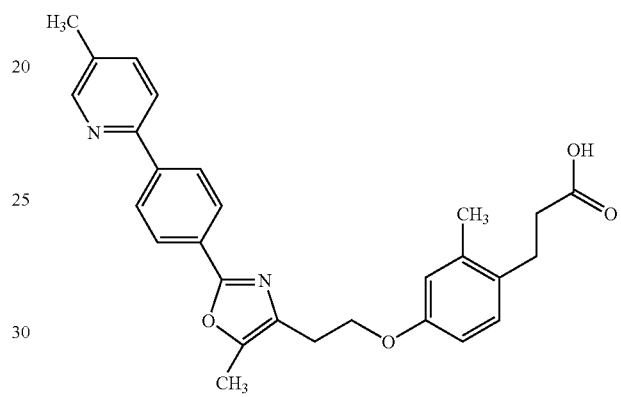

MS (ES): 457.2 ($M^+$+1-TFA).

Example 114

3-[2-Methyl-4-(2-{5-methyl-2-[4-(6-methyl-pyridin-2-yl)-phenyl]-oxazol-4-yl}-ethoxy)-phenyl]-propionic acid, trifluoroacetic acid salt

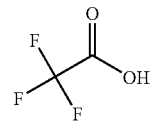

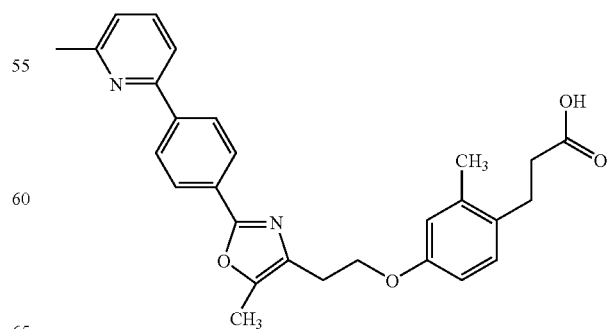

MS (ES): 457.2 ($M^+$+1-TFA).

Example 115

3-[2-Methyl-4-(2-{5-methyl-2-[4-(3-methyl-pyridin-2-yl)-phenyl]-oxazol-4-yl}-ethoxy)-phenyl]-propionic acid

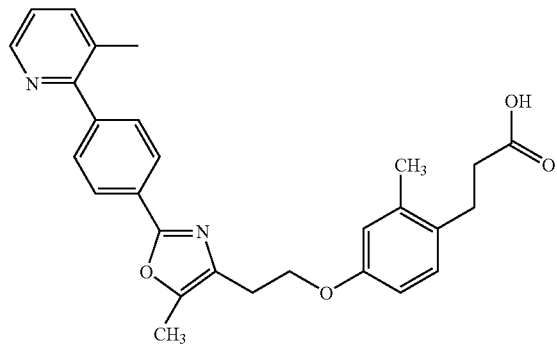

MS (ES): 457.3 (M$^+$+1)

Example 116

3-(2-Methyl-4-{2-[5-methyl-2-(4-pyrimidin-4-yl-phenyl)-oxazol-4-yl]-ethoxy}-phenyl)-propionic acid

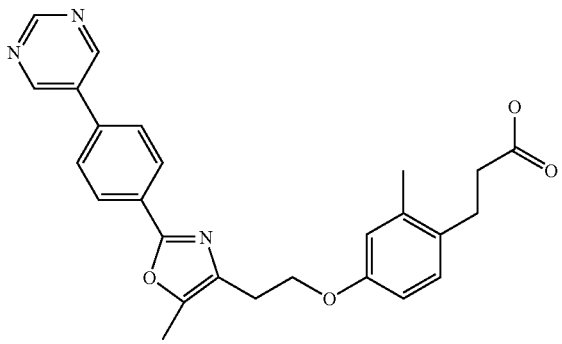

MS (ES): 444.2 (M$^+$+1).

Example 117

3-(2-Methyl-4-{3-[5-methyl-2-(4-pyridin-2-yl-phenyl)-oxazol-4-yl]-propoxy}-phenyl)-propionic acid, HCl salt

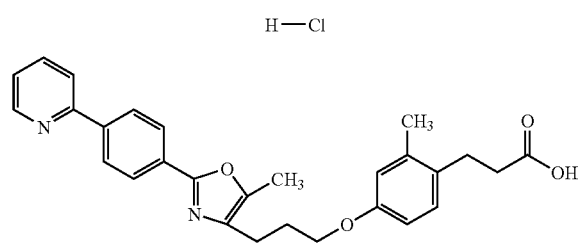

MS (ES): 457.4 (M$^+$+1-HCl).

Example 118

3-[2-Methyl-4-(2-{5-methyl-2-[3-(5-methyl-pyridin-2-yl)-phenyl]-oxazol-4-yl}-ethoxy)-phenyl]-propionic acid, trifluoroacetic acid salt

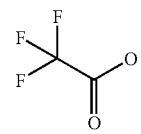

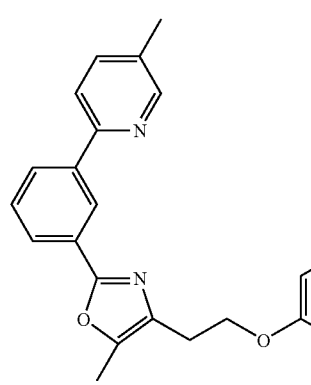

MS (ES): 457.2 (M$^+$+1-TFA).

Example 119

3-[2-Methyl-4-(2-{5-methyl-2-[3-(6-methyl-pyridin-2-yl)-phenyl]-oxazol-4-yl}-ethoxy)-phenyl]-propionic acid, trifluoroacetic acid salt

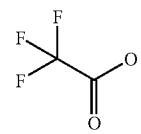

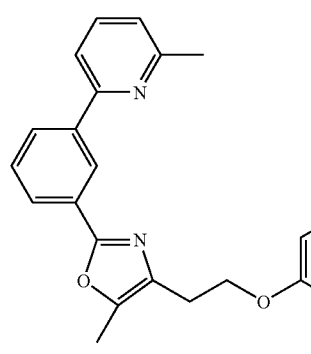

MS (ES): 457.2 (M$^+$+1-TFA).

Example 120

3-[2-Methyl-4-(2-{5-methyl-2-[3-pyridin-2-yl-phenyl]-oxazol-4-yl}-ethoxy)-phenyl]-propionic acid, trifluoroacetic acid salt

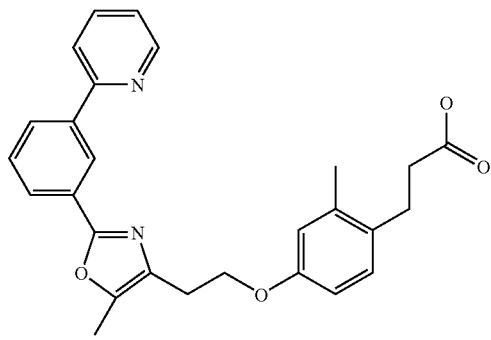

MS (ES): 443.2 (M$^+$+1-TFA).

Example 121

3-(2-Methyl-4-{2-[5-methyl-2-(3-pyrimidin-4-yl-phenyl)-oxazol-4-yl]-ethoxy}-phenyl)-propionic acid

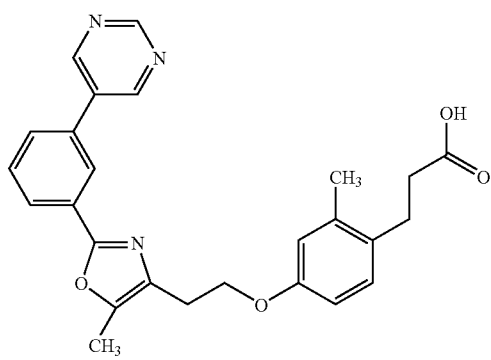

MS (ES): 444.2 (M$^+$+1).

Example 122

3-(2-Methyl-4-{2-[5-methyl-2-(3-pyrimidin-2-yl-phenyl)-oxazol-4-yl]-ethoxy}-phenyl)-propionic acid

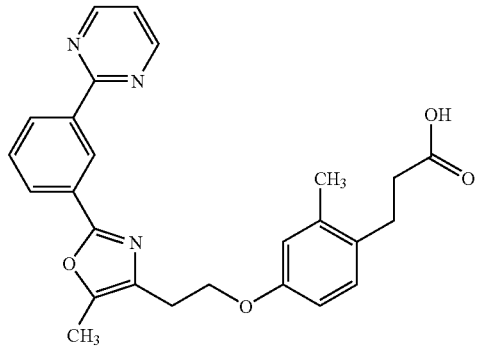

MS (ES): 444.2 (M$^+$+1).

Example 123

3-(2-Methyl-4-{2-[5-methyl-2-(4-pyrimidin-2-yl-phenyl)-thiazol-4-yl]-ethoxy}-phenyl)-propionic acid

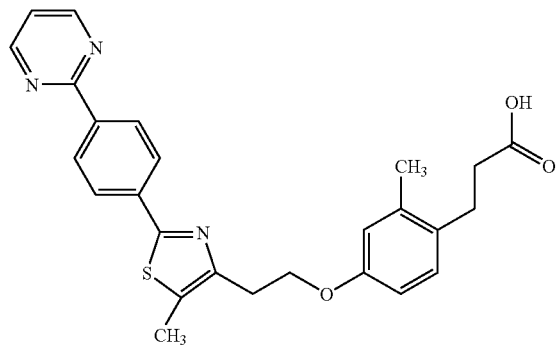

MS (ES) 460.0 (M$^+$+1).

Example 124

3-(2-Methyl-4-{2-[5-methyl-2-(4-pyrazin-2-yl-phenyl)-thiazol-4-yl]-ethoxy}-phenyl)-propionic acid

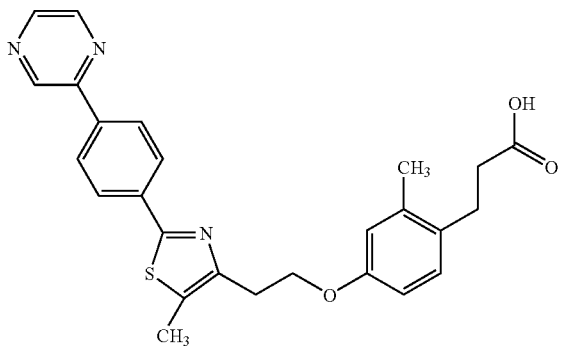

MS (ES): 460.2 (M$^+$+1).

Example 125

3-(2-Methyl-4-{2-[5-methyl-2-(4-pyrazin-2-yl-phenyl)-oxazol-4-yl]-ethoxy}-phenyl)-propionic acid

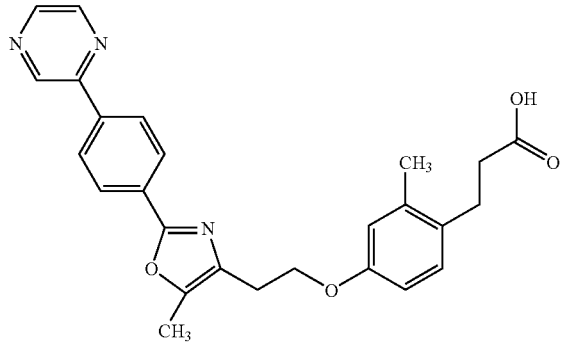

MS (ES): 444.2 (M$^+$+1).

Example 126

3-(2-Methyl-4-{2-[5-methyl-2-(3-pyrazin-2-yl-phenyl)-oxazol-4-yl]-ethoxy}-phenyl)-propionic acid

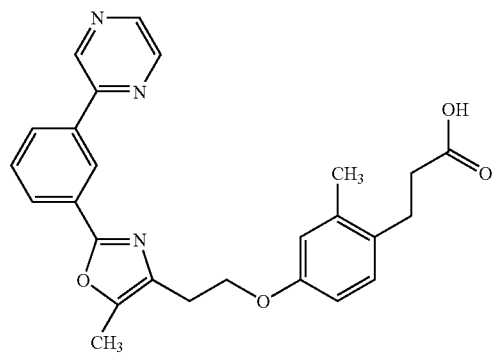

MS (ES): 444.2 (M$^+$+1).

Example 127

3-[2-Methyl-4-(2-{5-methyl-2-[4-(6-methyl-pyridazin-3-yl)-phenyl]-oxazol-4-yl}-ethoxy)-phenyl]-propionic acid

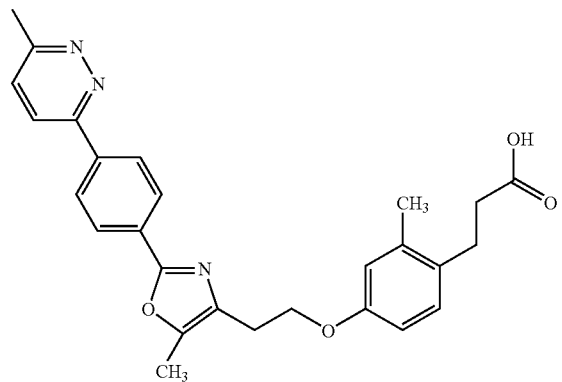

MS (ES): 458.2 (M$^+$+1).

Example 128

3-(2-Methyl-4-{2-[5-methyl-2-(3-pyrazin-2-yl-phenyl)-oxazol-4-yl]-ethoxy}-phenyl)-propionic acid

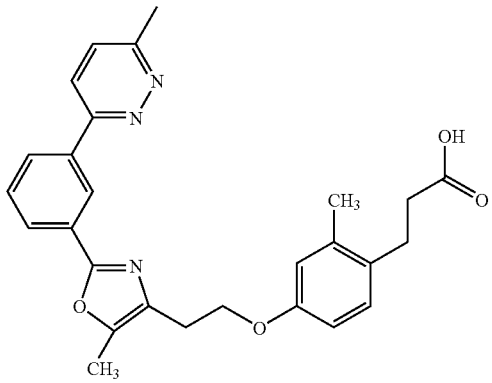

MS (ES): 458.2 (M$^+$+1).

Example 129

3-(2-Methyl-4-{2-[5-methyl-2-(4-pyridin-3-yl-phenyl)-thiazol-4-yl]-ethoxy}-phenyl)-propionic acid

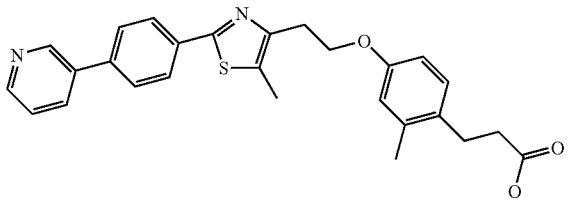

Step A 3-(4-{2-[2-(4-Bromo-phenyl)-5-methyl-thiazol-4-yl]-ethoxy}-2-methyl-phenyl)-propionic acid methyl ester (100 mg, 0.200 mmol) is dissolved in toluene (1 mL), degassed, and filled with nitrogen three times. Palladium tetrakistriphenyl phosphine (10 mg, 0.010 mmol), 3-pyridylboronic acid (31 mg, 0.250 mmol), and sodium carbonate (100 uL of a 10M solution, 0.400 mmol) are added, and the degassing procedure is repeated. Ethanol (1 mL) is added to dissolve the boronic acid. The reaction is heated to 100° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-(2-Methyl-4-{2-[5-methyl-2-(4-pyridin-3-yl-phenyl)-thiazol-4-yl]-ethoxy}-phenyl)-propionic acid methyl ester (47 mg, 0.100 mmol) is obtained after column chromatography (50% yield).

Step B 3-(2-Methyl-4-{2-[5-methyl-2-(4-pyridin-3-yl-phenyl)-thiazol-4-yl]-ethoxy}-phenyl)-propionic acid methyl ester (47 mg, 0.100 mmol) is dissolved in tetrahydrofuran (1 mL) and 5N sodium hydroxide (1 mL) solution is added at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(2-Methyl-4-{2-[5-methyl-2-(4-pyridin-3-yl-phenyl)-thiazol-4-yl]-ethoxy}-phenyl)-propionic acid (40 mg, 0.087 mmol) may also be obtained by recrystalization from ethyl acetate (87% yield). MS (ES): 459.2 ($M^+ +1$). Alternatively, the acid may be obtained after reversed phase preparative HPLC as the hydrochloride salt.

The following compounds are made in a similar manner:

Example 130

3-(2-Methyl-4-{2-[5-methyl-2-(4-pyridin-4-yl-phenyl)-thiazol-4-yl]-ethoxy}-phenyl)-propionic acid

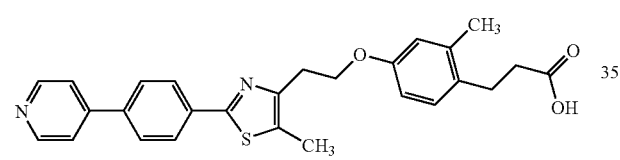

MS (ES): 459.2 ($M^+ +1$).

Example 131

3-(2-Methyl-4-{2-[5-methyl-2-(4-pyridin-3-yl-phenyl)-oxazol-4-yl]-ethoxy}-phenyl)-propionic acid

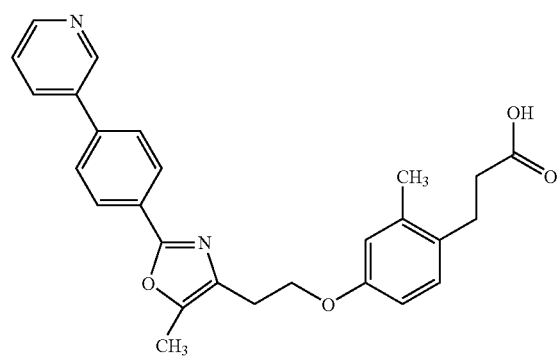

MS (ES): 443.2 ($M^+ +1$).

Example 132

3-(2-Methyl-4-{2-[5-methyl-2-(3-pyridin-3-yl-phenyl)-oxazol-4-yl]-ethoxy}-phenyl)-propionic acid

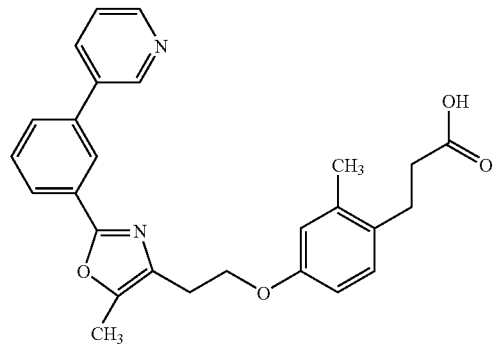

MS (ES): 443.2 ($M^+ +1$).

Example 133

3-(2-Methyl-4-{2-[5-methyl-2-(3-pyridin-4-yl-phenyl)-oxazol-4-yl]-ethoxy}-phenyl)-propionic acid

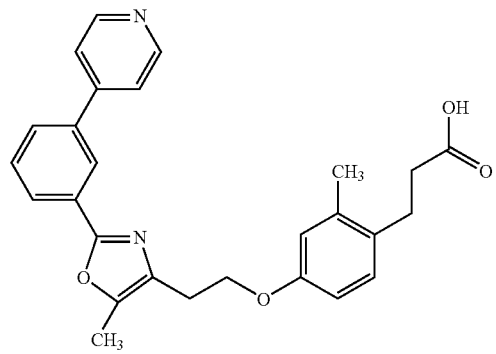

MS (ES): 443.2 ($M^+ +1$).

Biological Assays

Binding and Cotransfection Studies

The in vitro potency of compounds in modulating PPAR receptors are determined by the procedures detailed below. DNA-dependent binding (ABCD binding) is carried out using SPA technology with PPAR receptors. Tritium-labeled PPAR selective agonists are used as radioligands for generating displacement curves and $IC_{50}$ values with compounds of the invention. Cotransfection assays are carried out in CV-1 cells. The reporter plasmid contained an acyl-CoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 µM). These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα. The binding and cotransfection efficacy values found, for compounds of the invention and compounds of this invention which are useful for modulating a PPAR alpha receptor, are $\leq 100$ nM and $\geq 50\%$, respectively.

Binding Assay:

DNA-dependent binding is carried out using Scintillation Proximity Assay (SPA) technology (Amersham Pharmacia Biotech). PPARγ, PPARα and PPARδ receptors as well as their heterodimer partner RXRα receptor are prepared using a baculovirus expression system. Biotinylated oligonucleotide 5'TAATGTAGGTAATAGTTCAATAGGT-CAAAGGG3' is used for binding of receptor dimers to Yttrium silicate streptavidin-coated SPA beads. PPARγ labeled ligand is $^3$H-reference, and PPARα and PPARδ•labeled ligands is $^3$H-reference with specific activity of 52 Ci/mmol and 90 Ci/mmol, respectively. Competition binding reactions are carried out in 10 mM HEPES pH 7.8, 80 mM KCl, 0.5 mM MgCl$_2$, 1 mM DTT, 0.5% CHAPS, 14% glycerol, using 2.5 µg of each of PPARγ, α or δ and RXRα receptors, 5 nM to 10 µM of competing compounds and 30,000 cpm of corresponding labeled ligand.

Co-transfection Assay:

Co-transfection assays are performed in CV-1 cells using calcium phosphate coprecipitation as previously described (Berger et al. Steroid Biochem. Mol. Biol. 41:733, 1992; Mukherjee et al. Nature 386:407-410, 1997). The reporter plasmid contained an acylCoA oxidase (AOX) PPRE and TK promoter upstream of the luciferase reporter cDNA. PPARs and RXRα are constitutively expressed using plasmids containing the CMV promoter. For PPARα•or•δ, interference by endogenous PPARs in CV-1 cells is eliminated by using a GAL4 chimeric system in which the DNA binding domain of the transfected PPARαor•δ is replaced by that of GAL4, and the GAL4 response element is utilized in place of the AOX PPRE. CV-1 cells are transfected in T225 cm$^2$ flasks in DMEM with 10% Fetal Bovine Serum (FBS). After an overnight incubation, transfected cells are trypsinized and plated in 96 well dishes in DMEM media containing 10% charcoal-stripped FBS. After a 6 h incubation, cells are exposed to 0.1 nM to 10 µM of test compounds. Co-transfection efficacy is determined using reference compounds. Compounds of this invention that are selective for the PPARδ are at least 10-fold selective for PPAR•• over PPARα and PPARγ.

Evaluation of Triglyceride Reduction and HDL Cholesterol Elevation in HuapoAI Transgenic Mice Seventeen different series of studies are performed to evaluate the effect of compounds of the present invention upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO$_2$ and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542, 1983; Allain C. C. et al., Clin Chem 20:470-475, 1974. Commercially available standards for triglycerides and total cholesterol, respectively, commercial quality control plasma, and samples are measured in duplicate using 200 µl of reagent. An additional aliquot of sample, added to a well containing 200 µl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (for example, Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is compared to Mice Receiving the Vehicle to identify compounds that could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels.

Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of five different compounds of the present invention and the PPAR gamma agonist rosiglitazone or the PPAR alpha agonist fenofibrate, and the control, to male db/db mice, are studied.

Five week old male diabetic (db/db) mice [for example, C57BlKs/j-m +/+ Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24 hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific calorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

The results of the study, suggest compounds of the present invention that significantly reduced db/db mouse plasma glucose levels while resulting in body weight gains that are generally less than those observed for rosiglitazone.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealed a significant reduction in respiratory quotient (RQ) in treated animals during the dark cycle [0.864±0.013 (Control) vs. 0.803±0.007 (Treated); p<0.001]. This reduction in RQ is indicative of an increased utilization of fat during the animals' active (dark) cycle. Additionally, treated animals displayed significantly higher rates of energy expenditure than control animals (17.40±0.49 vs. 13.62±0.26 kcal/kg/hr, respectively).

Male KK/$A^y$ Mice

Male KK/$A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention that may be especially desired.

Method to Elucidate the LDL-cholesterol Total-cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow had a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster receives once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. The LDL-lowering efficacy for certain compounds of this invention is markedly more potent than that of fenofibrate. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired.

Method to Elucidate the Fibrinogen-Lowering Effect of PPAR•Modulators

Zucker Fatty Rat Model:

The life phase of the study on fibrinogen-lowering effect of compounds of this invention is part of the life phase procedures for the antidiabetic studies of the same compounds. On the last (14th) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitores the clotting time, a function of fibrinogen concentration quantified with reference to standard samples.

Results:

Compounds of this invention are capable of lowering fibrinogen level in vivo. Compounds that lower fibrinogen level greater than vehicle can be especially desired.

Cholesterol and triglyceride lowering effects of compounds of this invention are also produced in Zucker rats.

Method to Elucidate the Anti-body Weight Gain and Anti-appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Test compounds are dissolved in an aqueous vehicle such that each rat receives once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Using this assay, compounds of this invention are found to result in significant weight reduction.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the Formula I:

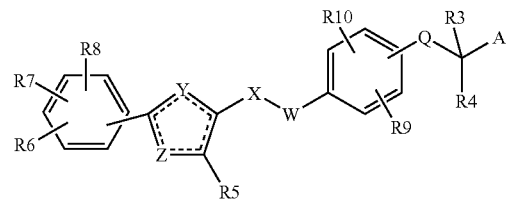

and pharmaceutically acceptable salts thereof, wherein:
(a) R3 is hydrogen;
(b) R4 is hydrogen;
(c) R5 is selected from the group consisting of ($C_1$-$C_6$) alkyl, ($C_1$-$C_6$) alkenyl, aryl($C_0$-$C_4$)alkyl, aryloxy($C_0$-$C_4$)alkyl, arylthio($C_0$-$C_4$)alkyl, wherein said aryl($C_0$-$C_4$)alkyl, aryloxy($C_0$-$C_4$)alkyl, and arylthio($C_0$-$C_4$) alkyl are each independently optionally substituted with from one to three substituents each independently selected from R5';
(d) R5' are each independently selected from the group consisting of halo, —(O)—($C_1$-$C_5$)alkylCOOH, $C_1$-$C_5$ alkyl, $C_1$-$C_5$ alkylCOOH, and $CF_3$;
(e) R6 is selected from the group consisting of, optionally substituted pyridinyl, optionally substituted pyrimidinyl, and optionally substituted pyrazinyl wherein said substituted pyridinyl, pyrimidinyl, and pyrazinyl are substituted with from one to three substituents independently selected from R6';
(f) R6' is independently selected from the group consisting of $CF_3$, $C_1$-$C_4$ alkyl, halo, hydroxy($C_1$-$C_3$)alkyl, $C_1$-$C_3$ alkoxy, and —C(O)$CH_3$;
(g) R7 and R8 are each independently selected from the group consisting of hydrogen, ($C_1$-$C_6$) alkyl, and trifluoromethyl;
(h) R9 and R10 are each independently selected from the group consisting of hydrogen, ($C_1$-$C_4$) alkyl, ($C_1$-$C_3$) alkenyl, halo, and ($C_1$-$C_4$) alkoxy;
(i) Q is selected from the group consisting of O, C, and a single bond;
(j) W is selected from the group consisting of O, S, and $SO_2$;
(k) X is $C_mH_{2m}$;
(l) m is selected from the group consisting of 0, 1 and 2;
(m) Y and Z are each independently selected from the group consisting of N, S, and O, with the proviso that at least one of Y and Z is selected from the group consisting of S and O;
(n) A is COOH;
(o) n is 0, 1, 2 or 3;
(p) R19 is selected from the group consisting of hydrogen, C1-C4alkyl and arylmethyl, wherein said alky and arylmethyl are each optionally substituted with from one to three substituents each independently selected from R19'; and
(q) R19' are each independently selected from the group consisting of halo, —(O)—($C_1$-$C_5$)alkylCOOH, $C_1$-$C_5$ alkyl, and $CF_3$;
with the proviso that when R3 and R4 are each hydrogen, and at least one selected from the group consisting of R7 and R8 is $CF_3$, then R5 is selected from the group consisting of ($C_3$-$C_6$) alkyl, ($C_1$-$C_6$) alkenyl, substituted aryl($C_0$-$C_4$)alkyl, substituted aryloxy($C_0$-$C_4$) alkyl, substituted arylthio($C_0$-$C_4$)alkyl, unsubstituted aryl($C_0$-$C_4$)alkyl, unsubstituted aryloxy($C_0$-$C_4$)alkyl, and unsubstituted arylthio($C_0$-$C_4$)alkyl.

2. A compound as claimed by claim 1 wherein W is O.
3. A compound as claimed by claim 1 wherein W is S.
4. A compound as claimed by claim 1 wherein W is bonded to the phenyl meta in relation to Q.
5. A compound as claimed by claim 1 wherein R5 is ($C_1$-$C_3$)alkyl.
6. A compound as claimed by claim 1 wherein R5 is methyl.
7. A compound as claimed by claim 1 wherein R5 is an optionally substituted group selected from aryl($C_0$-$C_4$)alkyl, aryloxy($C_0$-$C_4$)alkyl, and arylthio($C_0$-$C_4$)alkyl.
8. A compound as claimed by claim 1 wherein R5 is optionally substituted phenyl-alkyl.
9. A compound as claimed by claim 1 wherein Z is N.
10. A compound as claimed by claim 1 wherein Y is O.
11. A compound as claimed by claim 1 wherein Y is S.
12. A pharmaceutical composition, comprising a pharmaceutically acceptable carrier and at least one compound as claimed by claim 1.
13. A method of modulating a peroxisome proliferator activated receptor, comprising the step of contacting the receptor with at least one compound as claimed by claim 1.
14. A method of claim 13 wherein the PPAR modulator is a PPAR agonist.
15. A method of treating diabetes mellitus in a mammal, comprising the step of administering to the mammal in need thereof, a therapeutically effective amount of at least one compound of claim 1.
16. A method of treating atherosclerosis in a mammal, comprising the step of administering to the mammal in need thereof, a therapeutically effective amount of at least one compound of claim 1.
17. A compound as claimed by claim 1 wherein the compound is radiolabeled.
18. A compound as claimed by claim 1 wherein the compound is selected from the group consisting of:
3-[4-(2-{2-[6-(2-Fluoro-phenyl)-pyridin-3-yl]-5-methyl-thiazol-4-yl}-ethoxy)-2-methyl-phenyl]-propionic acid,
3-[4-(2-{2-[6-(3-Fluoro-phenyl)-pyridin-3-yl]-5-methyl-thiazol-4-yl}-ethoxy)-2-methyl-phenyl]-propionic acid,
3-[4-(2-{2-[6-(4-Fluoro-phenyl)-pyridin-3-yl]-5-methyl-thiazol-4-yl}-ethoxy)-2-methyl-phenyl]-propionic acid,
3-[4-(2-{2-[6-phenyl-pyridin-3-yl]-5-methyl-thiazol-4-yl}-ethoxy)-2-methyl-phenyl]-propionic acid,
3-[4-(2-{2-[6-(2-methyl-phenyl)-pyridin-3-yl]-5-methyl-thiazol-4-yl}-ethoxy)-2-methyl-phenyl]-propionic acid,
3-[4-(2-{2-[6-(3-methyl-phenyl)-pyridin-3-yl]-5-methyl-thiazol-4-yl}-ethoxy)-2-methyl-phenyl]-propionic acid,
3-[4-(2-{2-[6-(4-methyl-phenyl)-pyridin-3-yl]-5-methyl-thiazol-4-yl}-ethoxy)-2-methyl-phenyl]-propionic acid,
3-{4-[2-(2-[2,2']Bipyridinyl-5-yl-5-methyl-thiazol-4-yl)-ethoxy]-2-methyl-phenyl}-propionic acid,
3-(2-Methyl-4-{2-[5-methyl-2-(6-phenoxy-pyridin-3-yl)-thiazol-4-yl]-ethoxy}-phenyl)-propionic acid,
3-(2-Methyl-4-{2-[5-methyl-2-(6-phenoxy-pyridin-3-yl)-oxazol-4-yl]-ethoxy}-phenyl)-propionic acid,
3-(2-Methyl-4-{2-[5-methyl-2-(6-phenylsulfanyl-pyridin-3-yl)-oxazol-4-yl]-ethoxy}-phenyl)-propionic acid,
3-(2-Methyl-4-{2-[5-methyl-2-(6-phenyl-pyridin-3-yl)-oxazol-4-yl]-ethoxy}-phenyl)-propionic acid,
6-chloro-nicotinic acid 3-methoxycarbonyl-1-methyl-2-oxo-propyl ester,
3-[4-(2-{2-[6-(2-Fluoro-phenyl)-pyridin-3-yl]-5-methyl-oxazol-4-yl}-ethoxy)-2-methyl-phenyl]-propionic acid,
3-(2-Methyl-4-{2-[5-methyl-2-(4-pyridin-2-yl-phenyl)-thiazol-4-yl]-ethoxy}-phenyl)-propionic acid,
3-(2-Methyl-4-{2-[5-methyl-2-(4-pyrimidin-2-yl-phenyl)-oxazol-4-yl]-ethoxy}-phenyl)-propionic acid,
3-{4-[2-(2-[2,2']Bipyridinyl-5-yl-5-methyl-oxazol-4-yl)-ethoxy]-2-methyl-phenyl}-propionic acid, 3-(2-Methyl-4-{2-[5-methyl-2-(4-pyridin-2-yl-phenyl)-oxazol-4-yl]-ethoxy}-phenyl)-propionic acid,
3-(2-Methyl-4-{2-[5-methyl-2-(4-pyridin-4-yl-phenyl)-oxazol-4-yl]-ethoxy}-phenyl)-propionic acid,
3-[2-Methyl-4-(2-{5-methyl-2-[4-(5-methyl-pyridin-2-yl)-phenyl]-oxazol-4-yl}-ethoxy)-phenyl]-propionic acid,
3-[2-Methyl-4-(2-{5-methyl-2-[4-(6-methyl-pyridin-2-yl)-phenyl]-oxazol-4-yl}-ethoxy)-phenyl]-propionic acid,
3-[2-Methyl-4-(2-{5-methyl-2-[4-(3-methyl-pyridin-2-yl)-phenyl]-oxazol-4-yl}-ethoxy)-phenyl]-propionic acid,
3-(2-Methyl-4-{2-[5-methyl-2-(4-pyrimidin-4-yl-phenyl)-oxazol-4-yl]-ethoxy}-phenyl)-propionic acid,
3-(2-Methyl-4-{3-[5-methyl-2-(4-pyridin-2-yl-phenyl)-oxazol-4-yl]-propoxy}-phenyl)-propionic acid,
3-[2-Methyl-4-(2-{5-methyl-2-[3-(5-methyl-pyridin-2-yl)-phenyl]-oxazol-4-yl}-ethoxy)-phenyl]-propionic acid,
3-[2-Methyl-4-(2-{5-methyl-2-[3-(6-methyl-pyridin-2-yl)-phenyl]-oxazol-4-yl}-ethoxy)-phenyl]-propionic acid,
3-[2-Methyl-4-(2-{5-methyl-2-[3-pyridin-2-yl-phenyl]-oxazol-4-yl}-ethoxy)-phenyl]-propionic acid,
3-(2-Methyl-4-{2-[5-methyl-2-(3-pyrimidin-4-yl-phenyl)-oxazol-4-yl]-ethoxy}-phenyl)-propionic acid,
3-(2-Methyl-4-{2-[5-methyl-2-(3-pyrimidin-2-yl-phenyl)-oxazol-4-yl]-ethoxy}-phenyl)-propionic acid,
3-(2-Methyl-4-{2-[5-methyl-2-(4-pyrimidin-2-yl-phenyl)-thiazol-4-yl]-ethoxy}-phenyl)-propionic acid,
3-(2-Methyl-4-{2-[5-methyl-2-(4-pyrazin-2-yl-phenyl)-thiazol-4-yl]-ethoxy}-phenyl)-propionic acid,
3-(2-Methyl-4-{2-[5-methyl-2-(4-pyrazin-2-yl-phenyl)-oxazol-4-yl]-ethoxy}-phenyl)-propionic acid,
3-(2-Methyl-4-{2-[5-methyl-2-(3-pyrazin-2-yl-phenyl)-oxazol-4-yl]-ethoxy}-phenyl)-propionic acid,
3-[2-Methyl-4-(2-{5-methyl-2-[4-(6-methyl-pyridazin-3-yl)-phenyl]-oxazol-4-yl}-ethoxy)-phenyl]-propionic acid,
3-(2-Methyl-4-{2-[5-methyl-2-(3-pyrazin-2-yl-phenyl)-oxazol-4-yl]-ethoxy}-phenyl)-propionic acid,
3-(2-Methyl-4-{2-[5-methyl-2-(4-pyridin-3-yl-phenyl)-thiazol-4-yl]-ethoxy}-phenyl)-propionic acid,
3-(2-Methyl-4-{2-[5-methyl-2-(4-pyridin-4-yl-phenyl)-thiazol-4-yl]-ethoxy}-phenyl)-propionic acid,
3-(2-Methyl-4-{2-[5-methyl-2-(4-pyridin-3-yl-phenyl)-oxazol-4-yl]-ethoxy}-phenyl)-propionic acid,
3-(2-Methyl-4-{2-[5-methyl-2-(3-pyridin-3-yl-phenyl)-oxazol-4-yl]-ethoxy}-phenyl)-propionic acid, and
3-(2-Methyl-4-{2-[5-methyl-2-(3-pyridin-4-yl-phenyl)-oxazol-4-yl]-ethoxy}-phenyl)-propionic acid.

19. A compound selected from the group consisting of:
(3-{2-[5-Ethyl-2-(4-trifluoromethyl-phenyl)-thiazol-4-yl]-ethoxy}-phenyl)-acetic acid,
(3-{2-[5-Ethyl-2-(4-trifluoromethyl-phenyl)-thiazol-4-yl]-ethoxy}-phenyl)-acetic acid,
(3-{2-[5-Propyl-2-(4-trifluoromethyl-phenyl)-thiazol-4-yl]-ethoxy}-phenyl)-acetic acid,
(4-{2-[4-Isopropyl-2-(4-trifluoromethyl-phenyl)-oxazol-5-yl]-ethoxy}-2-methyl-phenyl)-acetic acid,
(3-{2-[4-Isopropyl-2-(4-trifluoromethyl-phenyl)-oxazol-5-yl]-ethoxy}-phenyl)-acetic acid,
{3-[4-Isopropyl-2-(4-trifluoromethyl-phenyl)-oxazol-5-ylmethoxy]-phenyl}-acetic acid,
{3-[4-Isopropyl-2-(4-trifluoromethyl-phenyl)-oxazol-5-ylmethylsulfanyl]-phenyl}-acetic acid,
(3-{2-[4-Isopropyl-2-(4-trifluoromethyl-phenyl)-oxazol-5-yl]-ethylsulfanyl}-phenyl)-acetic acid,
{3-[4-Isopropyl-2-(4-trifluoromethyl-phenyl)-thiazol-5-ylmethoxy]-phenyl}-acetic acid,
{4-[4-Methyl-2-(4-trifluoromethyl-phenyl)-thiazol-5-ylmethylsulfanyl]-2-propyl-phenoxy}-acetic acid, 3-{4-Ethyl-2-(4-trifluoromethyl-phenyl)-thiazol-5-ylmethoxy]-2-methyl-phenyl}-propionic acid,
3-{4-[4-Butyl-2-(4-trifluoromethyl-phenyl)-thiazol-5-ylmethoxy]-2-methyl-phenyl}-propionic acid,
3-{4-[4-Ethyl-2-(4-trifluoromethyl-phenyl)-thiazol-5-ylmethylsulfanyl]-2-methyl-phenyl}-propionic acid,
3-{2-Methyl-4-[4-propyl-2-(4-trifluoromethyl-phenyl)-thiazol-5-ylmethylsulfanyl]-phenyl}-propionic acid,
3-{2-Methyl-4-[4-phenethyl-2-(4-trifluoromethyl-phenyl)-thiazol-5-ylmethylsulfanyl]-phenyl}-propionic acid,
3-{2-Methyl-4-[4-phenethyl-2-(4-trifluoromethyl-phenyl)-thiazol-5-ylmethoxy]-phenyl}-propionic acid,
3-{2-Methyl-4-[4-propyl-2-(4-trifluoromethyl-phenyl)-thiazol-5-ylmethoxy]-phenyl}-propionic acid,
3-{4-[4-Isopropyl-2-(4-trifluoromethyl-phenyl)-thiazol-5-ylmethoxy]-2-methyl-phenyl}-propionic acid,
3-{4-[4-Isopropyl-2-(4-trifluoromethyl-phenyl)-thiazol-5-ylmethylsulfanyl]-2-methyl-phenyl}-propionic acid,
3-{4-[4-[2-(2-Chloro-6-fluoro-phenyl)-ethyl]-2-(4-trifluoromethyl-phenyl)-thiazol-5-ylmethoxy]-2-methyl-phenyl}-propionic acid,
3-{2-Methyl-4-[4-phenylsulfanylmethyl-2-(4-trifluoromethyl-phenyl)-thiazol-5-ylmethoxy]-phenyl}-propionic acid,
3-{4-[4-(2-Chloro-6-fluoro-phenoxymethyl)-2-(4-trifluoromethyl-phenyl)-thiazol-5-ylmethoxy]-2-methyl-phenyl}-propionic acid,
3-{2-Methyl-4-[4-phenoxymethyl-2-(4-trifluoromethyl-phenyl)-thiazol-5-ylmethoxy]-phenyl}-propionic acid,
3-{4-[4-(3,5-Bis-trifluoromethyl-phenoxymethyl)-2-(4-trifluoromethyl-phenyl)-thiazol-5-ylmethoxy]-2-methyl-phenyl}-propionic acid,
3-{4-[4-Ethyl-2-(4-trifluoromethyl-phenyl)-thiazol-5-ylmethoxy]-2-methoxy-phenyl}-propionic acid,
3-{4-[4-Ethyl-2-(4-trifluoromethyl-phenyl)-thiazol-5-ylmethoxy]-phenyl}-propionic acid,
3-{2-Methyl-4-[4-phenoxymethyl-2-(4-trifluoromethyl-phenyl)-thiazol-5-ylmethylsulfanyl]-phenyl}-propionic acid,
3-{4-[4-[2-(2-Chloro-6-fluoro-phenyl)-ethyl]-2-(4-trifluoromethyl-phenyl)-thiazol-5-ylmethylsulfanyl]-2-methyl-phenyl}-propionic acid,
3-{2-Methyl-4-[4-phenoxymethyl-2-(4-trifluoromethyl-phenyl)-thiazol-5-ylmethylsulfanyl]-phenyl}-propionic acid,
3-{2-Methyl-4-[4-phenylsulfanylmethyl-2-(4-trifluoromethyl-phenyl)-thiazol-5-ylmethylsulfanyl]-phenyl}-propionic acid,
3-(2-Methyl-4-{2-[5-propyl-2-(4-trifluoromethyl-phenyl)-thiazol-4-yl]-ethoxy}-phenyl)-propionic acid,
3-(2-Methyl-4-{2-[5-propyl-2-(4-trifluoromethyl-phenyl)-thiazol-4-yl]-ethylsulfanyl}-phenyl)-propionic acid,
3-{4-[4-Ethyl-2-(4-trifluoromethyl-phenyl)-oxazol-5-ylmethoxy]-2-methyl-phenyl}-propionic acid, 3-(2-Methyl-4-{[5-methyl-2-(4-trifluoromethyl-phenyl)-oxazol-4-ylmethyl]-carbamoyl}-phenyl)-propionic acid, 3-(4-{[4-Isopropyl-2-(4-trifluoromethyl-phenyl)-thiazole-5-carbonyl]-amino}-2-methyl-phenyl)-propionic acid, 3-(4-{2-[5-Ethyl-2-(4-trifluoromethyl-phenyl)-thiazol-4-yl]-acetylamino}-2-methyl-phenyl)-propionic acid, 3-[4-({[4-Isopropyl-2-(4-trifluoromethyl-phenyl)-thiazole-5-carbonyl]-methyl-amino}-methyl)-2-methyl-phenyl]-propionic acid, 3-[4-({[4-Isopropyl-2-(4-trifluoromethyl-phenyl)-thiazole-5-carbonyl]-amino}-methyl)-2-methyl-phenyl]-propionic acid, 3-(2-Methyl-4-{[4-methyl-2-(4-trifluoromethyl-phenyl)-thiazol-5-ylmethyl]-amino}-phenyl)-propionic acid, 3-[4-({Bis-[4-methyl-2-(4-trifluoromethyl-phenyl)-thiazol-5-ylmethyl]-amino}-methyl)-2-methyl-phenyl]-propionic acid TFA salt, 3-[2-Methyl-4-({methyl-[4-methyl-2-(4-trifluoromethyl-phenyl)-thiazol-5-ylmethyl]-amino}-methyl)-phenyl]-propionic acid methyl ester TFA salt, 3-(4-{Methoxycarbonyl-[4-methyl-2-(4-trifluoromethyl-phenyl)-thiazol-5-ylmethyl]-amino}-2-methyl-phenyl)-propionic acid, 3-{2-Methyl-4-[4-methyl-2-(4-trifluoromethyl-phenyl)-thiazol-5-ylmethoxymethyl]-phenyl}-propionic acid, 3-{4-[4-Isopropyl-2-(4-trifluoromethyl-phenyl)-thiazol-5-ylmethoxymethyl]-2-methyl-phenyl}-propionic acid, and {3-[5-Methyl-2-(4-trifluoromethyl-phenyl)-oxazol-4-ylmethoxy]-phenyl}-acetic acid.

20. A compound as claimed by claim 1 wherein Q is C.
21. A compound as claimed by claim 1 wherein Q is O.
22. A compound as claimed by claim 1 wherein Q is a bond.

* * * * *